(12) United States Patent
Mizuyoshi

(10) Patent No.: US 8,337,400 B2
(45) Date of Patent: Dec. 25, 2012

(54) ILLUMINATION DEVICE FOR USE IN ENDOSCOPE

(75) Inventor: Akira Mizuyoshi, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 74 days.

(21) Appl. No.: 12/837,124

(22) Filed: Jul. 15, 2010

(65) Prior Publication Data

US 2010/0280322 A1 Nov. 4, 2010

Related U.S. Application Data

(63) Continuation of application No. 12/478,704, filed on Jun. 4, 2009.

(30) Foreign Application Priority Data

| Jun. 4, 2008 | (JP) | 2008-146660 |
| Jun. 11, 2008 | (JP) | 2008-152932 |
| Jun. 13, 2008 | (JP) | 2008-155597 |
| Jun. 13, 2008 | (JP) | 2008-156047 |

(51) Int. Cl.
  *A61B 1/06* (2006.01)
(52) U.S. Cl. ..................................... 600/178
(58) Field of Classification Search .................. 600/178
  See application file for complete search history.

(56) References Cited

U.S. PATENT DOCUMENTS

| 4,821,117 A * | 4/1989 | Sekiguchi ........................ 348/68 |
| RE34,411 E | 10/1993 | Nishioka et al. |
| 5,420,080 A | 5/1995 | Wang et al. |
| 5,439,616 A | 8/1995 | Ishiwata et al. |
| 5,545,595 A | 8/1996 | Wang et al. |
| 6,350,041 B1 | 2/2002 | Tarsa et al. |
| 6,602,186 B1 * | 8/2003 | Sugimoto et al. ............. 600/126 |
| 7,020,378 B2 | 3/2006 | Poisel et al. |

(Continued)

FOREIGN PATENT DOCUMENTS

DE  10 2006 053 487 A1  5/2008

(Continued)

OTHER PUBLICATIONS

Trials for development and clinical application of an electronic endoscope system having a built-in narrow band filter (Narrow Band Imaging: NBI) (Yasushi Sano, Shigeaki Yoshida (National Cancer Center East Hospital), Masahiko Kobayashi (Self-Defense Forces Central Hospital), GastroenterolEndosc, Sep. 20, 2000.). Discussed in the present specification at p. 2. Translation provided.

(Continued)

*Primary Examiner* — Philip R Smith
*Assistant Examiner* — Arnaldo Torres Diaz
(74) *Attorney, Agent, or Firm* — McGinn IP Law Group, PLLC

(57) ABSTRACT

An illumination device for use in an endoscope includes a light source, an optical fiber and a wavelength conversion member. The optical fiber guides light to a tip end of an endoscope insertion portion of the endoscope. The wavelength conversion member is provided at an emission end of the optical fiber. The wavelength conversion member configured to be excited by the light source. The illumination device can provide white illumination light obtained by mixing light emitted from the optical fiber and light obtained by exciting the wavelength conversion member by the light emitted from the optical fiber. Also, the illumination device can provide illumination light being different from the white illumination light, by using other excitation light.

12 Claims, 35 Drawing Sheets

U.S. PATENT DOCUMENTS

| | | | |
|---|---|---|---|
| 7,179,222 B2* | 2/2007 | Imaizumi et al. | 600/109 |
| 7,235,045 B2* | 6/2007 | Wang et al. | 600/109 |
| 7,330,205 B2* | 2/2008 | Hakamata | 348/65 |
| 8,197,111 B2 | 6/2012 | Hama et al. | |
| 2003/0007087 A1 | 1/2003 | Hakamata et al. | |
| 2005/0124858 A1 | 6/2005 | Matsuzawa et al. | |
| 2005/0288553 A1 | 12/2005 | Sugimoto | |
| 2006/0149133 A1* | 7/2006 | Sugimoto et al. | 600/160 |
| 2006/0152926 A1 | 7/2006 | Hama et al. | |
| 2006/0173245 A1 | 8/2006 | Todd et al. | |
| 2006/0235277 A1* | 10/2006 | Ohkubo et al. | 600/179 |
| 2007/0149858 A1* | 6/2007 | Ogawa et al. | 600/181 |
| 2007/0213592 A1 | 9/2007 | Yamada | |
| 2007/0297190 A1 | 12/2007 | Ng | |
| 2008/0039697 A1 | 2/2008 | Morishita | |
| 2008/0051632 A1* | 2/2008 | Ito et al. | 600/114 |
| 2008/0089089 A1* | 4/2008 | Hama et al. | 362/574 |
| 2008/0205477 A1 | 8/2008 | Hama et al. | |
| 2008/0239070 A1 | 10/2008 | Westwick et al. | |
| 2009/0040598 A1* | 2/2009 | Ito | 359/332 |
| 2009/0065679 A1 | 3/2009 | Tanimoto | |
| 2009/0167149 A1 | 7/2009 | Ito | |
| 2009/0194699 A1* | 8/2009 | Smitt et al. | 250/339.12 |
| 2009/0306478 A1 | 12/2009 | Mizuyoshi | |
| 2009/0312607 A1 | 12/2009 | Sunagawa et al. | |
| 2010/0016669 A1 | 1/2010 | Takaoka et al. | |
| 2010/0094136 A1 | 4/2010 | Nakaoka et al. | |
| 2010/0256504 A1 | 10/2010 | Moreau-Gaudry et al. | |

FOREIGN PATENT DOCUMENTS

| | | |
|---|---|---|
| EP | 1 575 423 A | 9/2005 |
| EP | 1 787 571 A | 5/2007 |
| EP | 1 787 571 A1 | 5/2007 |
| EP | 1 795 798 A | 6/2007 |
| EP | 1 867 272 A | 12/2007 |
| EP | 2 026 108 A | 2/2009 |
| JP | Sho. 60-225820 A | 11/1985 |
| JP | Hei. 6-40174 B | 5/1994 |
| JP | Hei. 7-69673 A | 3/1995 |
| JP | Hei. 7-97572 A | 4/1995 |
| JP | 2641653 B2 | 5/1997 |
| JP | 10-243915 (A) | 9/1998 |
| JP | 2001-170009 A | 6/2001 |
| JP | 2003-61909 (A) | 3/2003 |
| JP | 2005-198794 A | 7/2005 |
| JP | 2005-205195 A | 8/2005 |
| JP | 2005-328921 A | 12/2005 |
| JP | 2006-002115 A | 1/2006 |
| JP | 2006-61685 A | 3/2006 |
| JP | 2006-68488 (A) | 3/2006 |
| JP | 2006-166940 (A) | 6/2006 |
| JP | 2006-173324 A | 6/2006 |
| JP | 2006-288535 (A) | 10/2006 |
| JP | 2007-95809 (A) | 4/2007 |
| JP | 2007-111151 A | 5/2007 |
| WO | WO 2006/038502 (A1) | 4/2006 |

OTHER PUBLICATIONS

Phosphor for White LED, Tsutomu Odaki, IEICE Technical Research Report ED2005-20, CFM2005-28, SDM2005-28, pp. 69-74 (May 2005). Discussed in the present specification at p. 48. Partial translation provided.

New SiALON phosphors and white LEDs, Naoto Hirosaki, Xie Rong Jun and Ken Sakuma, Transactions of JSAP, vol. 74, No. 11, pp. 1449-1452 (2005). Discussed in the present specification at p. 48. Partial translation provided.

Present status and prospect of multinary phosphor materials, Hajime Yamamoto, School of Bionics, Tokyo University of Technology, Transactions of JSAP, vol. 76, No. 3, p. 241 (2007). Discussed in the present specification at p. 48. Partial translation provided.

Extended European Search Report Sep. 21, 2010.

Extended European Search Report of Sep. 2, 2009.

United States Office Action dated Mar. 26, 2012, in U.S. Appl. No. 12/478,704.

Extended European Search Reports dated Oct. 5, 2009, and Aug. 25, 2009.

U.S. Office Action dated Aug. 15, 2012, for U.S. Appl. No. 12/484,198.

Japanese Office Action dated Sep. 4, 2012, with English translation.
Japanese Office Action dated Sep. 25, 2012, with English translation.

* cited by examiner

FIG. 12A
FIG. 12B
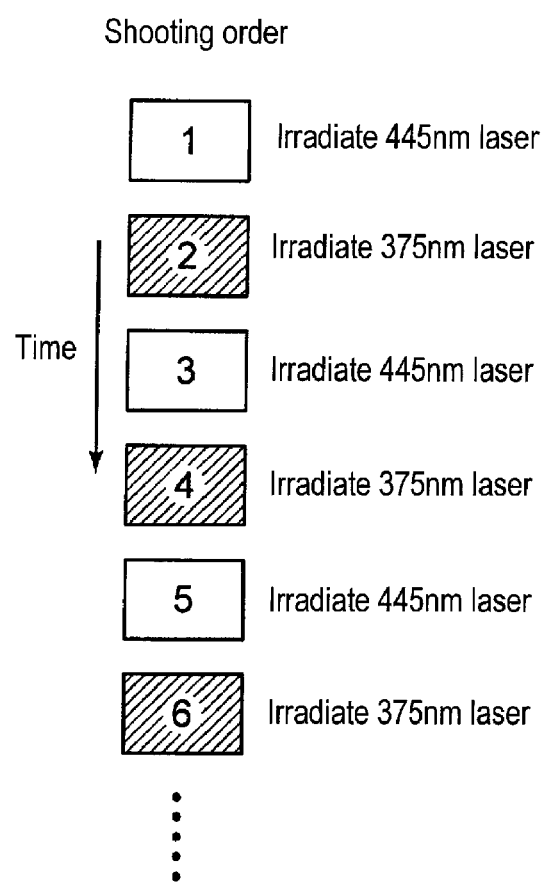
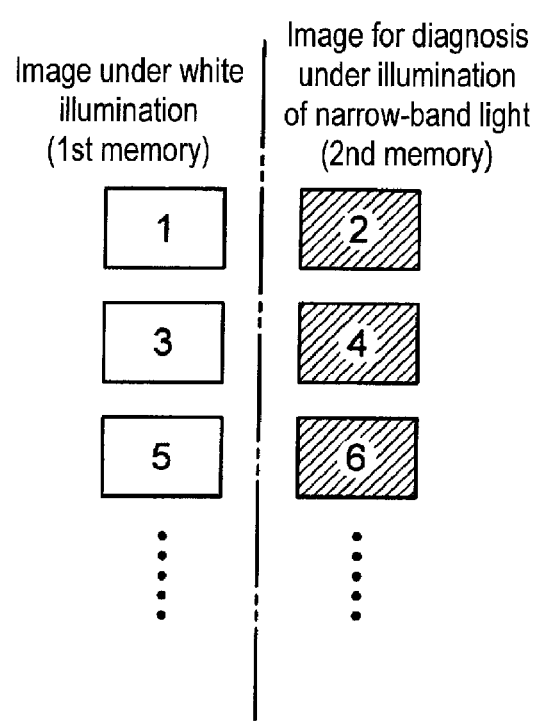

ILLUMINATION DEVICE FOR USE IN ENDOSCOPE

CROSS-REFERENCE TO RELATED APPLICATIONS

This application is a continuation of U.S. application Ser. No. 12/478,704, filed on Jun. 4, 2009 which claims priority from Japanese Patent Application Nos. 2008-146660 (filed on Jun. 4, 2008), 2008-152932 (filed on Jun. 11, 2008), 2008-155597 (filed on Jun. 13, 2008) and 2008-156047 (filed on Jun. 13, 2008), the entire contents these documents hereby incorporated by reference, the same as if set forth at length.

BACKGROUND OF THE INVENTION

1. Technical Field

The invention relates to an illumination device for use in an endoscope.

2. Description of the Related Art

In light source devices using a laser beam, various types of light source devices which obtain white light by a laser beam and visible light generated by a wavelength conversion member, such as a phosphor excited by the laser beam, have been proposed. In these types of light source devices, a laser beam has a line spectrum in a specific wavelength region. Accordingly, a wavelength region where the emission intensity is low may be generated over a relatively wide range around the wavelength region of the line spectrum. For this reason, in normal illumination, a phosphor which emits light in a broad wavelength region is appropriately selected in order to improve the color rendering properties. Moreover, the wavelength region where the emission intensity is low may be compensated by adding other kinds of laser beams in addition to the above laser beam. For example, JP 2006-173324 A (corresponding to US 2006/0152926 A and US 2008/0205477 A) describes an example where a blue laser beam as excitation light and a laser beam having a different excitation wavelength from the blue laser beam are added.

Meanwhile, in a light source device for use in the endoscope filed, illumination light for diagnosis under light in a specific wavelength band may be required in addition to obtaining white light having high color rendering properties. In a technique called a spectral diagnostics in the endoscope filed, a new blood vessel, which is generated in a mucous membrane layer or an underlying layer of a mucous membrane, is observed using the light in the specific wavelength band so as to determine if there is cancer. Illumination light used for observation has a larger scattering characteristic as the wavelength becomes short. Therefore, information about a relatively shallow layer can be obtained with a short wavelength, and information about a relatively deep layer can be obtained with a long wavelength. For this reason, in case of observing the surface microstructure while a deep reaching degree of light is limited to a surface layer, it is important to make a band of illumination light narrow in order to improve the contrast. For example, JP Hei.6-40174 A describes an endoscope for performing an illumination operation with light which is in a narrow wavelength band and which is extracted by using a narrow-band filter.

Moreover, for endoscopic diagnosis of an upper alimentary canal, a nasal endoscope less stressful to a patient is being used in place of a peroral endoscope. In the case of the nasal endoscope, an insertion portion is thinner than that of the peroral endoscope, and it is difficult to secure the thickness of a light guide. Accordingly, in order to capture a bright image, improvements are required such as increasing an amount of illumination light or improving a sensitivity of an imaging device.

Furthermore, also in the thin endoscope, measurement and diagnosis in a narrow band are beginning to be required. Narrow-band diagnosis is disclosed in "Trials for development and clinical application of an electronic endoscope system having a built-in narrow band filter (Narrow Band Imaging: NBI)" (Yasushi Sano, Shigeaki Yoshida (National Cancer Center East Hospital), Masahiko Kobayashi (Self-Defense Forces Central Hospital), GastroenterolEndosc, Sep. 20, 2000.).

Also, JP 2641653 B2 describes an electronic endoscope capable of selecting an optimal wavelength region according to an observed body and acquiring a normal color image (visible information) with time-series illumination within a visible wavelength band using a solid state imaging device provided in the tip portion of the endoscope. The electronic endoscope of this reference is also capable of acquiring an image with infrared light or ultraviolet light by illuminating such light, which includes an infrared or ultraviolet wavelength band other than the visible wavelength band, in a time-series manner in order to easily detect a color tone difference of each part of the observed body, which is difficult to be distinguished in a normal image in the visible region, and displaying the image with desired colors assigned. Therefore, JP 2641653 B2 describes that a laser or an LED which emits light in a narrow wavelength region is exemplified as a light source for performing illumination using light in the narrow wavelength region. Also, JP 2641653 B2 describes that a light source being provided with an absorption type filter in which coloring materials are mixed or a vapor-deposited type filter on an emission port of a lamp which emits light in a wide band, such as a xenon lamp, a halogen lamp, and a strobe lamp in order to limit an output wavelength may also be used. Moreover, JP 2641653 B2 describes that a plurality of such light sources are used in a wavelength region from an ultraviolet region to an infrared region. In addition, since various kinds of illumination light in a predetermined wavelength region from an ultraviolet region to an infrared region need to be guided in JP 2641653 B2, it describes that illumination light emitted from the light source is guided to the tip of the endoscope by a light guide similar as in the related art.

Thus, the endoscope for use in spectral diagnostics is requested to emit narrow-band light while making it compact. In a light source described in JP 2006-173324 A, in order to obtain emission of green light having a narrow bandwidth, coupling using a so-called DPSS green SHG laser by second harmonic generation is performed on the light source side, for example, by using a prism. However, in this method, it is requested that a phosphor, which is excited by a blue laser beam to emit light of green to red colors do not absorb, for example, green light introduced by other laser beams. That is, as a phosphor disposed in the middle of an optical path in order to acquire white light, there is no choice but to apply only a phosphor which rarely absorbs a laser beam for obtaining light in a specific wavelength band other than a laser beam for generation of white light. Moreover, in case of performing illumination with such a green laser, a noise is easily superimposed on a captured image because of speckle (interference) or flickering easily occurs on a dynamic image due to the high coherence. Moreover, it may be conceived to eliminate the limitation of a phosphor by providing a white light illumination optical system and an illumination optical system of a specific wavelength band as separate optical paths. However, particularly in an endoscope, a light guide serving as an optical path becomes bulky. In addition, since it is necessary to provide a new irradiation window at the tip of an insertion portion, it becomes difficult to make the insertion portion thin. Moreover, the light source described in JP 2006-173324 A irradiates light in a visible wavelength region like JP Hei.6-40174 A or the non-patent document ('Trials for development and clinical application of an electronic endoscope system with a built-in narrow band filter (Narrow Band Imaging: NBI)'). Accordingly, in order to improve the color rendering properties, the wavelength width of emitted light is made wide. Therefore, in order to acquire a narrow-band imaging signal of a blue or green color which is useful especially for an endoscope, there still remains many problems in a combination of suitable phosphors, switching of excitation light sources in a time-series manner, a signal calculating method, and the like. That is, it is still difficult to precisely separate the emission wavelength band by switching of excitation light and to make light selectively emitted.

In the case of mounting a light emitting device, such as an LED or a semiconductor laser, in a tip portion of the endoscope, particularly in the case of disposing a plurality of light emitting devices as described in JP Sh.60-225820 A, it is requested to make the light emitting devices very small and thin. Thus, in the case of white illumination suitable for illumination of an endoscope, for example, in the case of using a white LED or a white laser, the illumination system may be configured by a semiconductor laser or an LED used as an excitation light source and a phosphor as described in JP 2005-205195 A and JP 2006-173324A. In this case, however, trade-offs between making the phosphor very large and improving the efficiency occur. For this reason, since there was limitation in the size of a phosphor when a light emitting device is mounted at the tip portion of the endoscope, there was also limitation in improving the efficiency.

On the other hand, infrared light and ultraviolet light other than a visible range may also be used to acquire a useful image for diagnostic imaging, especially medical image diagnosis like the endoscope described in JP 2641653 B2. However, the endoscope apparatus described in JP 2641653 B2 is an apparatus in which both light in a visible range and infrared light or ultraviolet light other than the visible range are used by switching light having a narrow-band wavelength in a time-series manner, and such light components are directly incident on a light guide to be then directly irradiated to a body to be inspected from the tip of the light guide, but is not an apparatus that irradiates white light including plural wavelength components in a visible range. Therefore, JP 2641653 B2 describes that a fiberscope which uses an optical fiber may be used instead of the electronic endoscope which uses a light guide. However, in the technique described in JP 2641653 B2, the optical fiber is used only to guide light having many narrow-band wavelengths like a light guide. Accordingly, in the endoscope described in JP 2641653 B2, even if an optical fiber is used in place of the light guide, it was not possible to use a white LED and a white laser, which are described in JP 2005-205195 A and JP 2006-173324 A in which white light is obtained by making light emitted from a semiconductor laser or an LED serving as an excitation light source incident on a light guide or an optical fiber and by coating the tip of the light guide or the optical fiber with a phosphor.

Moreover, it is assumed that as a light source of an endoscope, used is a white LED or a white laser including: a semiconductor laser or an LED which emit excitation light, for example, blue excitation light; an optical fiber which guides the excitation light; and a phosphor provided at the tip of an optical fiber and excited by excitation light as described in JP 2005-205195 A and JP 2006-173324 A and that an infrared emitting device which is useful in medical fields and emits infrared light other than a visible range like the endoscope described in JP 2641653 B2. In this case, the infrared light could not be efficiently guided in the related art because the optical fiber which guides the excitation light is configured to efficiently guide the excitation light. In addition, in the case of a phosphor for use in the known white LED or white laser, there was a problem that the infrared light was wavelength-converted into fluorescent light.

For this reason, in a light source device of the related art for an endoscope, excitation light and infrared light are guided using separate optical fibers. An endoscope apparatus using such a light source device for an endoscope is shown in FIG. 32. As shown in FIG. 32, an endoscope apparatus 400 has an endoscope device 402 and a control device 404. The endoscope device 402 is configured to include an insertion portion 406, an operating section 408, a main body operating section 410, and a connection portion 412. The insertion portion 406 is configured to have a flexible soft portion 414, a bending portion 416, and a tip portion 418. A phosphor portion 420, an irradiation port 422 for illumination light, an objective lens (not shown), and a CCD 424 are provided in the tip portion 418 of the insertion portion 406. Moreover, the control device 404 includes a blue laser diode (hereinafter, referred to as an LD) 426 and an infrared LD 428, which serve as light sources of excitation light, a light source controller 430 that controls the blue LD 426 and the infrared LD 428 to emit light in a time-series manner, and a processor 432.

In addition, two optical fibers 434 and 436 and one scope cable 438 are inserted inside the endoscope device 402. The optical fibers 434 and 436 are inserted in the endoscope device 402. One ends of the optical fibers 434 and 436 are connected to the blue LD 426 and the infrared LD 428 of the control device 404, respectively, and the other ends extend to the tip portion 418 of the endoscope device 402. In the tip portion 418 of the endoscope device 402, the tip of the optical fiber 434 extends to the position of the phosphor portion 420 so that blue light from the blue LD 426 is incident on the phosphor portion 420 and is then emitted from the irradiation port 422 as white light (or pseudo white light) that becomes illumination light. The tip of the optical fiber 436 extends to the irradiation port 422 so that infrared light from the infrared LD 428 is emitted from the irradiation port 422. In addition, the scope cable 438 is a cable for transmission of an imaging signal. One end of the scope cable 438 is connected to the processor 430 of the control device 404, and the other end is connected to the CCD 424. The processor 430 converts the imaging signal transmitted from the CCD 424 into a video signal and supplies the video signal to a monitor (not shown).

Here, the blue LD 426, the infrared LD 428, the two optical fibers 434 and 436, and the phosphor portion 420 form a light source device 440. Details of the light source device 440 are shown in FIG. 33. As shown in FIG. 33, a collimator lens 442 is disposed between the blue LD 426 and the optical fiber 434, and an illumination optical member 446 to which the phosphor portion 420 is attached is provided at the tip of the optical fiber 434, which is held by a holding end portion 444. In addition, a collimator lens 448 is disposed between the infrared LD 428 and the optical fiber 436, and a concave lens 450 is provided at the tip of the optical fiber 436. In the light source device 440 of the related art, infrared light from the infrared LD 428 is independently guided by the optical fiber 436. Therefore, the concave lens 450 is needed at the tip of the optical fiber in order to increase the divergence angle of the infrared light.

In the case where, like this light source device 440, a white laser configured to include the blue LD 426, the optical fiber 434, and the phosphor portion 420 are used as an observation light source, if the infrared LD 428 is used together as an observation light source for making observation under the infrared light that is effective in the medical field, the dedicated optical fiber 436 which guides the infrared light and is different from the optical fiber 434 guiding blue excitation light from the blue LD 426 needs to be used. However, the resultant device configuration is complicated, and it is difficult to reduce a size of the device. In addition, emission positions of white light and infrared light are not identical. Therefore, for example, when normal images under the white light and images under the infrared light are acquired in a time-series manner and displayed, a difference between images and/or appearance of a shadow would be conspicuous. Therefore, it is difficult to compare the images.

Moreover, in the case where an infrared emission LED device is used to make observation under infrared light that is effective in the medical field, even if a white (or pseudo white) LED formed of a blue LED device and a phosphor and an infrared emission LED device are integrated as a light source device for an endoscope, it is necessary to seal the white LED and the infrared emission LED device. Such a light source device for an endoscope is shown in FIG. 34. As shown in FIG. 34, a light source device 460 includes: a common substrate 464 formed with two recesses 462 and 463 separated by a separation barrier 461; a blue LED device 468 fixed to the recess 462 by an adhesive 466; a resin sealing portion 470, which seals the blue LED device 468 provided in the recess 462, in a sealing region with a phosphor-containing resin in which a phosphor is mixed; an infrared emission LED device 472 fixed to the recess 463 of the common substrate 464 by an adhesive; and a resin sealing portion 474, which seals the infrared emission LED device 472 provided in the recess 463, in a sealing region with a resin in which a phosphor is not mixed, the resin sealing portion 474 which allows infrared light to transmit therethrough. Here, the blue LED device 468 and the resin sealing portion 470 formed of the phosphor-containing resin form a white (or pseudo white) LED, and white light (or pseudo white light) is emitted from the resin sealing portion 470. In addition, the infrared emission LED device 472 emits infrared light through the resin sealing portion 474.

In the case where, like this light source device 460, a white LED including the blue LED device 468 and the resin sealing portion 470 formed of the phosphor-containing resin is used as an observation light source, if the infrared LED 472 is used together as an observation light source for making observation under the infrared light that is effective in the medical field, it is necessary to use a resin in which a phosphor is not mixed for sealing the infrared LED 472, while it is necessary to mix the phosphor, which is excited by blue excitation light from the blue LED device 468 and converts wavelength into white light (or pseudo white light), in a resin for sealing the blue LED device 468, while a resin in which a phosphor is not mixed needs to be used as a resin for sealing the infrared emission LED device 472. Therefore, it would be difficult to achieve efficient white illumination and to reduce a size of the device. In addition, since emission sources of white light and infrared light are not identical, for example, when normal images under the white light and images under the infrared light are acquired in a time-series manner and displayed, a difference between images and/or a difference in appearance of shadows are conspicuous. Therefore, it is difficult to compare both the images.

SUMMARY

The invention provides an illumination device for use in an endoscope that mixes light emitted from an optical fiber and light obtained by exciting a wavelength conversion member by the light emitted from the optical fiber for irradiation as while illumination light.

According to a first aspect of the invention, an illumination device for use in an endoscope includes a light source, an optical fiber and a wavelength conversion member. The optical fiber guides light to a tip end of an endoscope insertion portion of the endoscope. The wavelength conversion member is provided at an emission end of the optical fiber. The wavelength conversion member configured to be excited by the light source. Light emitted from the optical fiber and light obtained by exciting the wavelength conversion member by the light emitted from the optical fiber are mixed to generate white illumination light.

Also, the light guided through the optical fiber may have different plural wavelengths. The wavelength conversion member may be disposed at the tip end of the endoscope insertion portion and is separately excited by the light of the respective wavelengths.

Also, the illumination device may further include a light emitting device that is provided at the tip of the endoscope insertion portion and emits light in a visible wavelength band.

Also, the illumination device may further include an illumination light control unit that alternately switches between illumination with the white light and illumination including light in a specific visible wavelength band, every imaging frame of an imaging device of the endoscope.

Also, the light source may include a first light source and a second light source. The first light source that emits a laser beam having a first wavelength as a center wavelength. The second light source emits an infrared laser beam having a second wavelength included in an infrared wavelength band as a center wavelength. The wavelength conversion member may include a first wavelength conversion member and a second wavelength conversion member. The first wavelength conversion member is configured to be excited by the laser beam of the first light source to emit light. The second wavelength conversion member is configured to be excited by the infrared laser beam of the second light source to emit light that is in a specific visible wavelength band and is shorter than the second wavelength. A band width of the light emitted by the second wavelength conversion member is narrower than a substantial sensitive wavelength band, for a specific detection color corresponding to the light emitted by the second wavelength conversion member, of an imaging device.

Also, the light source may include a first light source and a second light source. The first light source emits a laser beam having a first wavelength as a center wavelength. The second light source emits an infrared laser beam having a second wavelength included in an infrared wavelength band as a center wavelength. The wavelength conversion member may include a first wavelength conversion member and a second wavelength conversion member. The first wavelength conversion member is configured to be excited by the laser beam of the first light source to emit light. The second wavelength conversion member is configured to be excited by the infrared laser beam of the second light source to emit light that is in a specific visible wavelength band and is shorter than the second wavelength. The light, which that the second wavelength conversion member is excited by the infrared laser beam of the second light source to emit, may be in a wavelength band of 530 nm to 570 nm.

Also, the light source may include a first light source and a second light source. The first light source emits light having a first wavelength. The second light source emits light having a second wavelength different from the first wavelength. The wavelength conversion member may be configured to be excited by the light of the first light source to emit first fluorescence having a wavelength different from the first wavelength. An energy of fluorescence of the wavelength conversion member when the wavelength conversion member is excited by light having the second wavelength and having a certain energy may be equal to or less than 1/10 of that of fluorescence of the wavelength conversion member when the wavelength conversion member is excited by light having the first wavelength and having the certain energy. Also, the energy of the fluorescence of the wavelength conversion member when the wavelength conversion member is excited by the light having the second wavelength and having the certain energy may be equal to or less than 1/100 of that of the fluorescence of the wavelength conversion member when the wavelength conversion member is excited by the light having the first wavelength and having the certain energy.

Also, the energy of the fluorescence of the wavelength conversion member when the wavelength conversion member is excited by the light having the second wavelength and having the certain energy may be equal to or less than 1/10,000 of that of the fluorescence of the wavelength conversion member when the wavelength conversion member is excited by the light having the first wavelength and having the certain energy.

Also, the wavelength conversion member may be an up-conversion material including oxide-fluoride-based crystallized glass.

Also, the wavelength conversion member may include a down-conversion material that emits green light by excitation.

Also, the wavelength conversion member may include a down-conversion material that emits blue light by excitation.

The invention may provide: an illumination device for use in an endoscope that can selectively irradiate either white light, which is generated to include a laser beam and luminescence of a phosphor, or light in a specific narrow visible wavelength band with a simple configuration while achieving its compact configuration; and an endoscope apparatus including the illumination device.

(1) According to a second aspect of the invention, a light source device includes a first light source, an optical fiber, a first wavelength conversion member, a second light source, an optical coupling unit and a second wavelength conversion member. The first light source emits a laser beam having a first wavelength as a center wavelength. The laser beam of the first light source is incident on a light indent side of the optical fiber and is transmitted through the optical fiber. The first wavelength conversion member is disposed on a light emission side of the optical fiber and is excited by the laser beam of the first light source to emit luminescence. The laser beam of the first light source and the luminescence from the first wavelength conversion member are mixed to obtain while light. The second light source emits an infrared laser beam having a second wavelength included in an infrared band as a center wavelength. The optical coupling unit introduces the infrared laser beam of the second light source to an optical path on the light incident side of the optical fiber. The second wavelength conversion member is disposed anterior to the light incident side of the optical fiber on the optical path. The second wavelength conversion member is excited by the infrared laser beam to emit luminescence which is in a specific visible wavelength band and which is shorter than the second wavelength. Either of the white light or the luminescence in the specific visible wavelength band is emitted selectively, or both of the white light and the luminescence in the specific visible wavelength band are emitted simultaneously.

With this light source device, the optical coupling unit causes an illumination optical system based on the first light source and an illumination optical system based on the second light source to be coaxial, and the first wavelength conversion member and the second wavelength conversion member are disposed anterior to the light incident side of the optical fiber on the optical path. Thereby, the luminescence caused by the laser beam from the first light source is obtained from the first wavelength conversion member, and the luminescence caused by the laser beam from the second light source is obtained from the second wavelength conversion member. As a result, since the white light is acquired by a part of the laser beam from the first light source and the luminescence from the first wavelength conversion member, and the luminescence in the specific visible wavelength band is obtained by exciting by the infrared laser beam from the second light source. Therefore, either the white light or the luminescence in the specific visible wavelength band can be emitted selectively with the simple configuration.

(2) In the light source device of (1), the second wavelength conversion member may be disposed anterior to the first wavelength conversion member on the optical path.

With this light source device, since the second wavelength conversion member is disposed anterior to the first wavelength conversion member on the optical path, the luminescence from the first wavelength conversion member is transmitted through the second wavelength conversion member while diffusing through the second wavelength conversion member. As a result, the white light is emitted while being diffused. Moreover, the laser beam of the second light source is transmitted through the second wavelength conversion member without loss while exciting the second wavelength conversion member to emit the luminescence in the specific wavelength band. The white light and the luminescence are emitted frontward on the optical path.

(3) In the light source device of (1), the second wavelength conversion member may be formed to be included in a light guiding material of the optical fiber.

With this light source, the optical fiber functions as the second wavelength conversion member since the optical fiber includes the light guiding material that is excited by the infrared laser beam to emit the luminescence, which is in the specific visible wavelength band and which is shorter than the second wavelength. Accordingly, since the second wavelength conversion member does not need to be disposed on the light emission side of the optical fiber, the further compact configuration can be realized.

(4) In the light source device according to any one of (1) to (3), the second wavelength conversion member may be an up-conversion material including oxide-fluoride-based crystallized glass.

With this light source, the luminescence in a narrow band of green can be obtained particularly by the light in the infrared wavelength band.

(5) According to a third aspect of the invention, an endoscope apparatus includes the light source device according to any one of (1) to (4), an endoscope and a control unit. The endoscope includes an illumination optical system and an imaging optical system. In the illumination optical system, the light emission side of the optical fiber of the light source device is disposed at a tip side of an endoscope insertion portion so as to illuminate a body to be inspected. The imaging optical system includes an imaging device that receives light from the body to be inspected and outputs an imaging signal. The control unit causes the white light and the luminescence in the specific visible wavelength band to be emitted simultaneously or causes either the white light or the luminescence in the specific visible wavelength band to be emitted selectively.

With this endoscope apparatus, the endoscope insertion portion can be made thin. Also, the white light or the luminescence in the specific visible wavelength band can be controlled to be selectively emitted as irradiated light. As a result, the spectral diagnostics can be performed easily.

(6) In the endoscope apparatus of (5), a wavelength width of the specific visible wavelength band in which the second wavelength conversion member emits the luminescence is narrower than a substantial effective sensitivity wavelength band, for a specific detection color corresponding to the luminescence, of the imaging device.

With this endoscope apparatus, the second wavelength conversion member emits the luminescence, which is in the wavelength band narrower than the substantial effective sensitivity wavelength band, for the specific detection color corresponding to the luminescence, of the imaging device. Therefore, there is no influence of color mixture and the like. Moreover, since region information about the invasion depth of the light which is one of the observation purposes can be acquired more reliably, the contrast of an obtained image can be increased in accordance with the observation purpose.

According to the light source device of any one of (1) to (4), either (i) white light, which is formed to include a laser beam and luminescence from a phosphor, or (ii) light in a specific narrow visible wavelength band can be selectively irradiated with the simple configuration. Moreover, according to the endoscope apparatus of any one of (5) to (6) using the light source device, the endoscope insertion portion can be made thin by simplifying the illumination optical system, and light irradiation can be performed by controlling either of the white light or the light in the specific visible wavelength band to be selectively emitted. As a result, spectral diagnostics and the like using the endoscope can be performed easily.

The invention may provide: an illumination device for use in an endoscope that can selectively irradiate either white light, which is generated to include a laser beam and luminescence of a phosphor, or light in a specific narrow visible wavelength band with a simple configuration while achieving its compact configuration; an endoscope apparatus including the illumination device; and an image processing method.

(7) According to a fourth aspect of the invention, a light source device includes a first light source, an optical fiber, a first wavelength conversion member, a second light source, an optical coupling unit and a second wavelength conversion member. The first light source emits a first laser beam having a first wavelength as a center wavelength. The first laser beam is incident on a light incident side of the optical fiber and is transmitted through the optical fiber. The first wavelength conversion member is disposed on a light emission side of the optical fiber. The first wavelength conversion member includes at least one kind of phosphor that emits luminescence upon excitation by the first laser beam. The first laser beam and the luminescence from the first wavelength conversion member are mixed to obtain white light. The second light source emits a second laser beam having a second wavelength, which is shorter than the first wavelength, as a center wavelength. The optical coupling unit introduces the second laser beam to an optical path on the light incident side of the optical fiber. The second wavelength conversion member is disposed anterior to the light emission side of the optical fiber on the optical path and emits luminescence which is in a specific visible wavelength band and which is longer than the second wavelength, upon excitation by the second laser beam.

With this light source device, the optical coupling unit causes an illumination optical system based on the first light source and an illumination optical system based on the second light source to be coaxial. The first wavelength conversion member and the second wavelength conversion member are disposed on the light emission side of the optical fiber. Thereby, the luminescence caused by the laser beam from the first light source is obtained from the first wavelength conversion member, and the luminescence caused by the laser beam from the second light source is obtained from the second wavelength conversion member. That is, the white light is obtained by a part of the first laser beams and the luminescence from the first wavelength conversion member, and the luminescence in the specific visible wavelength band is obtained by exciting by the infrared laser beam from the second light source. Therefore, either the white light or the luminescence in the specific visible wavelength band can be emitted selectively with the simple configuration.

(8) In the light source device of (7), the second wavelength conversion member may be excited by the first laser beam to emit luminescence.

With this light source device, the second wavelength conversion member, which is configured to be excited by the second laser beam to emit the luminescence, is also configured to be excited by the first laser beam to emit the luminescence. Therefore, light components which can be emitted from the light source device are increased. As a result, the light use efficiency can be improved. Moreover, since the combination of emitted light can be made in various ways, the degree of freedom of design at the time of light detection can be improved.

(9) The light source device of any one of (7) to (8) may further include a wavelength conversion member. In the wavelength conversion member, the first and second wavelength conversion members are integrated in a state where phosphors thereof are distributed or the first and second wavelength conversion members are laminated integrally.

With this light source device, the device size can be reduced because the wavelength conversion members are integrated. In addition, the luminescence caused by the first laser beam and the luminescence caused by the second laser beam are generated from the phosphors of the first and second wavelength conversion members, which are integrated, and are emitted frontward on the optical path.

(10) in the light source device of any one of (7) to (9), the second wavelength conversion member may include a down-conversion material which is excited to emit green light.

With this light source device, since the second wavelength conversion member emits green light, the green light can be supplied when performing spectral diagnostics of an endoscope, for example. Accordingly, illumination light corresponding to the diagnostic purpose can be obtained.

(11) In the light source device of any one of (7) to (10), the second wavelength conversion member includes a down-conversion material which is excited to emit blue light.

With this light source device, since the second wavelength conversion member emits blue light, the blue light can be supplied when performing spectral diagnostics of an endoscope, for example. Accordingly, illumination light corresponding to the diagnostic purpose can be obtained. Moreover, a pseudo color image for spectral diagnostics may be generated by making the blue light emitted together with green light.

(12) According to a fifth aspect of the invention, an endoscope apparatus includes the light source device of any one of (7) to (11), an endoscope, and a control unit. The endoscope includes an illumination optical system and an imaging optical system. In the illumination optical system, a light emission portion of the optical fiber of the light source device is disposed at a tip side of an endoscope insertion portion so as to illuminate a body to be inspected. The imaging optical system includes an imaging device which receives light from the body to be inspected and outputs an imaging signal. The control unit controls emission of laser beams from the first and second light sources.

With this endoscope apparatus, the endoscope insertion portion can be made thin. Also, the white light and the luminescence in the specific visible wavelength band can be controlled to be selectively emitted as irradiated light. Therefore, the spectral diagnostics can be performed easily.

(13) The endoscope apparatus of (12) may further include a first memory, a second memory and an imaging image display unit. The first memory stores an imaging signal imaged under illumination light of the white light generated by the first light source. The second memory stores an imaging signal imaged under illumination light including the luminescence, which is in the specific visible wavelength band and is generated by the second light source. The imaged image display unit displays the imaging signals, which are stored in the first and second memories, in different display regions, respectively.

With this endoscope apparatus, the imaging signals are stored in the different memories according to a type of illumination light. The imaging signals of the memories are displayed in the different display regions, respectively. Accordingly, for example, an observed image under illumination light based on the white light and an observed image under illumination light based on the luminescence in the specific visible wavelength band can be displayed separately. As a result, it is possible to perform diagnosis while comparing the normal observed image with the image observed in the specific wavelength.

(14) In the endoscope apparatus of (13), the control unit may alternately switch between illumination with the white light and illumination including the luminescence in the specific visible wavelength band, every imaging frame of the imaging device.

With this endoscope, by alternately imaging an image under illumination of the white light and an image under illumination including the luminescence in the specific visible wavelength band, the both images can be acquired approximately at the same time. Accordingly, two types of image information can be simultaneously displayed in real time.

(15) In the endoscope apparatus of any one of (12) to (14), the imaging device may include a color filter for detecting a specific detection color component. A full width of an emission spectrum curve of the specific visible wavelength band in which the wavelength conversion member is excited to emit the luminescence at half maximum the emission spectrum curve is narrower than a full width of a spectral sensitivity curve of a wavelength band in which the specific detection color of the color filter is detected, at half maximum of the spectral sensitivity curve.

With this endoscope apparatus, the full width of the specific visible wavelength band in which the wavelength conversion member is excited to emit the luminescence at the half maximum of the specific visible wavelength is set to be narrower than the full width of the detection wavelength band of the color filter at the half maximum of the detection wavelength band of the color filter. Thereby, the luminescence is detected in a corresponding wavelength band, and the other wavelength bands are not influenced. Accordingly, there is no influence of color mixture and the like. Moreover, since it becomes easy to adjust the invasion depth of light with respect to a region to be observed, information from a layer to be observed can be reliably acquired, and the contrast of an imaged image can be improved.

(16) According to a sixth aspect of the invention, an image processing method for use in the endoscope apparatus of any one of (12) to (15) images a frame image, which is configured to include plural detection color screens on which light components in different specific wavelength bands are detected, multiple times, and irradiates light from plural types of light sources under different conditions in synchronization with an imaging timing of each frame image. The method includes imaging first and second frame images repeatedly, wherein an observed image when a body to be inspected is illuminated by the first light source is referred to as the first frame image, and an observed image when the body to be inspected is illuminated by the second light source is referred to as the second frame image. The method also includes performing a calculation process for brightness information of a specific detection color screen of the first frame image and brightness information of a specific detection color screen of the second frame image so as to analytically acquire an observed image under light of the specific wavelength component from the light source device.

With this image processing method for use in the endoscope apparatus, the observed image under light of a desired wavelength component can be selectively extracted by performing the calculation process for information of the detection color screens of the first and second frame images in combination. That is, the observed image under the light of the specific wavelength component, which cannot be directly obtained from a frame image obtained by single imaging can be analytically acquired by using frame images before and after the time axis.

(17) In the image processing method for use in the endoscope apparatus of (16), the observed image under the light of the specific wavelength component includes at least an observed image under emission light having a narrow wavelength bandwidth.

With this method, since an observed image under a light component in a narrow wavelength band is analytically obtained, the invasion depth is limited to a narrow range, for example, when observing a blood vessel or gland tube structure. As a result, an image with higher contrast can be obtained.

(18) In the method of any one of (16) to (17), the observed image under the light of the specific wavelength component includes at least an observed image under emission light having a wide wavelength bandwidth.

With this method, since an observed image under a light component having a wide wavelength bandwidth is analytically acquired, it is possible to obtain an image under white illumination with higher color rendering properties.

(19) In the method of any one of (16) to (18), the observed image under the light of the specific wavelength component is converted into a specific color tone to generate a pseudo color image.

With this method, a capillary vessel, a gland tube structure, and the like of a tissue surface can be highlighted, an observed object can be easily checked, which can improve the diagnostic precision.

According to the light source device of any one of (7) to (11), either (i) white light, which is formed to include a first laser beam and luminescence from a phosphor, or (ii) light in a specific narrow visible wavelength band can be selectively irradiated with the simple configuration. Moreover, according to the endoscope apparatus of any one of (12) to (15) using the light source device, the endoscope insertion portion can be made thin since the illumination optical system becomes simple. In addition, since light irradiation can be performed by controlling either the white light or the light in the specific visible wavelength band to be selectively emitted, spectral diagnostics and the like using the endoscope can be performed easily. Moreover, according to the image processing method of any one of (16) to (19), an observed image under light of a specific wavelength component which cannot be directly detected can be analytically acquired by using frame images before and after the time axis.

Also, the invention may provide: an endoscope apparatus that can make observation by selectively irradiating either white light or light in a specific narrow visible wavelength band with the simple configuration while making a diameter of an endoscope insertion portion small and suppressing heat emission of an LED device disposed at the tip of the endoscope insertion portion; and an image processing method that can perform spectral diagnostics more precisely based on image information from provided the endoscope apparatus.

(20) According to a seventh aspect of the invention, an endoscope apparatus includes a first light source, an optical fiber, a wavelength conversion member, a first illumination optical system and a second illumination optical system. The first light source emits a laser beam. The laser beam is incident on a light incident side of the optical fiber and is transmitted toward a tip of an endoscope insertion portion through the optical fiber. The wavelength conversion member is disposed on a light emission side of the optical fiber and includes at least one type of phosphor that is excited by the laser beam to emit luminescence. The first illumination optical system mixes the laser beam and the luminescence from the wavelength conversion member to emit white light from the tip of the endoscope insertion portion. The second illumination optical system is disposed at the tip of the endoscope insertion portion and includes a light emitting device that emits light in a specific visible wavelength band.

With this endoscope apparatus, the laser beam from the first light source is guided by the optical fiber and is then irradiated to the wavelength conversion member disposed the emission end of the optical fiber, thereby exciting the wavelength conversion member to emit the luminescence. As a result, the white light is generated by the original laser beam from the first light source and the luminescence, which realizes an optical system for white light illumination. Moreover, since the second illumination optical system having the light emitting device, which emits the light in the specific visible wavelength band, is provided, either white light illumination or illumination with the light in the specific visible wavelength band can be emitted selectively with the simple configuration. In addition, since the white illumination light is generated by using the laser beam, high-brightness light is obtained. In addition, since the light is guided by the optical fiber, the endoscope insertion portion can be made thin.

(21) In the endoscope apparatus of (20), the light emitting device of the second illumination optical system may include an LED device.

With this endoscope apparatus, high-efficiency and high-brightness light can be obtained. Moreover, since the laser beam of the first illumination optical system is used together, the light amount of the LED device from the tip of the endoscope insertion portion can be controlled. As a result, the tip of the endoscope insertion portion can be made small, and the heat emission can be controlled.

(22) In the endoscope apparatus of any one of (20) to (21), the second illumination optical system may include plural light emitting devices that emit light in different center wavelengths.

With this endoscope apparatus, various types of illumination light can be emitted by providing the plural light emitting devices.

(23) In the endoscope apparatus of any one of (20) to (22), the second illumination optical system may include at least a light emitting device that emits green light.

With this endoscope apparatus, an emphasized image can be generated in spectral diagnostics by emitting the green light.

(24) In the endoscope apparatus of any one of (20) to (23), the second illumination optical system may include at least a light emitting device that emits blue light.

With this endoscope apparatus, an emphasized image can be generated in spectral diagnostics by emitting the blue light.

(25) In the endoscope apparatus of any one of (20) to (24), the second illumination optical system may include at least light emitting devices that emit red light or infrared light.

With this endoscope apparatus, so-called infrared observation in which observation is made in a state where a drug easily absorbing infrared light is injected into the vein can be executed by emitting the red light or the infrared light.

(26) The endoscope apparatus of any one of (20) to (25) may further include an imaging unit and an illumination light control unit. The imaging unit includes an imaging device that receives light from an observed part through an observation window provided at the tip of the endoscope insertion portion and outputs an imaging signal. The illumination light control unit switches between white light from the first illumination optical system and the light in the specific visible wavelength band from the second illumination optical system, for illumination.

With this endoscope apparatus, the endoscope insertion portion can be made thin, and the white light and the light in the specific visible wavelength band can be controlled to be selectively emitted as irradiated light. Therefore, the spectral diagnostics and the like can be performed easily.

(27) The endoscope apparatus of (26) may further include a first memory, a second memory and an imaged image display unit. The first memory stores an imaging signal imaged under illumination with the white light by the first illumination optical system. The second memory stores an imaging signal imaged under illumination including the light in the specific visible wavelength band by the second illumination optical system. The imaged image display unit displays the imaging signals, which are stored in the first and second memories, in different display regions, respectively.

With this endoscope apparatus, imaging signals are stored in different memories according to the type of illumination light, and the imaging signals of the memories are displayed in the different display regions, respectively. Thereby, for example, an observed image under illumination with the white light and an observed image under illumination with the light in a specific visible wavelength band can be displayed separately. As a result, it is possible to perform diagnosis while comparing a normal observed image with an image observed with the light in the specific wavelength.

(28) In the endoscope apparatus of (27), the illumination light control unit may alternately switches between illumination of the white light and illumination including the light in the specific visible wavelength band, every imaging frame of the imaging device.

With this endoscope, by alternately imaging an image under illumination with the white light and an image under illumination including the light in the specific visible wavelength band, both the images can be acquired approximately at the same time. Accordingly, two types of image information can be simultaneously displayed in real time.

(29) In the endoscope apparatus according to any one of (26) to (28), the imaging device may include a color filter for detecting a specific detection color component. A full width of an emission spectrum curve of the specific visible wavelength band in which the light emitting device emits light, at half maximum of the emission spectrum curve, is smaller than a full width of a spectral sensitivity curve of a wavelength band in which the specific detection color of the color filter is detected, at half maximum of the spectral sensitivity curve.

With this endoscope apparatus, the full width of the specific visible wavelength band in which the light emitting device emits light, at the half maximum thereof, is set to be narrower than the full width of the detected wavelength band of the color filter, at the half maximum thereof. Thereby, the emission light of the light emitting device is detected within a peak of one corresponding wavelength band detection, and the other wavelength bands are not influenced. Accordingly, there is no influence of color mixture and the like. Moreover, since it becomes easy to adjust the invasion depth of light with a region to be observed, information from a layer to be observed can be reliably acquired and the contrast of an imaged image can be improved.

(30) According to an eighth aspect of the invention, an image processing method for use in the endoscope apparatus of any one of (26) to (29) includes imaging a frame image which is configured to include plural detection color screens on which light components in different specific wavelength bands are detected, multiple times and irradiating light from a plurality of types of light sources under different conditions in synchronization with an imaging timing of each frame image. The method further includes: imaging first and second frame images repeatedly wherein an observed image when a body to be inspected is illuminated by the first light source is referred to as the first frame image and an observed image when the body to be inspected is illuminated by the second light source is referred to as the second frame image; and combining brightness information of a specific detection color screen of the first frame image with brightness information of a specific detection color screen of the second frame image so as to analytically acquire an observed image under light of the specific wavelength component from the light source device.

With this image processing method for use in the endoscope apparatus, an observed image under light of a desired wavelength component can be selectively extracted by combining information of the detection color screens of the first and second frame images. That is, an observed image under the light of the specific wavelength component which cannot be directly obtained from a frame image obtained by performing single imaging can be analytically acquired by using frame images before and after the time axis.

(31) In the image processing method of (30), the observed image under the light of the specific wavelength component may include at least an observed image under emitted light having a narrow wavelength bandwidth.

With this method, since an observed image under the light component in the narrow wavelength band is analytically acquired, the invasion depth is limited to a narrow range, for example, when observing a blood vessel or gland tube structure. As a result, an image with higher contrast can be obtained.

(32) In the image processing method of (30), the observed image under the light of the specific wavelength component may include at least an observed image under emitted light having a wide wavelength bandwidth.

With this image processing method, since an observed image under light component having the wide wavelength bandwidth is analytically acquired, it is possible to obtain an image under white illumination with higher color rendering properties.

(33) In the image processing method of any one of (30) to (32), the observed image under the light of the specific wavelength component may be converted into a specific color tone to generate a pseudo color image.

With this image processing method, a capillary vessel and a gland tube structure of a tissue surface can be emphasized, and an observed object can be easily checked, which can improve the diagnostic precision.

According to the endoscope apparatus of any one of (20) to (29), the endoscope insertion portion can made thin, heat emission of the LED device disposed at the tip of the endoscope insertion portion can be suppressed, and observation can be performed by selectively irradiating either white light or light in a specific narrow visible wavelength band with the simple configuration. In addition, according to the image processing method of any one of (31) to (33), highly precise spectral diagnostics can be performed based on image information from the endoscope apparatus.

Also, the invention may provide: a low-cost light source device that can coaxially guide two types of emission light having different wavelengths, has a small size, has a small diameter and is used for various purposes; and an endoscope system including this light source device.

Furthermore, the invention may provide: a light source device that can realize efficient white illumination, has a small size, can make emission sources of white light and infrared light almost the same or guide the white light and the infrared light coaxially so that the emission positions thereof can be made almost the same, for example, and compare both images easily while decreasing a difference between the images and/or appearance of shadows even if the normal image under the white light and the image under the infrared light are acquired in a time-series manner and are displayed; and an endoscope apparatus using the light source device.

In order to achieve the above-described objects, the inventors studied a light source device that can realize efficient white illumination, has a small size and can make light emitting sources of white light and infrared light or the emission positions almost the same, for making an observation using white light and also for making an observation using infrared light (infrared ray) which was useful in the medical field, was used in imaging using absorption of hemoglobin, a difference in saturation of oxygen, and the like, and could be used for diagnosis. As a result, the inventors found out that even if blue light is guided by an optical fiber and is converted into white light by a phosphor disposed at a tip end of the optical fiber for illumination as in the white laser described in JP 2005-205195 A, emission positions of the white light and the infrared light can be made substantially the same by guiding emission light, such as the red light or the infrared light, which passes through a used phosphor without little exciting the phosphor, to the phosphor provided at the tip end of the optical fiber and by providing a light source, such as an infrared LD, which emits the red light or the infrared light, below the phosphor.

Also, the inventors found out that in a light source that obtains desired white color based on (i) excitation light and (ii) fluorescence emitted from a phosphor excited by an a light emitting device of ultraviolet light to blue light, such as an LED, light emitting sources could be made substantially the same by arranging the infrared element below the phosphor. Furthermore, the inventors found out that this configuration could realize the efficiency of white illumination and miniaturization. As a result, the inventors found out that a difference between the images or appearance of shadows was small and that comparison between both the images could be easily made when a normal image under white light and an image under infrared light were acquired in a time-series manner and displayed.

The white laser described in JP 2006-173324 A includes a semiconductor laser for emitting red light or infrared light which does not excite a phosphor but has a good condensing efficiency to an optical fiber and guides through the optical fiber the laser beam to the phosphor disposed at the tip end of the optical fiber, rather than inputting blue light or ultraviolet light as excitation light of the white laser as described in JP 2005-205195 A. The inventors found out that, by appropriately selecting a phosphor glass, an aggregate and a binder that constitute the phosphor, a function of expanding the divergence angle of light as a scattering body for red light or infrared light could be given to the phosphor and that as a result, it was possible to prevent a phenomenon as an obstacle in imaging, such as a speckle generated by potential interference, when using the semiconductor laser.

(34) According to a ninth aspect of the invention, a light source device includes a first light emitting device, a second light emitting device and a third light emitting device. The first light emitting device emits light having a first wavelength. The second light emitting device emits light having a second wavelength different from the first wavelength. The third light emitting device including or coated with one or more phosphors which are excited by the light emitted from the first light emitting device to emit first fluorescent light having an emission wavelength different from the first wavelength. An energy of fluorescence light of the third light emitting device when the third light emitting device is excited by light having the second wavelength and having a certain energy is equal to or less than $\frac{1}{10}$ of that of fluorescence light of the third light emitting device when the third light emitting device is excited by light having the first wavelength and having the certain energy

(35) In the light source device of (34), the energy of the fluorescence light of the third light emitting device when the third light emitting device is excited by the light having the second wavelength and having the certain energy is equal to or less than $\frac{1}{100}$ of that of the fluorescence light of the third light emitting device when the third light emitting device is excited by the light having the first wavelength and having the certain energy.

(36) In the light source device of any one of (34) to (35), the energy of the fluorescence light of the third light emitting device when the third light emitting device is excited by the light having the second wavelength and having the certain energy is equal to or less than $\frac{1}{10,000}$ of that of the fluorescence light of the third light emitting device when the third light emitting device is excited by the light having the first wavelength and having the certain energy.

(37) In the light source device of any one of (34) to (36), the second fluorescent light, which is emitted by excitation by the light emitted from the second light emitting device, can be substantially neglected as compared with the first fluorescent light emitted by excitation by the light emitted from the first light emitting device.

(38) The light source device of any one of (34) to (37) may further include a first optical fiber that guides first excitation light emitted from the first light emitting device. The one or more phosphors of the third light emitting device may be disposed at an emission end of the first optical fiber. The first fluorescent light emitted from the one or more phosphors excited by the first excitation light guided by the first optical fiber may be mixed in the one or more phosphors of the third light emitting device and be then emitted from the third light emitting device. Emission light of the second light emitting device may be emitted from the third light emitting device through the one or more phosphors of the third light emitting device.

(39) The light source device of (38) may further include a second optical fiber that guides the emission light of the second light emitting device. The one or more phosphors of the third light emitting device may be disposed to be positioned at an emission end of the second optical fiber. The emission light of the second light emitting device may be guided by the second optical fiber and be then emitted from the third light emitting device through the one or more phosphors of the third light emitting device.

Furthermore, a first optical fiber that guides first excitation light emitted from the first light emitting device and a second optical fiber that guides emission light of the second light emitting device may be further provided. The phosphors of the third light emitting device may be disposed at emission ends of the first and second optical fibers. The first excitation light and the first fluorescent light emitted from the phosphors excited by the first excitation light guided by the first optical fiber may be mixed in the phosphors of the third light emitting device and be then emitted from the phosphors. The emission light of the second light emitting device may be guided by the second optical fiber and be then emitted from the phosphor through the phosphors of the third light emitting device.

(40) In the light source device of (39), the first and second optical fibers may be the same one optical fiber. The one optical fiber may guide the first excitation light emitted from the first light source device and the emission light of the second light source device. The one or more phosphors of the third light emitting device may be disposed at the emission end of the one optical fiber. The first fluorescent light emitted from the one or more phosphors excited by the first excitation light guided by the one optical fiber may be mixed in the one or more phosphors of the third light emitting device and be then emitted from the third light emitting device. The emission light of the second light emitting device may be guided by the one optical fiber and be then emitted from the third light emitting device through the one or more phosphors of the third light emitting device.

(41) In the light source device of any one of (38) to (39), the second optical fiber or the one optical fiber may include a germanium oxide in a core thereof.

Furthermore, one optical fiber that guides first excitation light emitted from the first light emitting device and emission light of the second light emitting device may be provided. The phosphors of the third light emitting device may be disposed at an emission end of the one optical fiber. The first excitation light and the first fluorescent light emitted from the phosphors excited by the first excitation light guided by the one optical fiber may be mixed in the phosphors of the third light emitting device and be then emitted from the phosphors. The emission light of the second light emitting device may be guided by the one optical fiber and be then emitted from the phosphor through the phosphors of the third light emitting device.

(42) In the light source device of (38), the second light emitting device may be mounted below the one or more phosphors of the third light emitting device.

(43) In the light source device of (34) to (37), the first and second light emitting devices may be mounted below the one or more phosphors of the third light emitting device.

(44) In the light source device of (34) to (43), the second wavelength of the emission light of the second light emitting device may include a wavelength in an infrared region.

(45) According to tenth aspect of the invention, an endoscope apparatus includes the light source device of any one of (34) to (44).

According to the above-described configuration of any one of (34) to (45), it is possible to provide a light source device that can be made small and thin by making two emitted light components having different wavelengths guided coaxially and that can be made at low cost and has many applications, and an endoscope apparatus using the light source device. Furthermore, according to the above-described configuration of any one of (34) to (45), efficient white illumination and miniaturization of the device can be realized, and it is possible to make emission sources of white light and infrared light almost the same or the white light and the infrared light can be guided coaxially so that the emission positions thereof can be made almost the same. For example, comparison between both images can be easily performed by decreasing a difference between the images or appearance of shadows even when the normal image under the white light and the image under the infrared light are acquired in a time-series manner and displayed.

BRIEF DESCRIPTION OF THE DRAWINGS

FIG. 12A is an explanatory view conceptually illustrating plural frame images which are obtained in a time-series manner by imaging by an imaging optical system.

FIG. 12B is an explanatory view conceptually illustrating a state where the frame images of FIG. 12A are rearranged and displayed.

DETAILED DESCRIPTION OF EMBODIMENTS OF THE INVENTION

[First Embodiment]

Figure 1:
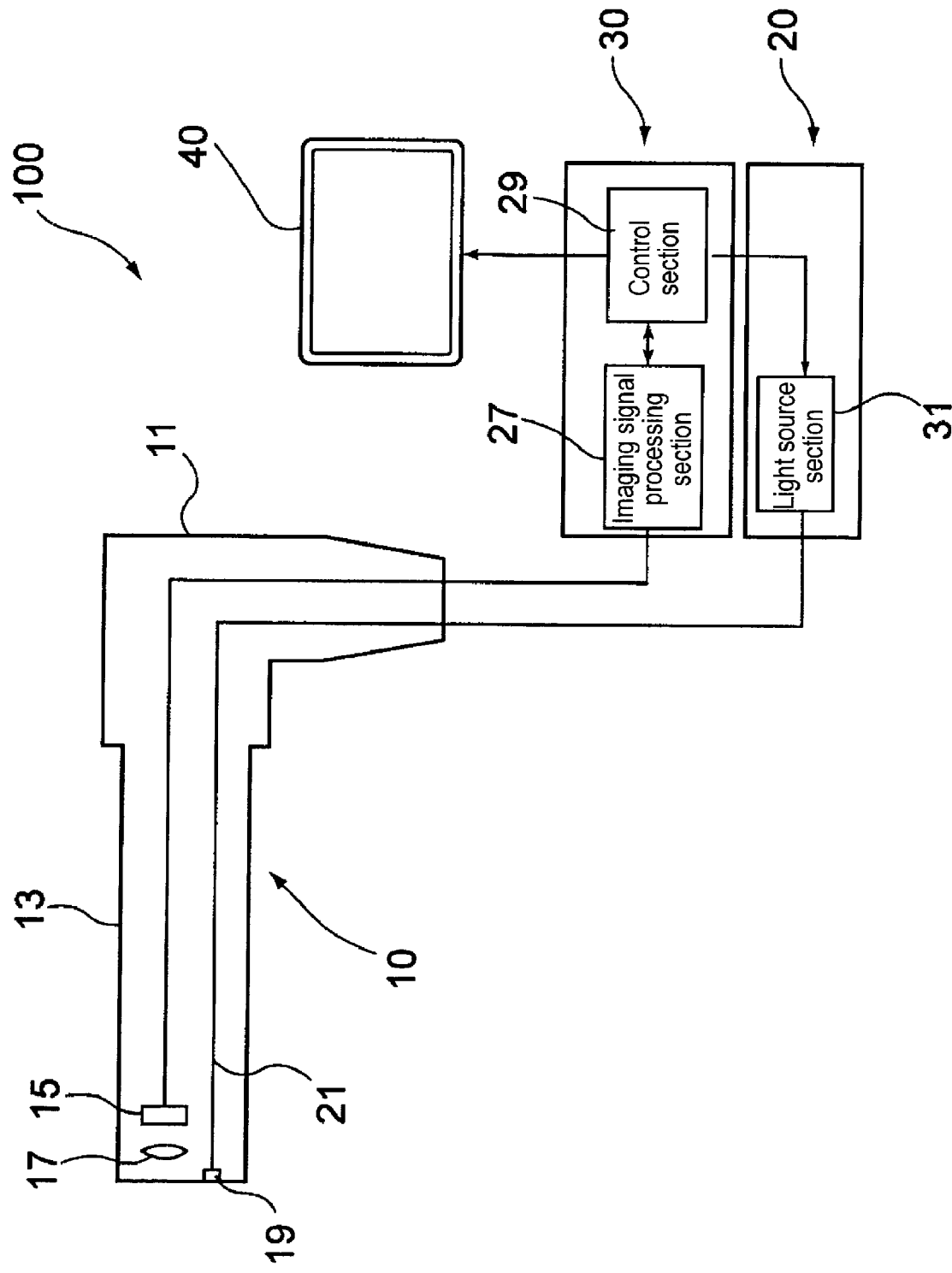
FIG. 1 is a view illustrating the conceptual configuration of an endoscope apparatus according to a first embodiment of the invention.

Hereinafter, a light source device according to a first embodiment and an endoscope apparatus using the light source device will be described in detail with reference to the accompanying drawings. FIG. 1 is a view illustrating the conceptual configuration of the endoscope apparatus according to the first embodiment. An endoscope apparatus 100 of the first embodiment is configured to mainly include an endoscope 10, a light source device 20, an image processing device 30, and a monitor 40. The endoscope 10 includes a main body operation portion 11 and an insertion portion 13 which is provided to be connected to the main body operation portion 11 and is inserted into a body to be inspected (body cavity). A solid-state imaging device 15 and an imaging lens 17 which constitute an imaging optical system are disposed in a tip portion of the insertion portion 13. Moreover, an illumination optical member 19, which is an illumination optical system, and an optical fiber 21 connected to the illumination optical member 19 are disposed near the imaging optical system. Also, the optical fiber 21 is connected to the light source device 20, which will be described in detail later. An imaging signal from the solid-state imaging device 15 is input to the image processing device 30.

An imaging device, such as a CCD (charge coupled device) or a CMOS (complementary metal-oxide semiconductor), is used as the solid-state imaging device 15. The imaging signal is converted into image data by an imaging signal processing section 27 based on a command from a control section 29, and appropriate image processing is performed for the image data. The control section 29 outputs the image data output from the imaging signal processing section 27, as an image, to the monitor 40. The optical fiber 21 guides light emitted from a light source section 31, which will be described later, of the light source device 20 to the tip of the insertion portion 13. The light source device 20 is configured to include the light source section 31, the optical fiber 21, and the illumination optical member 19.

Figure 2:
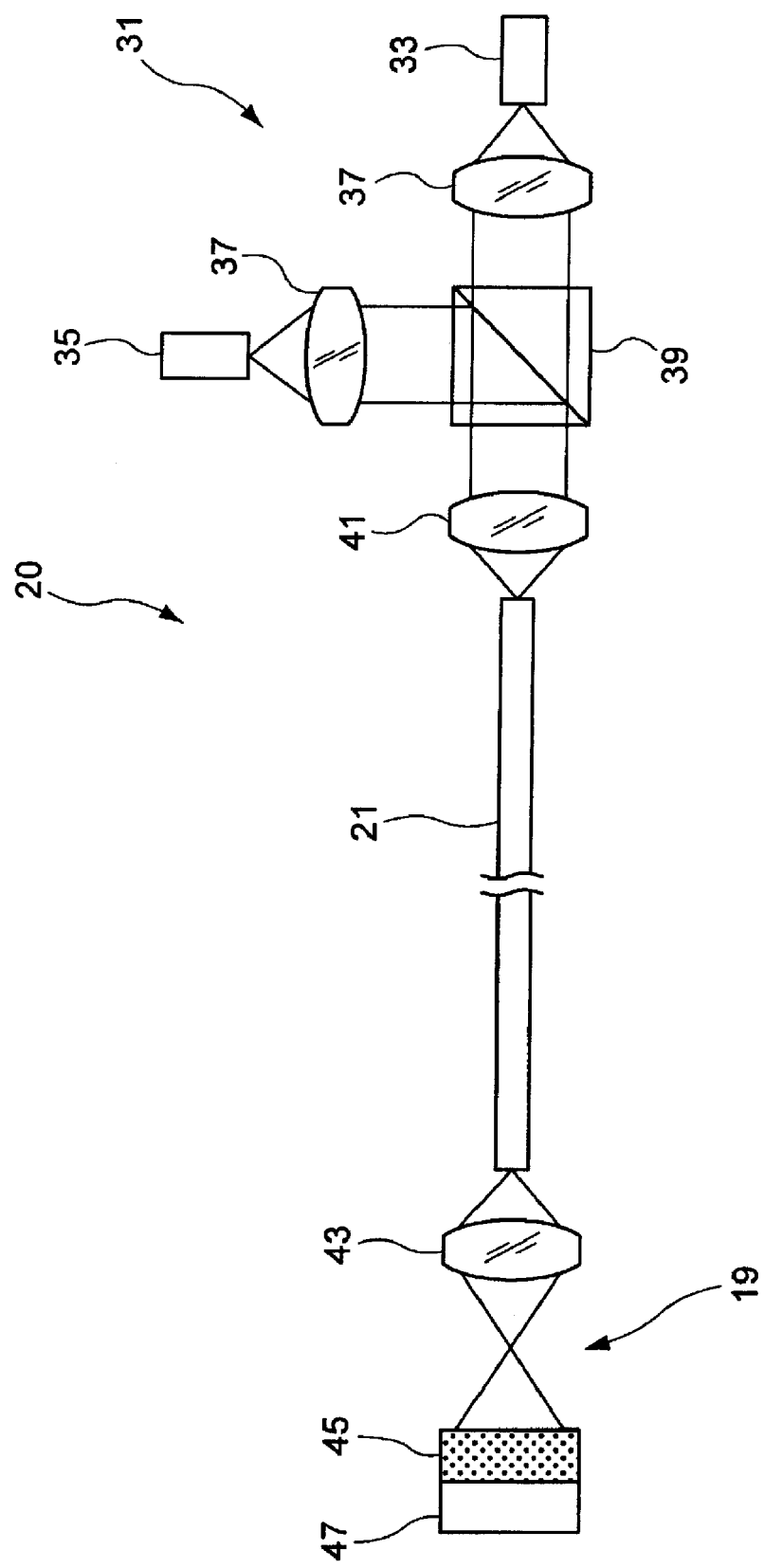
FIG. 2 is a view illustrating the configuration of an optical system of a light source device for use in the endoscope apparatus shown in FIG. 1.

Next, an example of the configuration of the light source section 31 will be described. FIG. 2 is a view illustrating the configuration of an optical system of the light source device used in the endoscope apparatus shown in FIG. 1. The light source device 20 has: a blue laser light source 33 (an example of a first light source) having a center wavelength of 445 nm; an infrared laser light source 35 (an example of second light source) having a center wavelength of 980 nm; collimator lenses 37, 37 which collimate laser beams from the blue laser light source 33 and the infrared laser light source 35; a polarization beam splitter 39 which is an optical coupling unit that polarize and couples two laser beams; a condensing lens 41 which condenses laser beams coupled on the same optical axis by the polarization beam splitter 39; and the optical fiber 21.

The blue laser light source 33 is a broad area type InGaN laser diode. Moreover, an InGaNAs laser diode or a GaNAs laser diode may also be used.

The infrared laser light source 35 is a broad area type InGaAs semiconductor laser which emits an infrared ray that is invisible light.

A laser beam from the blue laser light source 33 and a laser beam from the infrared laser light source 35 are coupled by the polarization beam splitter 39 and are then input to the optical fiber 21 by the condensing lens 41. The optical fiber 21 allows the input laser beam to propagate up to the tip of the insertion portion 13 (refer to FIG. 1) of the endoscope 10.

On the other hand, on the light emission side of the optical fiber 21, a condensing lens 43 which constitutes the illumination optical member 19 is disposed, and a first wavelength conversion member 45 and a second wavelength conversion member 47 which are integrated are also disposed. Moreover, although not shown, on the tip surface of the insertion portion 13 of the endoscope 10, the illumination optical member 19 is disposed with a cover glass or a lens interposed therebetween. The first wavelength conversion member 45 has a phosphor including plural types of phosphors which absorb and are excited by a part of the laser beam from the blue laser light source 33 so as to emit light of green to yellow. Then, the laser beam from the blue laser light source 33 and the excitation light of green to yellow converted from the laser beams are mixed to generate white light.

The second wavelength conversion member 47 is made of an up-conversion material which absorbs and is excited by the laser beam from the infrared laser light source 35 so as to emit green light. An example of the up-conversion material includes oxide-fluoride-based crystallized glass. For example, high-efficiency infrared/visible conversion transparent glass ceramic or transparent body crystal described in JP Hei.7-69673 A (corresponding to U.S. Pat. Nos. 5,420,080 and 5,545,595) and JP Hei.7-97572 A (corresponding to U.S. Pat. No. 5,439,616) may be used as the second wavelength conversion member 47. Moreover, a rare-earth element may also be added to the oxide-fluoride-based crystallized glass as a base material. It is assumed that an added rare-earth element is erbium (Er), for example. In this case, when it is excited by infrared light of a broad band semiconductor laser having a wavelength of 808 nm, emitted color light can be freely controlled, for example, according to the concentration of Er. For example, at 0.1 to 1 mol %, green light is emitted. As the concentration increases, light is emitted gradually on the long wavelength side. Yellow light can be emitted when the concentration of Er exceeds 2.0 mol %, and red light can be emitted at 5.0 mol %. In addition to those described above, the emission efficiency of green light may also be increased by adding Er and an yttrium (Y) to the oxide-fluoride-based crystallized glass. Alternatively, only Er may be added.

The second wavelength conversion member 47 is made of, for example, a $Yb^{3+}$—$Er^{3+}$-based up-conversion phosphor, and the basic composition is $SiO_2(GeO_2)$—$PbF_2$—$ReF_3$(Re: Yb, Er) of three component system. As an example, 'YAG-LASS (product name)' of Sumita Optical Glass, Inc. is available. The composition is $22SiO_2$-$10GeO_2$-$15AlO_{1.5}$-$3TiO_2$-$39PbF_2$-$10YbF_3$-$1ErF_3$ in mol %.

With the above-described configuration, each laser beam emitted from the optical fiber 21 is irradiated to the first wavelength conversion member 45, and the first wavelength conversion member 45 absorbs a part of blue laser beam from the blue laser light source 33, performs wavelength conversion of the absorbed blue laser beams, and is excited to emit light (light of green to yellow) which has a longer wavelength than the blue laser beam. In addition, the other part of the blue laser beam and the infrared laser beam of the infrared laser light source 35 are transmitted through the first wavelength conversion member 45 without being absorbed by the first wavelength conversion member 45, and are then incident on the second wavelength conversion member 47 together with the excitation light of the first wavelength conversion member 45. The second wavelength conversion member 47 absorbs a part of or all of the infrared laser beams and is excited to emit narrowband green light. As a result, white light obtained by mixing of (i) the blue laser beams, (ii) the green to yellow light emitted by excitation of the first wavelength conversion member 45 and (iii) the narrowband green light emitted by excitation of the second wavelength conversion member 47 are emitted frontward on the optical path. In addition, the first wavelength conversion member 45 and the second wavelength conversion member 47 may be disposed separately without being integrated. Moreover, one block in which materials having respective functions are finely mixed and arranged may be advantageous in reducing the space.

Furthermore, as compared with the case where a laser beam is emitted as illumination as it is, since the green light obtained by excitation by the infrared light is irradiated, it hardly occurs that a noise is superimposed on a captured image or flickering occurs on a moving image due to speckle (interference) by a laser beam. In addition, if a selective reflection film for the infrared light for suppressing emission of unnecessary infrared light is provided on a converted light emission side of the second wavelength conversion member 47 located at the tip, the infrared light is incident again on the second wavelength conversion member 47. Thereby, emission of green light can be more intensified.

Moreover, if the second wavelength conversion member 47 located at the tip is divided into two semicircular parts and if the Er density in one of the parts is set to 0.5% and the Er density in the other part is set to 5%, narrow-band green light and red light can be emitted simultaneously by infrared light. In this case, narrowband green light and red light can be emitted simultaneously. Alternatively, such light components may be emitted separately.

Figure 3:
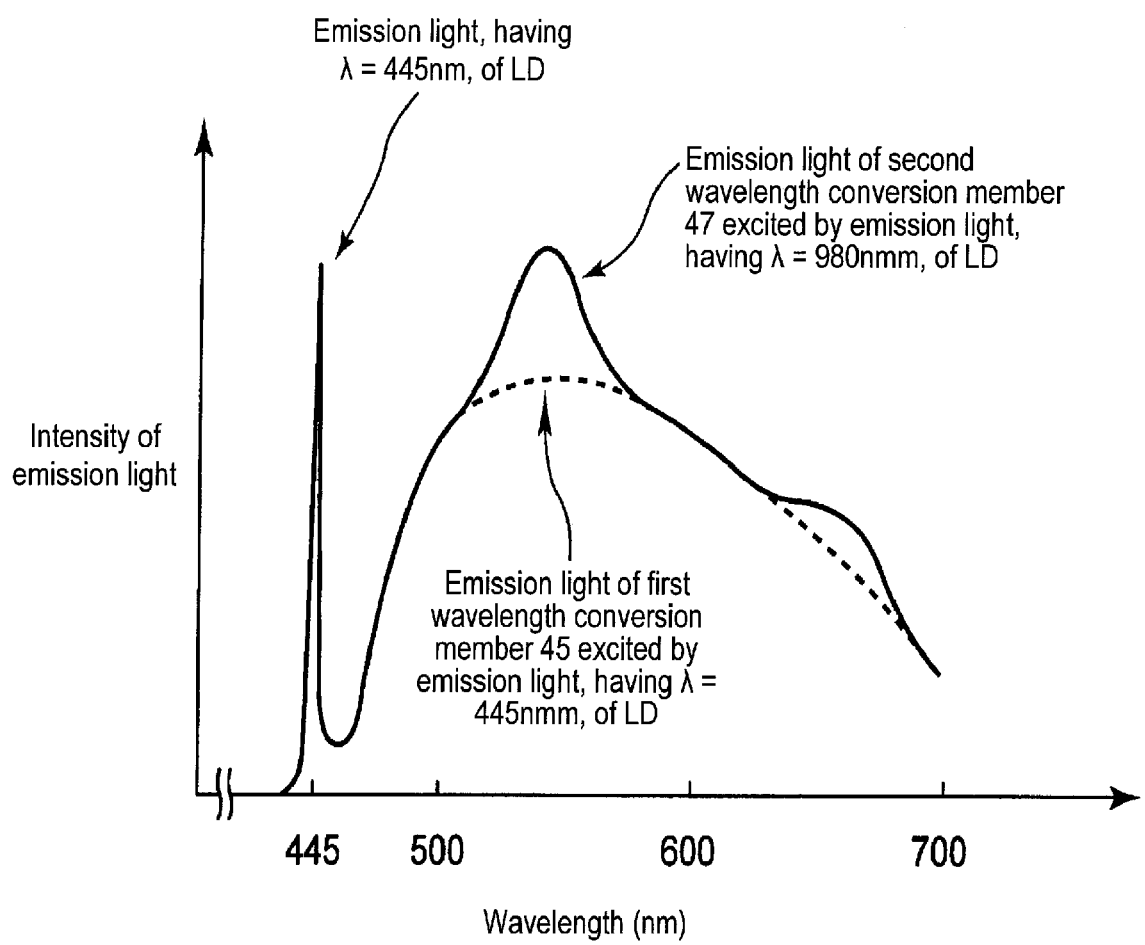
FIG. 3 is a graph illustrating the spectrum distribution of light after laser beams mixed and emitted from light source sections are wavelength-converted by first and second wavelength conversion members.

FIG. 3 is a graph illustrating the spectrum distribution of light after the laser beams coupled and emitted from the light source section 31 is wavelength-converted by the first wavelength conversion member 45 and the second wavelength conversion member 47. The laser beam from the blue laser light source 33 is represented by an emission line having a center wavelength of 445 nm Light emitted from the first wavelength conversion member 45 excited by the laser beam increases the intensity of the emission light in a wavelength band of approximately 450 nm to 700 nm. White light is formed by light within this wavelength band and a blue laser beam. In addition, light emitted from the second wavelength conversion member 47 excited by the infrared laser beam from the infrared laser light source 35 superimposes the intensity of the emission light in a narrow wavelength band of about 530 to 570 nm.

Figure 4:
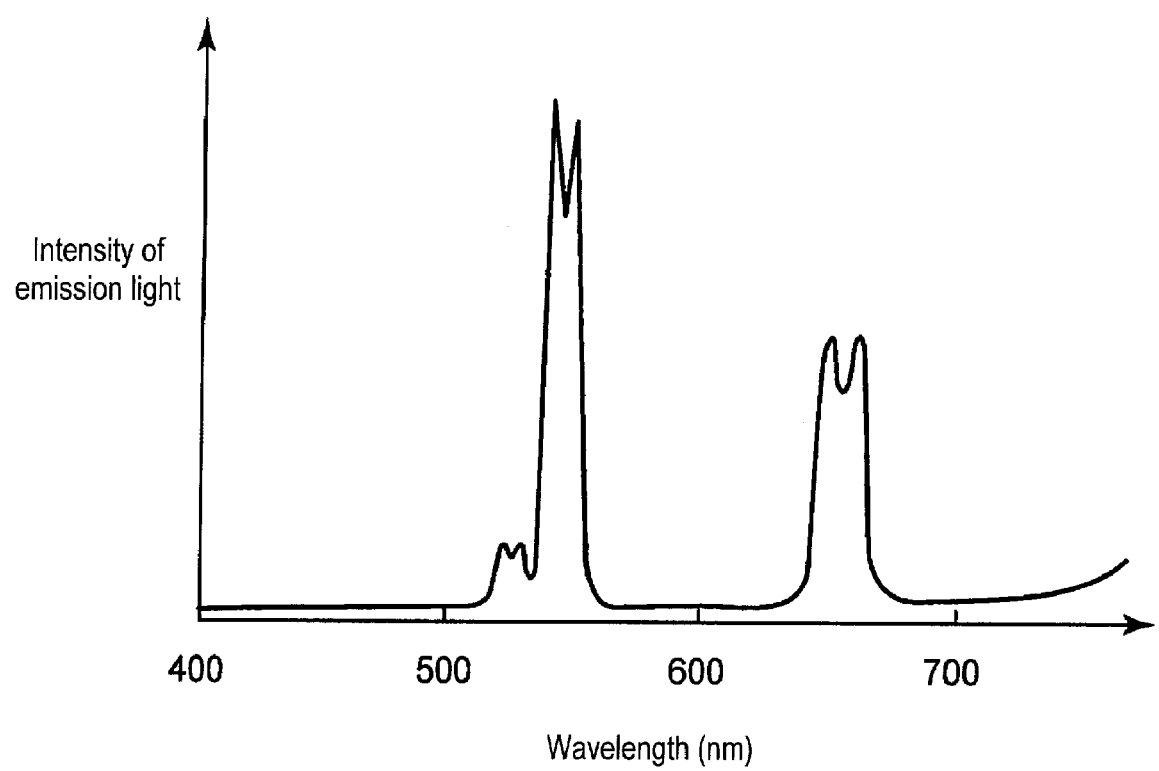
FIG. 4 is an emission spectrum when a second wavelength conversion member is excited by an infrared laser beam having a center wavelength of 950 nm.

FIG. 4 is an emission spectrum when the second wavelength conversion member 47 is excited by an infrared laser beam having a center wavelength of 950 nm. Light emitted in a wavelength band of 550 nm is green light emitted by $Er^{3+}$, and light emitted in a wavelength band of 660 nm is red light emitted by $Er^{3+}$. That is, the green emitted light increases the emission intensity near 550 nm in FIG. 3. In addition, although the red light generated from the second wavelength conversion member 47 is emitted together with green light, a green light component and a red light component can be easily separated by using a color filter provided in the solid-state imaging device 15, for example, by detecting only a green light component with the solid-state imaging device 15. Accordingly, a problem of color mixture does not occur in subsequent signal processing.

Next, a use example of the endoscope apparatus 100 when the light source device 20 having the above-described configuration is built into the endoscope 10 will be described. As shown in FIG. 1, in the endoscope apparatus 100, the insertion portion 13 of the endoscope 10 is inserted into the body cavity, illumination light is irradiated through the illumination optical member 19 from the tip of the insertion portion 13, and the reflected light is imaged through the imaging lens 17 in the solid-state imaging device 15. An imaging signal obtained by the imaging is output to the monitor 40 after being subjected to the appropriate image processing by the imaging signal processing section 27. Or, the imaging signal is stored in a recording medium.

In case of imaging using such a solid-state imaging device 15, at the time of normal endoscopic diagnosis in which observation is made by irradiating white illumination light within the body cavity, the control section 29 turns on an output of a laser beam from the blue laser light source 33 and turns off the infrared laser light source 35 or blocks the output of the infrared laser light source 35 with a shutter. In this case, irradiated is white illumination light, which is generated by the laser beam from the blue laser light source 33 and the light emitted by excitation of the first wavelength conversion member 45. Moreover, when performing spectral diagnostics with the endoscope apparatus 100, the control section 29 turns on outputs of the blue laser light source 33 and the infrared laser light source 35 simultaneously so that illumination light having the emission spectrum shown in FIG. 3 is irradiated. Furthermore, the light irradiation may also be performed while making a proper adjustment of turning on only the infrared laser light source 35 or turning on the outputs of the blue laser light source 33 and the infrared laser light source 35 simultaneously in a state where the output of the blue laser light source 33 is reduced.

Also, laser beams from the infrared laser light source 35, which generates light in a specific narrow visible wavelength band, are invisible light. Therefore, the color balance of illumination light emitted is not affected even if a part of the laser beams are transmitted through the second wavelength conversion member 47 without all of the laser beams from the infrared laser light source 35 being wavelength-converted by the second wavelength conversion member 47. Accordingly, the diagnostic precision of the endoscope can be maintained high without causing a color change in an observed image within the body cavity. In addition, the infrared laser beams from the infrared laser light source 35 are hardly absorbed by the first wavelength conversion member 45. Accordingly, since a drop in light intensity is small, an illumination optical system with high light use efficiency can be built.

[Second Embodiment]

Figure 5:
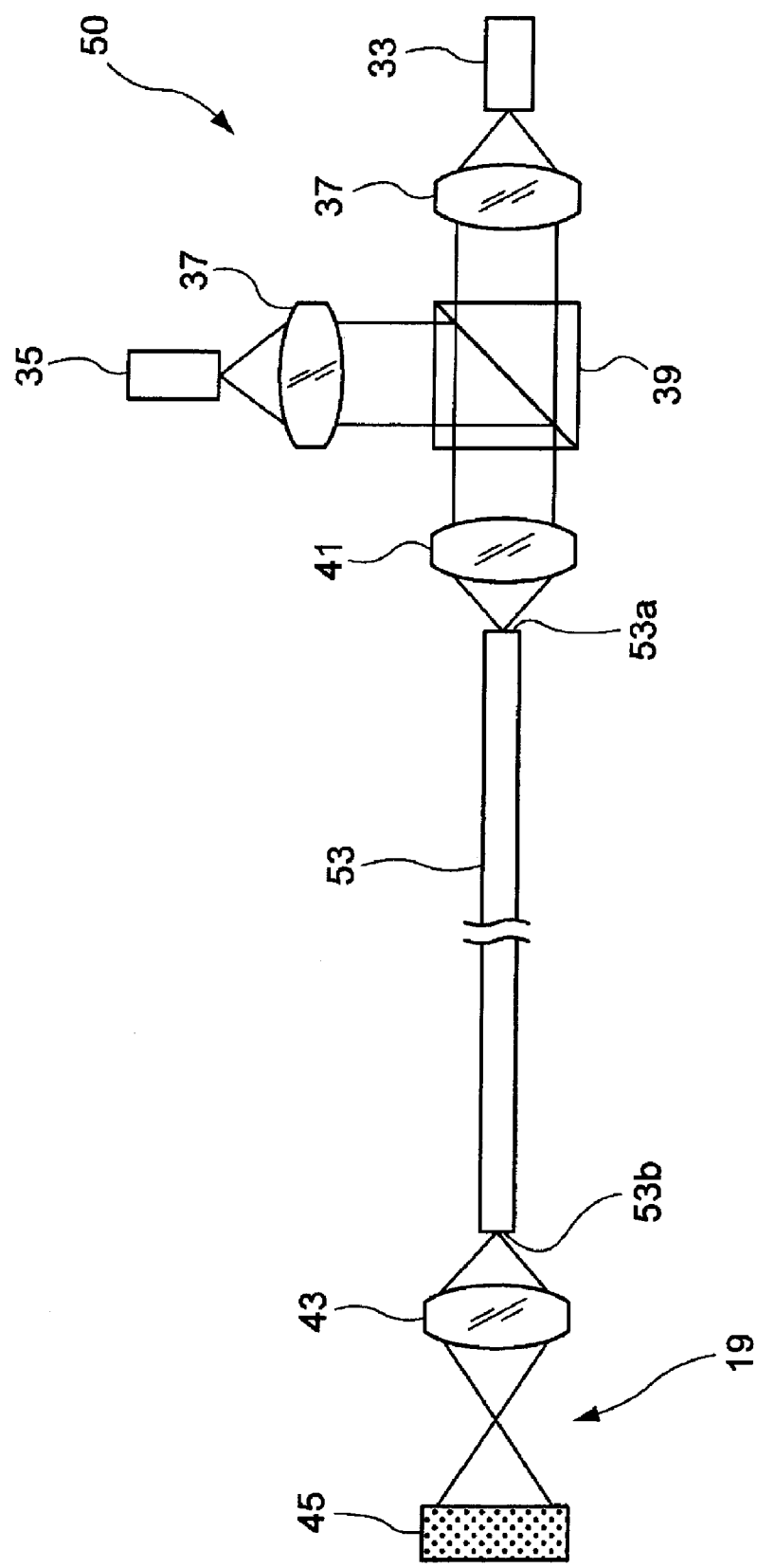
FIG. 5 is a configuration view of an optical system of a light source device, according to a second embodiment, for use in the endoscope apparatus shown in FIG. 1.

Next, a second embodiment in which the second wavelength conversion member 47 of the light source device 20 is provided within an optical fiber will be described. FIG. 5 is a configuration view of an optical system illustrating another example of a light source device used in the endoscope apparatus of FIG. 1. Here, description on members which are the same as those in FIG. 2 will be omitted or simplified with the same reference numerals being assigned thereto. The configuration of a light source device 50 is the same as the above-described configuration except that a material of the second wavelength conversion member 47 is contained in a light guiding material of the entire optical fiber 53 or a part of the optical fiber 53 instead of providing a block of the second wavelength conversion member 47 on the light emission side of the optical fiber 53.

Figure 6:
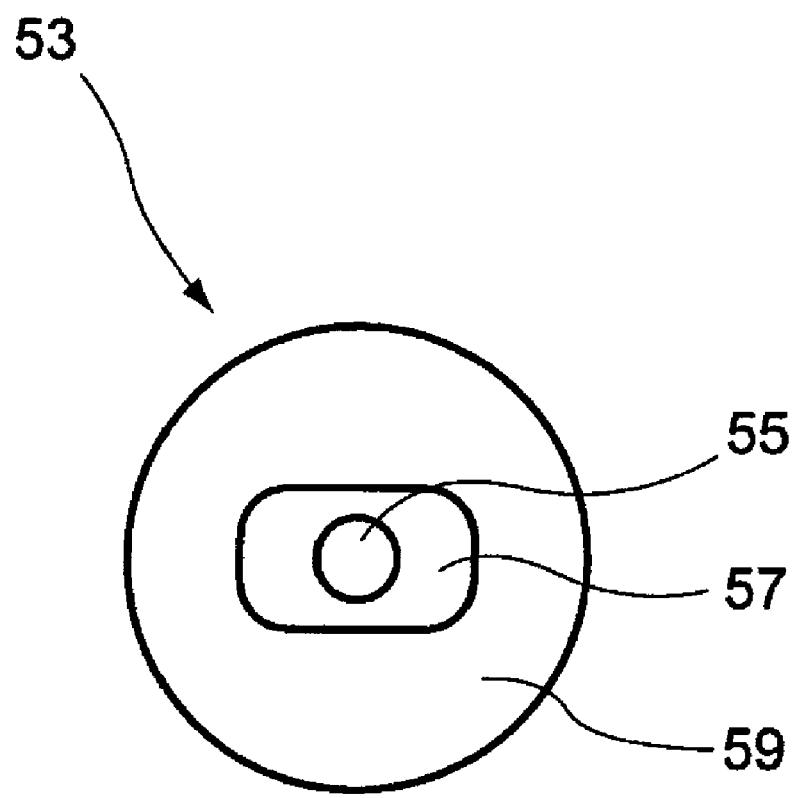
FIG. 6 is a section view of an optical fiber shown in FIG. 5.

FIG. 6 shows a section view of the optical fiber 53 shown in FIG. 5. The optical fiber 53 is configured to include a core 55 having a circular cross section, a first cladding 57 which is disposed outside the core 55 and has an approximately rectangular section, and a second cladding 59 which is disposed outside the first cladding 57 and has a circular section. The core 55 is made of a Zr-based fluoride glass doped with $Pr^{3+}$, for example, ZBLANP ($ZrF_4$—$BaF_2$-$LaF_3$—$AlF_3$—$AlF_3$—$NaF$—$PbF_2$). The first cladding 57 is made of ZBLAN ($ZrF_4$—$BaF_2$—$LaF_3$—$AlF_3$—$NaF$) as an example, and the second cladding 59 is made of a polymer as an example.

In addition, the core 55 may be formed using not only the ZBLANP but also ZBLAN or In/Ga-based fluoride glass, for example, IGPZCL, that is, $(InF_3$—$GaF_3$—$LaF_3)$-$(PbF_2$—$ZnF_2)$—$CdF$.

With the above-described configuration, a laser beam having a wavelength of 445 nm and a laser beam having a wavelength of 950 nm, which are condensed by the condensing lens 41, are input to the first cladding 57 of the optical fiber 53 and propagate therethrough in a waveguide mode. That is, the first cladding 57 acts as a core for a laser beam which is excitation light.

A laser beam also passes through a portion of the core 55 while propagating as described above. In the core 55, $Pr^{3+}$ is excited by the incident laser beam, thereby generating fluorescent light having a wavelength of 491 nm. The fluorescent light propagates through the core 55 in the waveguide mode and is emitted from an emission end 53b of the optical fiber 53 forward on the optical path.

In addition, the fluorescent light may also be laser-oscillated and emitted. For example, in the core 55 made of ZBLANP, fluorescent light having a wavelength of 520 nm by transition of 3P1->3H5, fluorescent light having a wavelength of 605 nm by transition of 3P0->3F2, and fluorescent light having a wavelength of 635 nm by transition of 3P0->3F3 may be generated in addition to the above fluorescent light. Therefore, an incidence end 53a of the optical fiber 53 is coated such that HR (high reflection) is realized for the wavelength of 491 nm and AR (antireflection) is realized for the wavelengths of 520 nm, 605 nm, and 635 nm and a wavelength of 950 nm causing excitation light, and the emission end 53b of the optical fiber 53 is coated to allow only 1% of light having the wavelength of 491 nm to be transmitted therethrough.

With such coating, the fluorescent light having the wavelength of 491 nm resonates between both the ends 53a and 53b of the optical fiber 53 to cause laser oscillation. Then, a blue-green laser beam having a wavelength of 491 nm obtained as described above can be emitted from the emission end 53b of the optical fiber 53 frontward on the optical path.

Moreover in this example, a laser beam having a wavelength of 445 nm propagates through the core 55 in a single mode, while a laser beam having a wavelength of 950 nm which is excitation light propagates through the first cladding 57 in a multimode. This makes it possible that a laser beam from the infrared laser light source 35 is input to the optical fiber 53 with high coupling efficiency.

In addition, since the sectional shape of the first cladding 57 is almost rectangular, the laser beam from the infrared laser light source 35 follows an irregular reflecting path within a cladding section. Accordingly, a probability of the laser beam being incident on the core 55 is increased. As a result, since high oscillation efficiency is secured, a high-output green-blue laser beam can be obtained.

With the above-described configuration, the illumination optical member 19 disposed at the tip of the insertion portion 13 of the endoscope 10 requires only the first wavelength conversion member 45. As a result, the insertion portion 13 of the endoscope 10 can be made compact. In addition, a material of the second wavelength conversion member 47 may be disposed at any position so long as its position is anterior to the incidence side 53a of the optical fiber 53 on the optical path.

[Third Embodiment]

Figure 7:
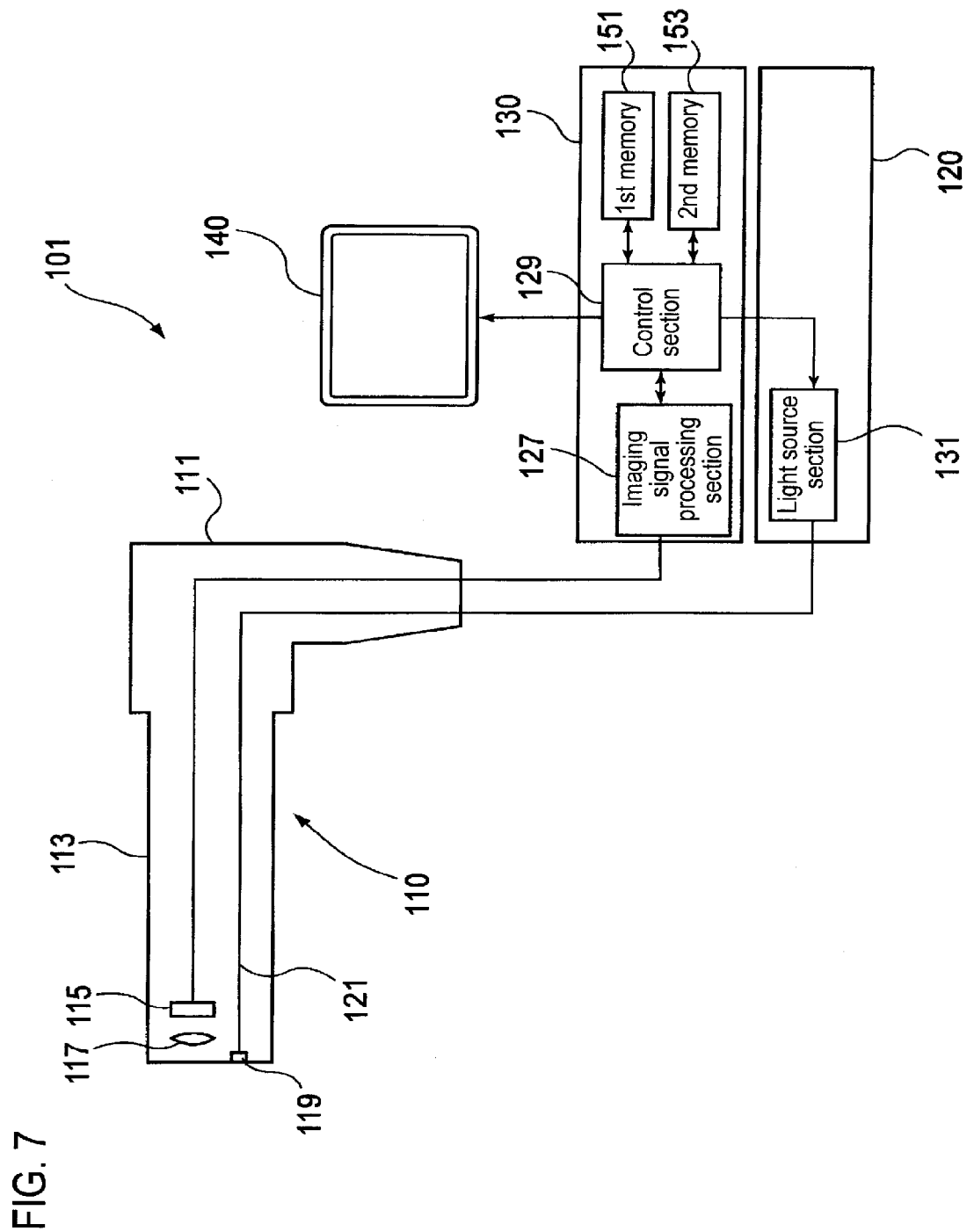
FIG. 7 is a view illustrating the conceptual configuration of an endoscope apparatus according to a third embodiment.

Hereinafter, a light source device according to a third embodiment, an endoscope apparatus using this light source device, and an image processing method will be described in detail with reference to the accompanying drawings. FIG. 7 is a view illustrating the conceptual configuration of the endoscope apparatus according to the third embodiment. An endoscope apparatus 101 is configured to mainly include an endoscope 110, a light source device 120, an image processing device 130, and a monitor 140. The endoscope 110 includes a main body operation portion 111 and an insertion portion 113 which is provided to be connected to the main body operation portion 111 and is inserted into a body to be inspected (body cavity). A solid-state imaging device 115 and an imaging lens 117 which constitute an imaging optical system are disposed in a tip portion of the insertion portion 113. Moreover, an illumination optical member 119, which constitutes an illumination optical system, and an optical fiber 121 connected to the illumination optical member 119 are disposed near the imaging optical system. The optical fiber 121 is connected to the light source device 120, which will be described in detail later. An imaging signal from the solid-state imaging device 115 is input to the image processing device 130.

An imaging device, such as a CCD or a CMOS, is used as the solid-state imaging device 115. The imaging signal is converted into image data by an imaging signal processing section 127 based on a command from a control section 129 and appropriate image processing is performed for the image data. The control section 129 outputs the image data output from the imaging signal processing section 127, as an image, to the monitor 140 which is an example of an imaged image display unit. Moreover, a first memory 151 and a second memory 152 for storing imaging signals are connected to the control section 129. The first and second memories 151 and 152 will be described later. The optical fiber 121 guides light emitted from a light source section 131, which will be described later, of the light source device 120 to the tip of the insertion portion 113. The light source device 120 is configured to include the light source section 131, the optical fiber 121, and the illumination optical member 119.

Figure 8:
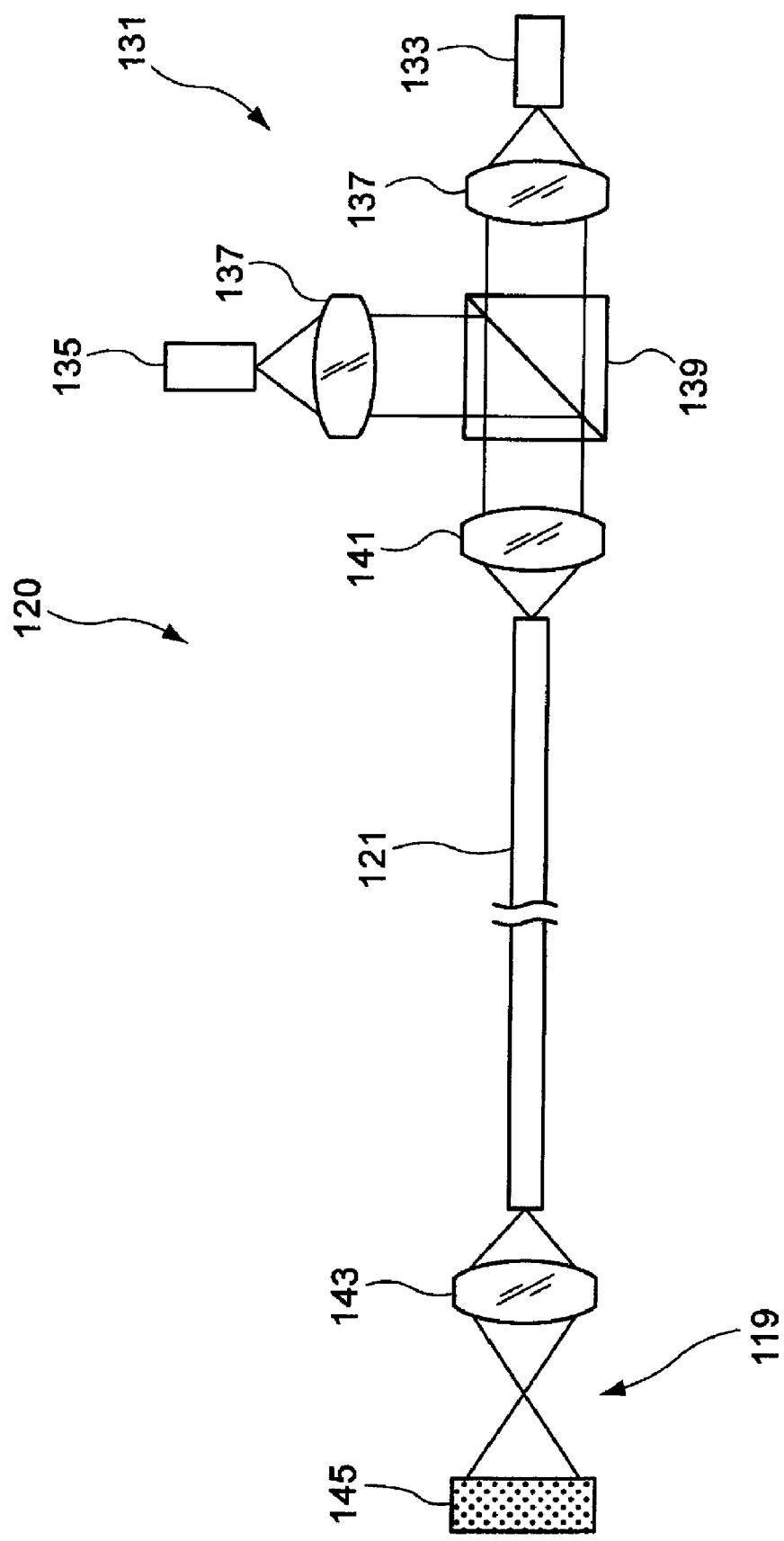
FIG. 8 is a view illustrating the configuration of an optical system of a light source device for use in the endoscope apparatus shown in FIG. 7.

Next, an example of the configuration of the light source section 131 will be described. FIG. 8 is a view illustrating the configuration of an optical system of the light source device used in the endoscope apparatus shown in FIG. 7. The light source device 120 has: a blue laser light source 133 (an example of a first light source) having a center wavelength of 445 nm; a near-ultraviolet laser light source 135 (an example of a second light source) having a center wavelength of 375 nm; collimator lenses 137, 137 which collimate laser beams from the blue laser light source 133 and the near-ultraviolet laser light source 135; a polarization beam splitter 139 which is an optical coupling unit that polarizes and couples two laser beams; a condensing lens 141 which condenses laser beams coupled on the same optical axis by the polarization beam splitter 139; and the optical fiber 121. In addition, the control section 129 functions as a control unit that controls emission of laser beams from the blue laser light source 133 and the near-ultraviolet laser light source 135.

The blue laser light source 133 is a broad area type InGaN laser diode.

The near-ultraviolet laser light source 135 is a broad area type InGaN semiconductor laser which emits a near-ultraviolet ray that is invisible light. In addition, although a laser which emits a near-ultraviolet ray is described herein, a purple laser having a center wavelength of 405 nm may be used, or a light source which emits purple to near-ultraviolet laser light may be used.

The laser beam from the blue laser light source 133 and the laser beam from the near-ultraviolet laser light source 135 are coupled by the polarization beam splitter 139 and are then input to the optical fiber 121 by the condensing lens 141. The optical fiber 121 allows the input laser beam to propagate up to the tip of the insertion portion 113 of the endoscope 110 (see FIG. 7).

On the other hand, on the light emission side of the optical fiber 121, a condensing lens 143 which constitutes the illumination optical member 119 is disposed, and a wavelength conversion member 145 in which first and second wavelength conversion members are integrated is disposed. The wavelength conversion member 145 is an integrated block in which plural types of phosphors are distributed. Moreover, although not shown, on the tip surface of the insertion portion 113 of the endoscope 110, the illumination optical member 119 is disposed with a cover glass or a lens interposed therebetween. The first wavelength conversion member which constitutes the wavelength conversion member 145 is configured to include plural types of phosphors (for example, a YAG-based phosphor or a phosphor including BAM ($BaMgAl_{10}O_{37}$)) which absorb a part of the laser beam from the blue laser light source 133 and are excited to emit light of green to yellow. Then, the laser beam from the blue laser light source 133 and the excitation light of green to yellow converted from the laser beam are mixed to generate white light.

The second wavelength conversion member which also constitutes the wavelength conversion member 145 is made of a down-conversion material which absorbs the laser beam from the near-ultraviolet laser light source 135 and is excited to emit light of green. As the down-conversion material, for example, $LiTbW_2O_8$ which is a green phosphor (see Tsutomu Odaki, "Phosphor for White LED", IEICE Technical Research Report ED2005-20, CFM2005-28, SDM2005-28, pp. 69-74 (2005-05), and the like), beta SiALON (β-SiA-LON: Eu) blue phosphor (see Naoto Hirosaki, Xie Rong Jun and Ken Sakuma, "New SiALON phosphors and white LEDs", Transactions of JSAP, Vol. 74, No. 11, pp. 1449-1452 (2005), or Hajime Yamamoto, School of Bionics, Tokyo University of Technology, Transactions of JSAP, Vol. 76, No. 3, p. 241 (2007)) may be used. β-SiALON is crystal expressed as composition of $Si_6-zAl_2O_2N_8-z$ (z is solid soluble amount) in which aluminum and acid are solid-dissolved in β-type silicon nitride crystal. Here, both $LiTbW_2O_8$ and β-SiALON are mixed as the second wavelength conversion member. In addition, the configuration in which both phosphors may be stacked in the layer shape may also be adopted. In the wavelength conversion member 145, the phosphors included in the first and second wavelength conversion members are randomly distributed to be formed as an integrated body. In addition to randomly distributing the phosphors, a proper modification may be made according to a phosphor material, for example, by forming the first and second wavelength conversion members as fine blocks and then bonding the fine blocks to each other or adopting a laminated structure in which the fine blocks are stacked in the layer shape.

With the above-described configuration, each laser beam emitted from the optical fiber 121 is irradiated to the wavelength conversion member 145, and the wavelength conversion member 145 absorbs a part of the blue laser beam from the blue laser light source 133 by the first wavelength conversion member and is excited to emit light (light of green to yellow) which has a longer wavelength than the blue laser beam. In addition, the wavelength conversion member 145 absorbs a part of or all of the near-ultraviolet laser beam from the near-ultraviolet laser light source 135 and is excited to emit narrowband green light and blue light. As a result, white light obtained by mixing of the blue laser beam, the green to yellow light emitted by excitation of the first wavelength conversion member and the narrowband green light and blue light emitted by excitation of the second wavelength conversion member is emitted forward on the optical path. Each of the wavelength conversion members is selected so that a blue laser beam is transmitted through the second wavelength conversion member without being absorbed by the second wavelength conversion member and that a near-ultraviolet laser beam is transmitted through the first wavelength conversion member without being absorbed by the first wavelength conversion member.

As compared with the case where a laser beam is emitted as illumination as it is, since the green and blue light obtained by excitation by the near ultraviolet light is irradiated, it hardly occurs that a noise is superimposed on a captured image or flickering occurs on a moving image due to speckle (interference) by a laser beam. In addition, if a selective reflection film for near-ultraviolet light for suppressing emission of unnecessary near-ultraviolet light is provided on a converted light emission side of the wavelength conversion member 145, the near-ultraviolet light is incident again on the wavelength conversion member 145. Accordingly, in this case, emission of green light and narrowband blue light can be more intensified. Moreover, in case of using a purple laser instead of near-ultraviolet light, it is preferable to provide a selective reflection film of purple light similarly.

Figure 9:
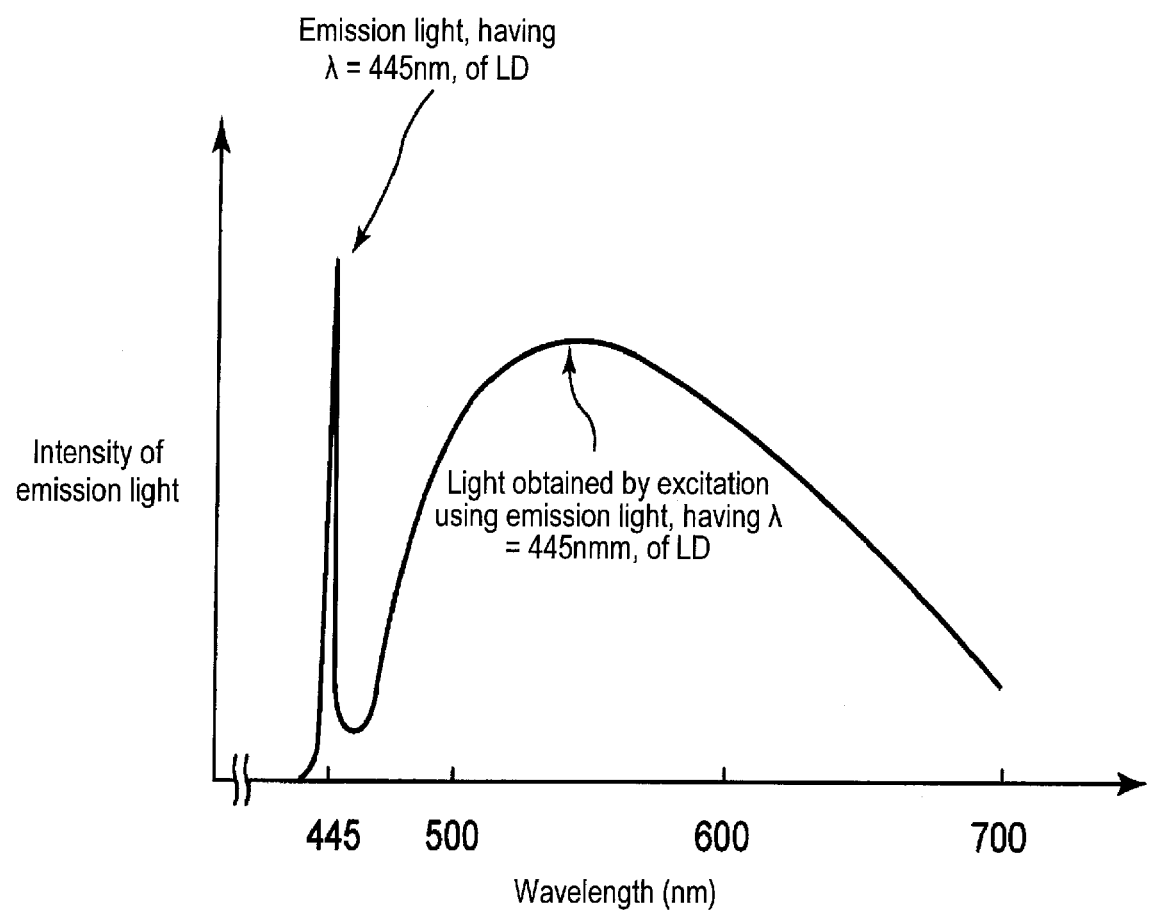
FIG. 9 is a graph illustrating the spectrum distribution of light after a blue laser beam is wavelength-converted by the first wavelength conversion member.

FIG. 9 is a graph illustrating the spectrum distribution of light after the blue laser beam is wavelength-converted by the first wavelength conversion member. The blue laser beam from the blue laser light source 133 is represented by an emission line having a center wavelength of 445 nm. Light emitted from the first wavelength conversion member excited by the laser beam increases the emission intensity in a wavelength band of approximately 450 nm to 700 nm White light is formed by the light within this wavelength band and the blue laser beam.

Figure 10:
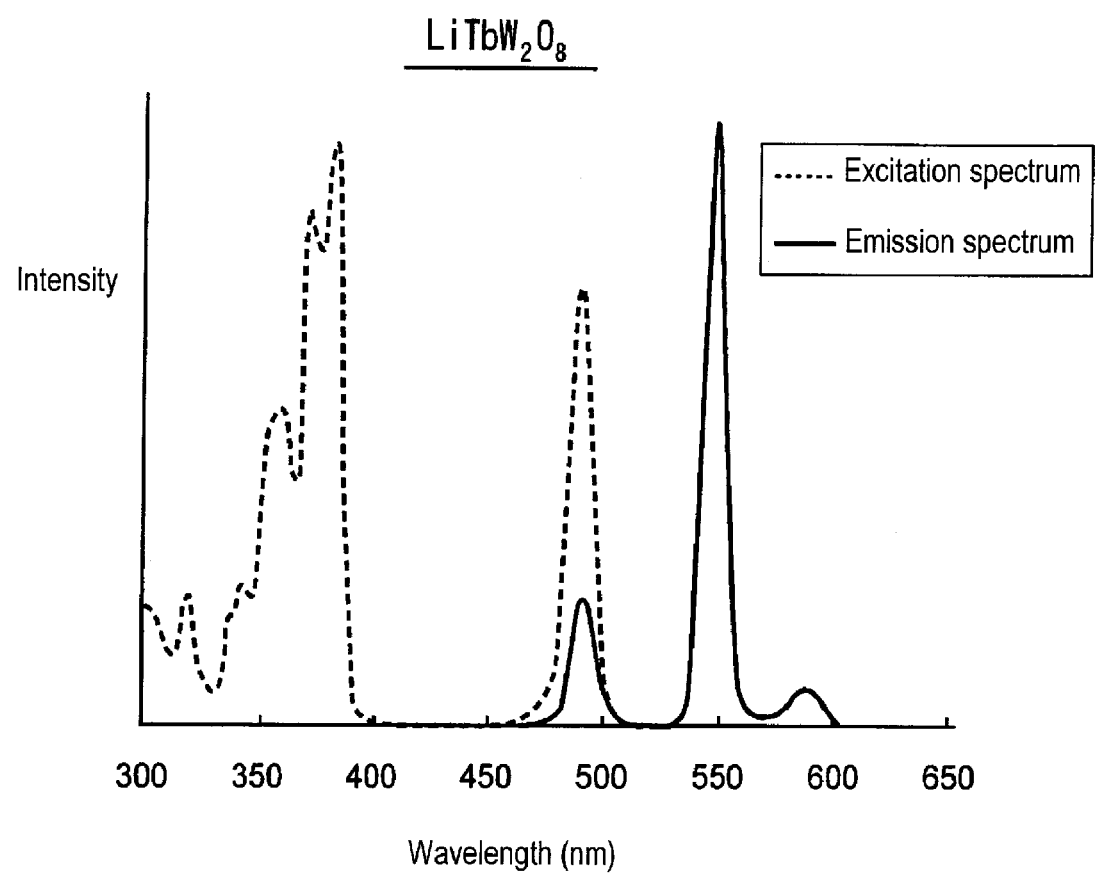
FIG. 10 is a graph illustrating excitation spectrum and emission spectrum of $LiTbW_2O_8$ used as the second wavelength conversion member.

FIG. 10 is an excitation spectrum and an emission spectrum of $LiTbW_2O_8$ used as the second wavelength conversion member. In the case of $LiTbW_2O_8$, a sharp excitation band exists near a wavelength of 375 nm, so that a near-ultraviolet laser beam having a center wavelength of 375 nm can be efficiently wavelength-converted. In addition, light which has a wavelength of 544 nm as a center wavelength and which is emitted by transition of 5D4->7F5 of $Tb^{3+}$ ion becomes high-intensity light having a narrow wavelength band, that is, having about 20 nm in full width at half maximum.

Figure 11:
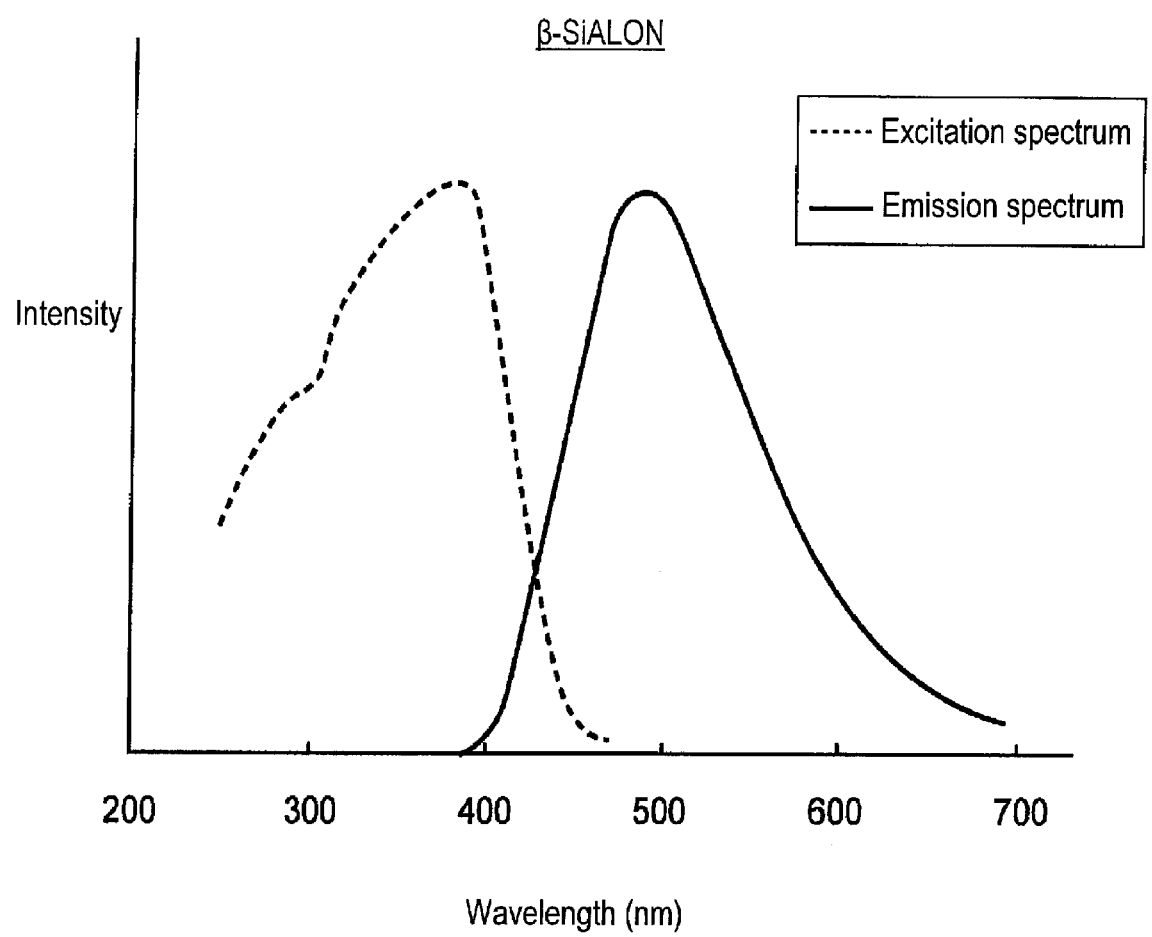
FIG. 11 is a graph illustrating excitation spectrum and emission spectrum of β-SiALON used as the second wavelength conversion member.

FIG. 11 is an excitation spectrum and an emission spectrum of β-SiALON similarly used as the second wavelength conversion member. The β-SiALON is a phosphor which absorbs light having a wavelength of 350 to 430 nm to emit light corresponding to blue to blue-green of 450 to 520 nm. The β-SiALON can realize wavelength conversion of a near-ultraviolet laser beam having a center wavelength of 375 nm efficiently. Accordingly, the light source device 120 can selectively emit the white light shown in FIG. 8, the green light having the center wavelength of 544 nm shown in FIG. 10, or the blue to blue-green light having the wavelength of 450 to 520 nm shown in FIG. 11. In addition, although green light, blue light, and emitted light in other wavelength bands generated from the second wavelength conversion member are emitted simultaneously, a green light component and other light components can be easily separated by using a color filter provided in the solid-state imaging device 115, for example, by detecting only a green light component with the solid-state imaging device 115. Moreover, a blue light component may be separated similarly. Accordingly, a problem of color mixture does not occur in subsequent signal processing.

Next, a use example of the endoscope apparatus 101 when the light source device 120 having the above-described configuration is built into the endoscope 110 will be described.

As shown in FIG. 7, in the endoscope apparatus 101, the insertion portion 113 of the endoscope 110 is inserted into the body cavity, and illumination light is irradiated through the illumination optical member 119 from the tip of the insertion portion 113. The reflected light is imaged through the imaging lens 117 in the solid-state imaging device 115. An imaging signal obtained by the imaging is output to the monitor 140 after being subjected to the appropriate image processing by the imaging signal processing section 127. Or, the imaging signal is stored in a recording medium.

In case of imaging using this solid-state imaging device 115, at the time of normal endoscopic diagnosis in which observation is made by irradiating white illumination light within the body cavity, the control section 29 turns on an output of a laser beam from the blue laser light source 133 shown in FIG. 8 and turns off the near-ultraviolet laser light source 135 or blocks the output with a shutter. In this case, the white illumination light generated by the laser beam from the blue laser light source 133 and the light emitted by excitation of the first wavelength conversion member of the wavelength conversion member 145 is irradiated to the body to be inspected. Moreover, when spectral diagnostics is performed with the endoscope apparatus 101, the control section 29 turns on the output of the near-ultraviolet laser light source 135 so as to irradiate green light and blue light to a body to be inspected. Then, reflected light from the body to be inspected to which narrowband green light and blue light are irradiated simultaneously is imaged to generate a pseudo color image for spectral diagnostics. For example, the pseudo color image is generated by converting a green detection signal (reflected light component of narrowband green light) obtained by the imaging device 115 into a red color tone and converting a blue detection signal into blue and green color tones. With this pseudo color image, a surface microstructure (for example, a microstructure of a capillary vessel or a mucous membrane) of a surface layer of a body to be inspected can be clearly observed. For example, drawing of pit and surface blood vessel can be observed with the blue laser beam having the center wavelength of 445 nm, and flare or a fine blood vessel in a deep place can be observed with the narrowband green light by β-SiALON, having the center wavelength of 532 nm.

Here, a specific control example of spectral diagnostics will be described. FIG. 12A is a view illustrating plural frame images obtained in a time-series manner by imaging with the imaging optical system, and FIG. 12B is an explanatory view conceptually illustrating a state where these frame images are rearranged and displayed. Here, an observed image under illumination light of white light and an observed image under illumination light in a specific visible wavelength band (green, blue) are separately displayed on the monitor 140. As shown in FIG. 12A, the control section 129 controls the light source section 131 to emit the blue laser beam having the center wavelength of 445 nm in a first frame, thereby irradiating the white light to the body to be inspected. The imaging device 115 images the body to be inspected illuminated by the white light and stores the imaging signal in the first memory 151.

Then, the control section 129 controls the light source section 131 to emit the near-ultraviolet laser beam having the center wavelength of 375 nm in a second frame, thereby irradiating the green light and the blue light generated by the second wavelength conversion member to the body to be inspected. The imaging device 115 images the body to be inspected illuminated by the green light and the blue light and stores the imaging signal in the second memory 153.

Figure 13:
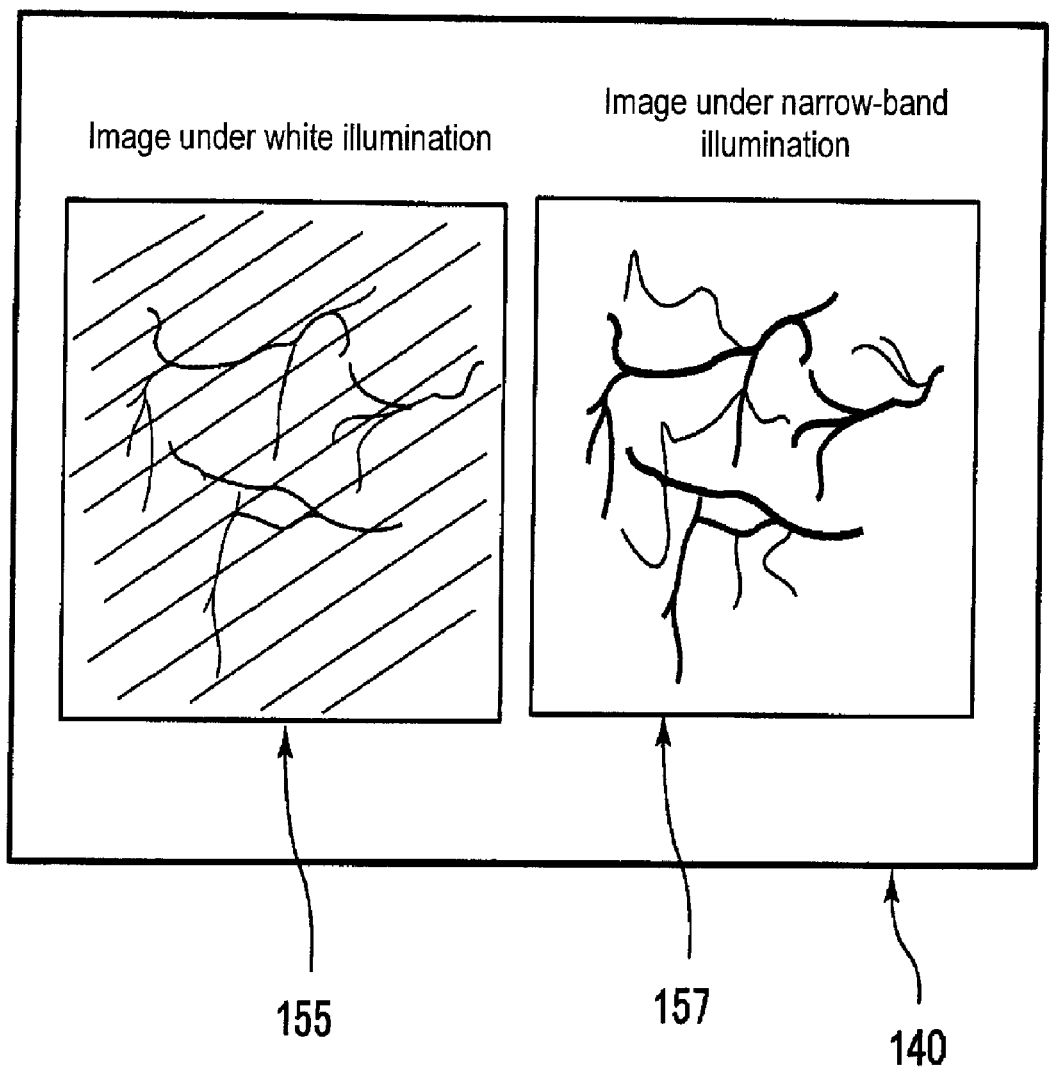
FIG. 13 is an explanatory view schematically illustrating a state where imaged signals stored in first and second memories are displayed in different display regions on a monitor, respectively.

Hereinafter, in the same manner as described above, processing of irradiation (illumination) of light, imaging, and storing of an imaging signal is repeatedly performed similarly to the first frame in a third frame (odd frame) and similarly to the second frame in a fourth frame (even frame). That is, the illumination of the white light and the illumination including light in the specific visible wavelength band are alternately switched every imaging frame of the imaging device 115. Then, as shown in FIG. 12B, the illumination images under the white light are accumulated in the first memory 151, and the images for narrowband diagnosis under the green light and the blue light are accumulated in the second memory 153. As image information based on these two types of imaging signals, the imaging signals stored in the first and second memories are displayed in different display regions 155 and 157 on the monitor, as shown in FIG. 13. Although the sizes of the display regions are set equal in the example shown in FIG. 13, the sizes may be set arbitrarily. For example, one of the display regions may be displayed larger than the other display region, or the other image may be displayed small within one display region.

Thus, by alternately imaging an image under the illumination of the white light and an image under the illumination including the light in the specific visible wavelength band, both the images can be acquired approximately at the same time. Accordingly, two types of image information can be simultaneously displayed in real time. In addition, since the observation position and the property of the observed portion can be understood simultaneously by displaying the imaged images side by side, the diagnostic precision based on the spectral diagnostics can be further improved.

Moreover, when imaging is performed by irradiating the light in the specific visible wavelength band, the combination of various light components is also available in addition to the combination of green excitation light of $LiTbW_2O_8$ and illumination light of blue excitation light by β-SiALON as described above. For example, an observed image when irradiating narrowband illumination light independently in a pseudo manner can be obtained with the laser beam from the blue laser light source 133. In this case, an image calculation process over frame images with different imaging timings is performed for plural frame images obtained in a time-series manner by imaging with the imaging optical system. That is, a frame image configured to include plural screens of detection color screens (screens of three primary colors of blue, green, and red) obtained by detection of light components with different specific wavelength bands is imaged multiple times, while light components from plural types of light sources are irradiated in synchronization with the imaging timing of each frame image and in different conditions. Assuming that an observed image when a body to be inspected is illuminated by the first light source is referred to as a first frame image and that an observed image when a body to be inspected is illuminated by the second light source is referred to as a second frame image, an observed image under light having a specific wavelength component from the light source is analytically obtained by repeatedly imaging the first and second frame images and performing the calculation process for brightness information of a specific detection color screen of the first frame image and brightness information of a specific detection color screen of the second frame image.

Figure 14:
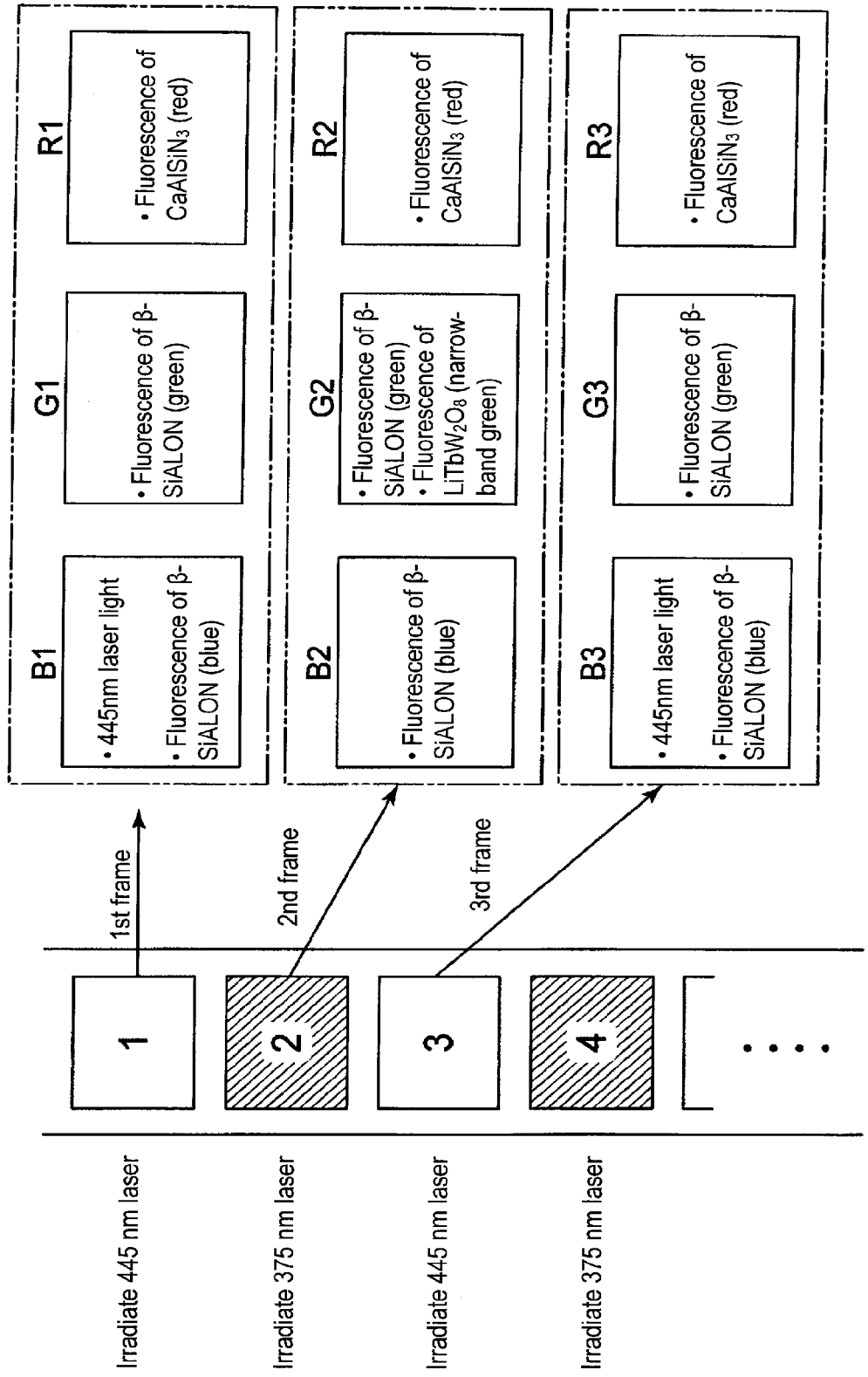
FIG. 14 is an explanatory view illustrating main light components, which are included in a screen of a specific detection color, for each frame image.
Figure 15:
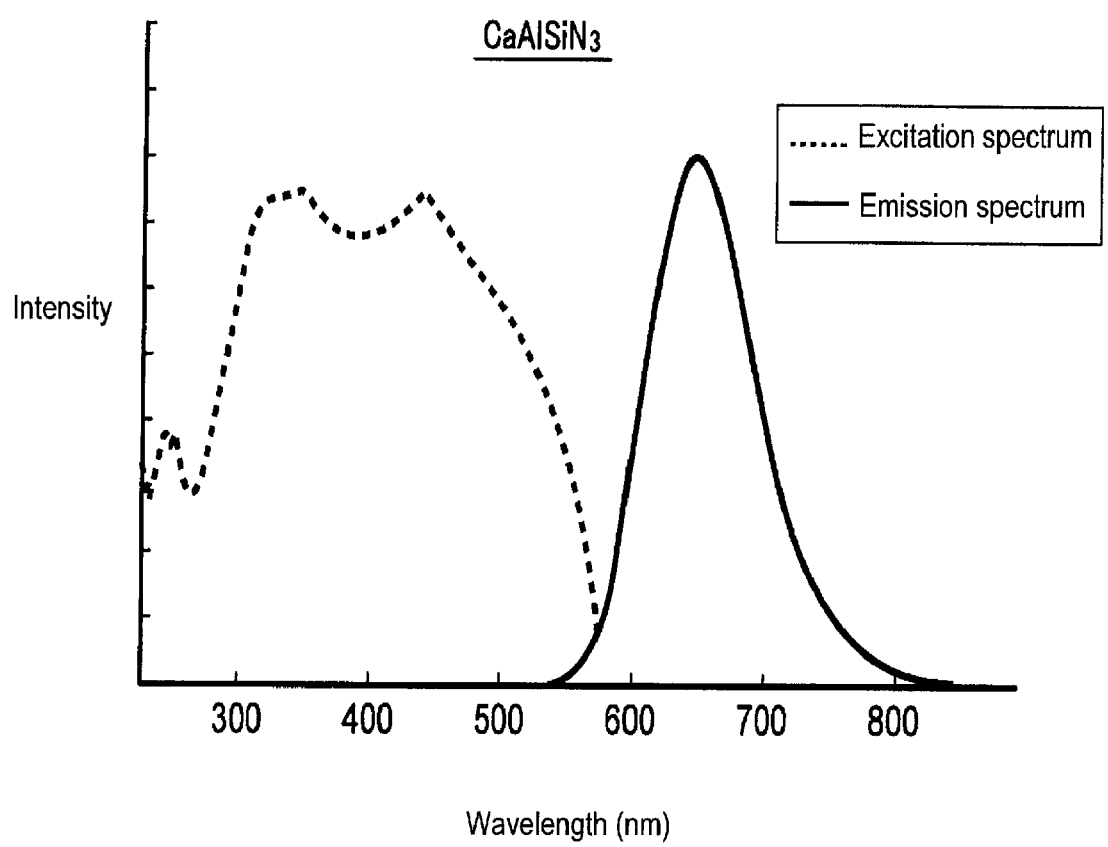
FIG. 15 is a graph illustrating excitation spectrum and emission spectrum of a $CaAlSiN_3$ red phosphor.

Main light components, which are included in a screen of a specific detection color, for each frame image imaged in a similar manner to FIGS. 12A and 12B are shown in FIG. 14. Here, instead of a YAG phosphor, a β-SiALON green phosphor and a $CaAlSiN_3$ red phosphor are used as the first wavelength conversion member. Thus, a phosphor is used which is excited to emit light even if light has any wavelength of 375 nm and 445 nm. The excitation spectrum and emission spectrum of the CaAlSiN$_3$ red phosphor are shown in FIG. 15. The CaAlSiN$_3$ red phosphor is efficiently excited by blue light having a wavelength of 450 nm and emits red light near 650 nm. With this combination of the phosphors, the wavelength conversion member 145 can be excited to emit light by light from any of the blue laser light source 133 (refer to FIG. 8) and the near-ultraviolet laser light source 135. Thus, since the amount of light components emitted is increased, the light use efficiency is improved.

As shown in FIG. 14, in the first frame that is an imaging signal obtained by imaging under irradiation of the laser beam having the center wavelength of 445 nm, a blue detection light screen B1 includes an observation light based on illumination light of (i) the laser beam having the center wavelength of 445 nm from the blue laser light source 133 and (ii) blue fluorescent light by β-SiALON of the first wavelength conversion member, a green detection light screen G1 includes an observation light based on illumination light of green fluorescent light by β-SiALON of the first wavelength conversion member, and a red detection light screen R1 includes an observation light based on illumination light of red fluorescent light by CaAlSiN$_3$ of the first wavelength conversion member. Then, in the second frame that is an imaging signal obtained by imaging under irradiation of the laser beam having the center wavelength of 375 nm, a blue detection light screen B2 includes observation light based on illumination light of the blue fluorescent light by β-SiALON of the second wavelength conversion member, a green detection light screen G2 includes observation light based on illumination light of (i) green fluorescent light by β-SiALON of the second wavelength conversion member and (ii) narrowband green fluorescent light by LiTbW$_2$O$_8$ of the second wavelength conversion member, and a red detection light screen R2 includes observation light based on illumination light of the red fluorescent light from CaAlSiN$_3$ of the second wavelength conversion member.

Then, in the third frame that is an imaging signal obtained by imaging under irradiation of the laser beam having the center wavelength of 445 nm has the same light components as the first frame. Similarly, the fourth frame has the same light components as in the second frame, and the fifth frame has the same light components as in the third frame (first frame), and these are repeated.

Here, although the observation light under the narrowband green fluorescent light by LiTbW$_2$O$_8$ of the second wavelength conversion member is included in G1 of the first frame, the observation light is superimposed on the observation light based on the blue fluorescent light by β-SiALON and becomes a broadband spectrum. Accordingly, the observation light based on the original narrowband green fluorescent light cannot be detected directly. For this reason, by subtracting the green detection light screen G1 of the first frame from the green detection light screen G2 of the second frame in order to offset a green fluorescent component of β-SiALON, observation light based on only the narrowband green fluorescent component by LiTbW$_2$O$_8$ can be selectively extracted.

Similarly, although the laser beam having the wavelength of 445 nm in the narrow wavelength band is also included in B1 of the first frame, the laser beam cannot be detected directly because the laser beam is superimposed on blue fluorescent light based on β-SiALON. Therefore, by subtracting B2 from B1, observation light based on only the laser beam having a wavelength of 445 nm can be extracted selectively.

Moreover, also for an observation light image obtained under white light, it becomes possible to acquire an image including a larger amount of information by performing the above-described process between frames. Although the observation light based on the white light illumination is obtained in the first and third frames (odd frames), it can improve color rendering properties by using the blue fluorescent light, which has a relatively wide wavelength bandwidth, based on β-SiALON in the second frame rather than by using the illumination light in which a laser beam as a bright line component is mixed. Thus, an observation light image obtained under based on white light, which has better color rendering properties, can be obtained by combining G1 and R1 of the first frame with B2 of the second frame without using the first frame as the observation light image obtained under the white light.

In addition, the narrowband green fluorescent component based on LiTbW$_2$O$_8$ obtained by G2-G1 and the observation light image based on the laser beam component having the wavelength of 445 nm obtained by B1-B2 can be obtained as an observation light image based on narrowband illumination light. Moreover, it is needless to say that arbitrary setting can be made to such combinations. For example, an observed image illuminated (white-illuminated) by the blue laser beam having the center wavelength of 445 nm, an observed image illuminated by the green laser beam having the center wavelength of 405 nm in the narrow wavelength band of green, and an observed image illuminated by the emitted excitation light in the wide wavelength band of blue based on the near-ultraviolet laser beam having the center wavelength of 375 nm may be acquired in the first, second, and third frames, respectively, and they may be subjected to the calculation process in the respective frames.

As described above, image information convenient for diagnosis can be easily provided by using the proper combination of the detection light screens of the frames obtained by the imaging. For example, observation light based on the laser beam having the wavelength of 445 nm is acquired by an operation (B1-B2), and the acquired observation light is assigned to blue and green color tones. Observation light based on narrowband green fluorescent light by LiTbW$_2$O$_8$ is acquired by an operation (G2-G1), and the acquired observation light is assigned to a red color tone. Thus, by generating a emphasized image having a pseudo color by converting an observed image based on light with a specific wavelength component into a specific color tone, a capillary vessel of a tissue surface layer, a gland tube structure (pit pattern), and the like are emphasized, which may greatly contribute to finding a malignant tumor at which capillary vessels concentrate.

By (i) a combination of phosphors suitable for acquisition of an imaging signal in a narrow band of blue or green, (ii) switching of excitation light sources in time-series manner, and (ii) a signal calculation method which is useful for the endoscope described above, an emission wavelength band can be clearly separated by switching of excitation light, and selective emission can be realized.

Accordingly, it is possible to easily acquire an image in which a capillary vessel of a surface layer of the tissue is clearly formed by blue light which is difficult to reach a deep portion of a mucous membrane and in which a blood vessel of a deep portion is clearly formed by green light which arrives even at the inside of the tissue. Moreover, in the above description, the illumination light is obtained by turning on one of the blue laser light source 133 and the near-ultraviolet laser light source 135 and turning off the other. In addition to this method, however, a light component in a desired emission wavelength band may also be extracted by turning on both the laser light sources to excite a phosphor and performing proper calculation processing for an imaged image obtained by imaging in this state.

As described above, according to the endoscope apparatus 101, since the laser light source is used as the light source of the illumination optical system, light can be guided through the optical fiber. As a result, since diffusion of high-intensity light can be suppressed, the light can be made to propagate with high efficiency. Furthermore, since the coaxial illumination structure in which the white light and light in a specific narrow visible wavelength band are irradiated from the same optical path, it is not necessary to newly provide plural illumination optical systems in the insertion portion of the endoscope. Furthermore, since the light guiding path can be formed by the optical fiber, a light guide of the related art (optical fiber bundle) is not needed. Accordingly, it becomes easy to make the diameter of the endoscope insertion portion small.

Moreover, since laser beams from the near-ultraviolet laser light source 135 which generates light in a specific narrow visible wavelength band is invisible light, all of the laser beams are not wavelength-converted by the second wavelength conversion member. Accordingly, even if a part of the laser beams are transmitted through the second wavelength conversion member, the color balance of illumination light emitted is not affected. As a result, the diagnostic precision of the endoscope can be maintained high without causing a color change in an observed image within the body cavity. In addition, the near-ultraviolet laser beams from the near-ultraviolet laser light source 135 are hardly absorbed by the first wavelength conversion member. Accordingly, since a drop in light intensity is small, an illumination optical system with high light use efficiency can be built.

A wavelength band of excitation light of the above-described second wavelength conversion member is preferably set so that the full bandwidth at half maximum is 40 nm or less. This is based on the following reasons. An imaging device, such as a CCD or a CMOS, has a color filter. For example, full-color image information is generated by setting primary colors (also including the combination of cyan, magenta, and yellow as complementary colors) of R (red), G (green), and B (blue) as specific detection colors. In light intensity detection of each detection color, the light intensity in an effective sensitivity wavelength band of a certain wavelength width is detected. However, since wavelengths of the respective detection colors are practically close to each other, parts of the effective sensitivity wavelength bands overlap each other. Color mixture occurs, if there are many overlap regions. Therefore, the overlap regions are usually made narrow.

The effective sensitivity wavelength band is designed to 100 nm or less in B, to 80 nm or less in U, and to 100 nm or less in R in order to prevent color mixture with G (in this specification, this is called a "substantial effective sensitivity wavelength band"). Therefore, in order to detect each detection color with no influence of color mixture in an imaging device, it is preferable that a wavelength band of excitation light is smaller than the substantial effective sensitivity wavelength band. In other words, a full width of an emission spectrum curve of a specific visible wavelength band in which the wavelength conversion member 145 is excited to emit light, at half maximum thereof, is smaller than a full width of a spectral sensitivity curve of a wavelength band in which a specific detection color of a color filter is detected, at half maximum thereof. Accordingly, excitation light in a specific wavelength band is not detected any more over plural effective sensitivity wavelength bands. Moreover, according to a body to be inspected to be observed, the center of the spectrum may be shifted from the center of a color filter. In this case, it is necessary to make narrower the width of the wavelength band of excitation light.

For this reason, the width of the wavelength band of the excitation light of the second wavelength conversion member 47 is set to 60 nm or less, preferably to 40 nm or less, and more preferably 20 nm or less. Moreover, from the point of view of light intensity, this width is preferably 10 nm or more. The width of the wavelength band of the excitation light may be arbitrarily set by appropriately selecting the second wavelength conversion member, for example.

Moreover, in addition to the reason of light intensity detection of the imaging device, a point that making a band narrow is needed when performing a diagnosis using a narrowband endoscope (narrowband imaging: NBI) will also be described. When illumination light is irradiated to a living body tissue, the light propagates while diffusing. If absorption or scattering property is strong, the light is observed as reflected light without propagating deeply into the living body tissue. The absorption and scattering properties have strong wavelength dependency. The shorter the wavelength, the stronger the scattering property. Accordingly, the invasion depth of the living body tissue at which light can arrive is determined by the wavelength of light irradiated. Particularly, for observation of a microstructure of a mucous surface which is important for early diagnosis of a disease, information from a shallow layer from the surface is important. In this case, information from a layer to be observed can be selectively extracted by setting a wavelength band of excitation light of the second wavelength conversion member to a desired wavelength and making the wavelength band narrow.

As described above, according to the endoscope apparatus of this embodiment, either the white light, which is formed including a laser beam and light emitted by excitation of a phosphor, or light in a specific narrow visible wavelength band can be selectively irradiated with the simple configuration while making the diameter small. In addition, the light source device and the endoscope apparatus using the light source device are not limited to this embodiment described above but may be suitably changed or modified. For example, the user-friendliness can be improved by performing free switching between white light and light in a specific narrow visible wavelength band by an easy manual operation using a switch provided in the main body operation portion 111 of the endoscope 110.

[Fourth Embodiment]

Figure 16:
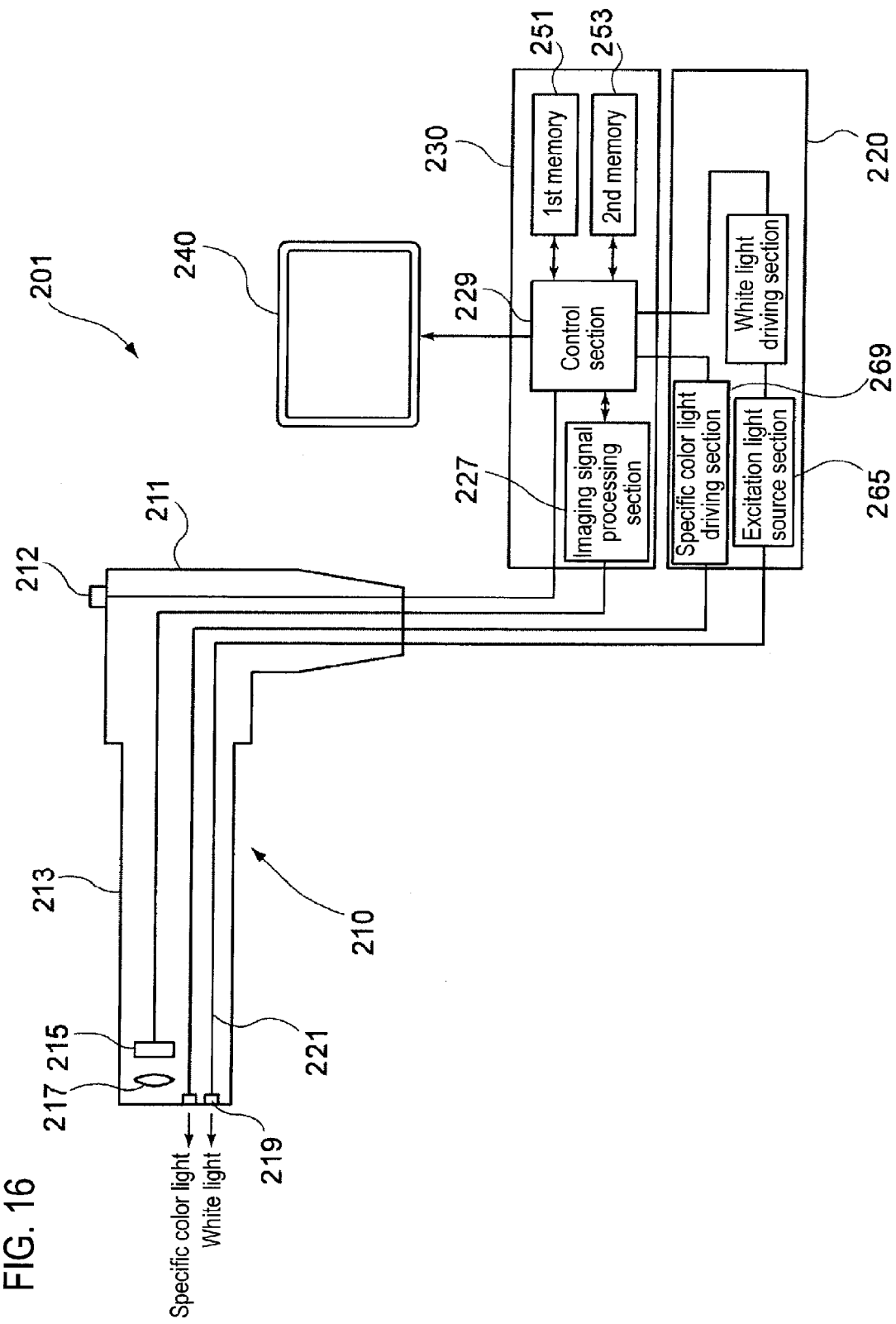
FIG. 16 is a view illustrating the conceptual configuration of the endoscope apparatus according to a fourth embodiment of the invention.

Hereinafter, a light source device according to a fourth embodiment, an endoscope apparatus using this light source device, and an image processing method will be described in detail with reference to the accompanying drawings. FIG. 16 is a view illustrating the conceptual configuration of the endoscope apparatus according to the fourth embodiment. An endoscope apparatus 201 is configured to mainly include an endoscope 210, a light source device 220, an image processing device 230, and a monitor 240. The endoscope 210 includes a main body operation portion 211 and an endoscope insertion portion 213 which is provided to be connected to the main body operation portion 211 and is inserted into a body to be inspected (body cavity). An imaging device 215 and an imaging lens 217 which constitute an imaging optical system are disposed at the tip of the insertion portion 213. Moreover, an illumination optical member 219 of an illumination optical system and an optical fiber 221 connected to the illumination optical member 219 are disposed near the imaging optical system. The optical fiber 221 is connected to the light source device 220, which will be described in detail later, and an imaging signal from the imaging device 215 is input to the image processing device 230.

An imaging device, such as a CCD or a CMOS, is used as the imaging device 215. The imaging signal is converted into image data by an imaging signal processing section 227 based on a command from a control section 229 and appropriate image processing is performed for the image data. The control section 229 outputs the image data output from the imaging signal processing section 227, as an image, to the monitor 240 which is an imaged image display unit or distributes information including the image data through a network, such as a LAN (not shown). Moreover, a first memory 251 and a second memory 252 for storing imaging signals are connected to the control section 229. The first and second memories 251 and 252 will be described later.

Figure 17:
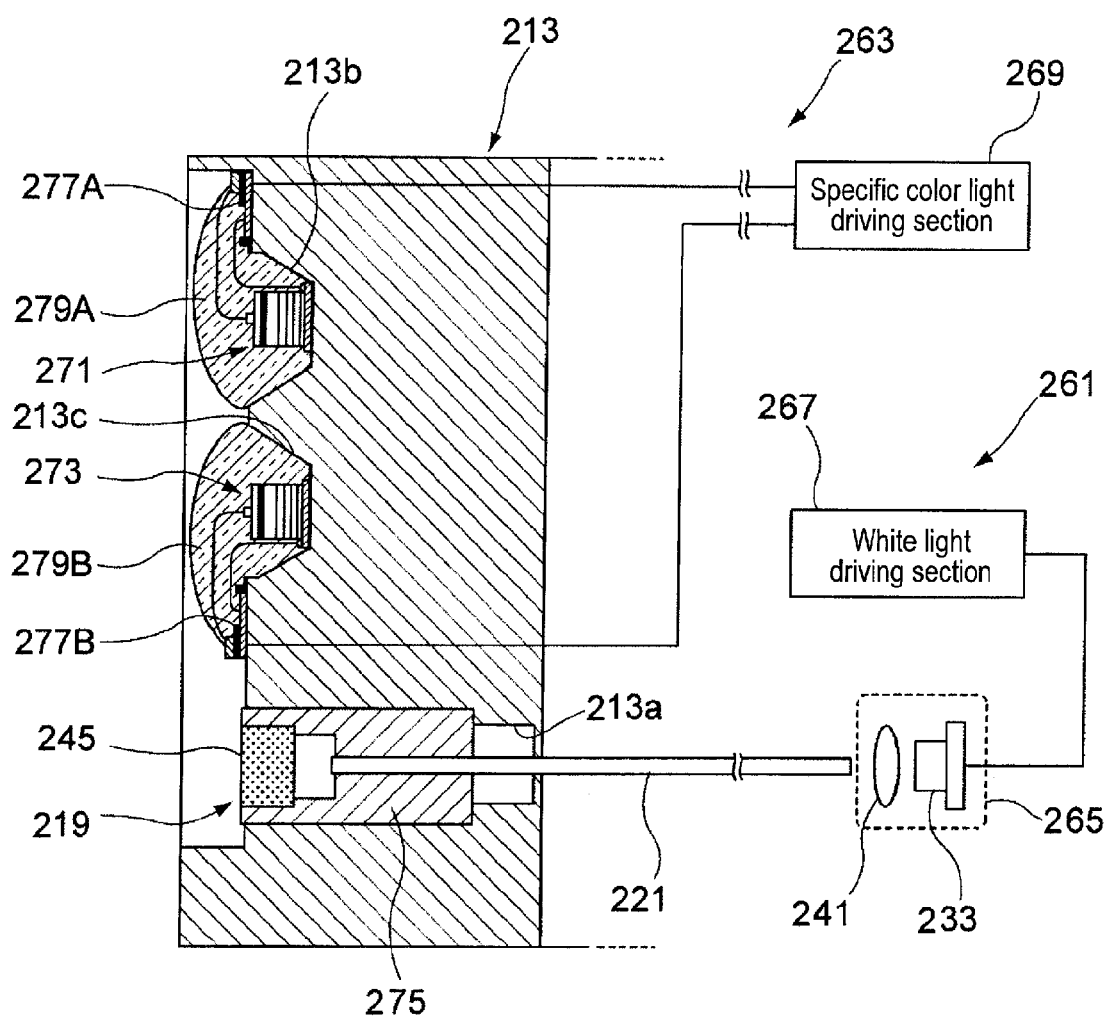
FIG. 17 is a view illustrating the schematic sectional configuration of an illumination optical system at the tip of an endoscope insertion portion of the endoscope apparatus shown in FIG. 16.

Next, an example of the configuration of the illumination optical system will be described. FIG. 17 is a view illustrating the schematic sectional configuration of the illumination optical system at the tip of an endoscope insertion portion of the endoscope apparatus shown in FIG. 16. The illumination optical system is configured to include a white light illumination system 261 for emitting white light and a specific color light illumination system 63 for emitting specific color light, such as green light and blue light. The white light illumination system 261 includes an excitation light source section 265 having a blue laser light source (first light source) 233 having a center wavelength of 445 nm and a condensing lens 241 for condensing a laser beam from the blue laser light source 233. The illumination optical member 219 disposed at the tip of the endoscope insertion portion 213 is formed by a wavelength conversion member 245 which converts a laser beam into visible light. Moreover, the excitation light source section 265 and the illumination optical member 219 are connected to each other by the optical fiber 221.

The blue laser light source 233 emits a blue laser beam while controlling the amount of emitted light based on a command from a white light driving section 267. The emitted light is irradiated to the wavelength conversion member 245 of the endoscope insertion portion 213 through the optical fiber 221. The wavelength conversion member 245 is configured to include plural types of phosphors (for example, a YAG-based phosphor or a phosphor including BAM ($BaMgAl_{10}O_{37}$)) which absorb a part of the laser beam from the blue laser light source 233 and are excited to emit light of green to yellow. Then, the laser beam from the blue laser light source 233 and the excitation light of green to yellow converted from the laser beams are mixed to generate white light.

As the blue laser light source 233, a broad area type InGaN laser diode may be used. Moreover, the optical fiber 221 is inserted into a hole 213a formed in a front-end hard portion (metal block) of the endoscope insertion portion 213 and is fixed to a fixing jig 275, which is fit and fixed to the hole 213a, along the optical axis. The fixing jig 275 fixes the wavelength conversion member 245 at the light emission side of the optical fiber 221, and receives emitted light from the optical fiber 221 and emits light, which emitted by excitation of the wavelength conversion member 245, forward on the optical path. At this time, the blue laser beam transmitted through the wavelength conversion member 245 without wavelength conversion is diffused by the phosphor in the wavelength conversion member 245 and is emitted as diffused light which has a diffusion angle of 60° to 70° with respect to the optical axis from a laser beam with high directivity.

On the other hand, a specific color light illumination system 263 uses an LED (light emitting diode) device as a light source and is configured to include a blue LED device 271 and a green emission LED device 273 which are connected to a specific color light driving section 269. The blue LED device 271 and the green emission LED device 273 are respectively disposed in receiving seats 213b and 213c which are formed to be recessed in the front-end hard portion and whose side walls are reflective surfaces. Near the receiving seats 213b and 213c, electrode pads 277A and 277B are respectively disposed to be connected to N-type and P-type electrodes of each LED device by wire bonding. Moreover, each of the LED devices 271 and 273, each of the electrode pads 277A and 277B, and a gold wire are molded with a transparent resin. These molded transparent resins 279A and 279B function as lenses. Moreover, they are described as a blue LED and a green LED. However, since the luminous efficiency of the green LED is low, a 405 nm purple LED may be used, for example, by mixing a phosphor which emits green light, dye, or pigment in a transparent resin. Similarly, a 375 nm ultraviolet LED and a phosphor which emits purple-blue light may be mixed in a resin and be sealed.

The specific color light driving section 269 separately controls the amount of light emitted from the blue LED device 271 and the green emission LED device 273. The specific color light driving section 269 is controlled together with the white light driving section 267 by the control section 229 (FIG. 17). The white light driving section 267, the specific color light driving section 269, and the control section 229 function as an illumination light control unit that performs switching of illumination light and the like. With the above-described configuration, the blue laser beam from the blue laser light source 233 emitted from the optical fiber 221 is irradiated to the wavelength conversion member 245, and the wavelength conversion member 245 absorbs a part of the blue laser beam and is excited to emit light (light of green to yellow) which has a longer wavelength than the blue laser beam.

Figure 18:
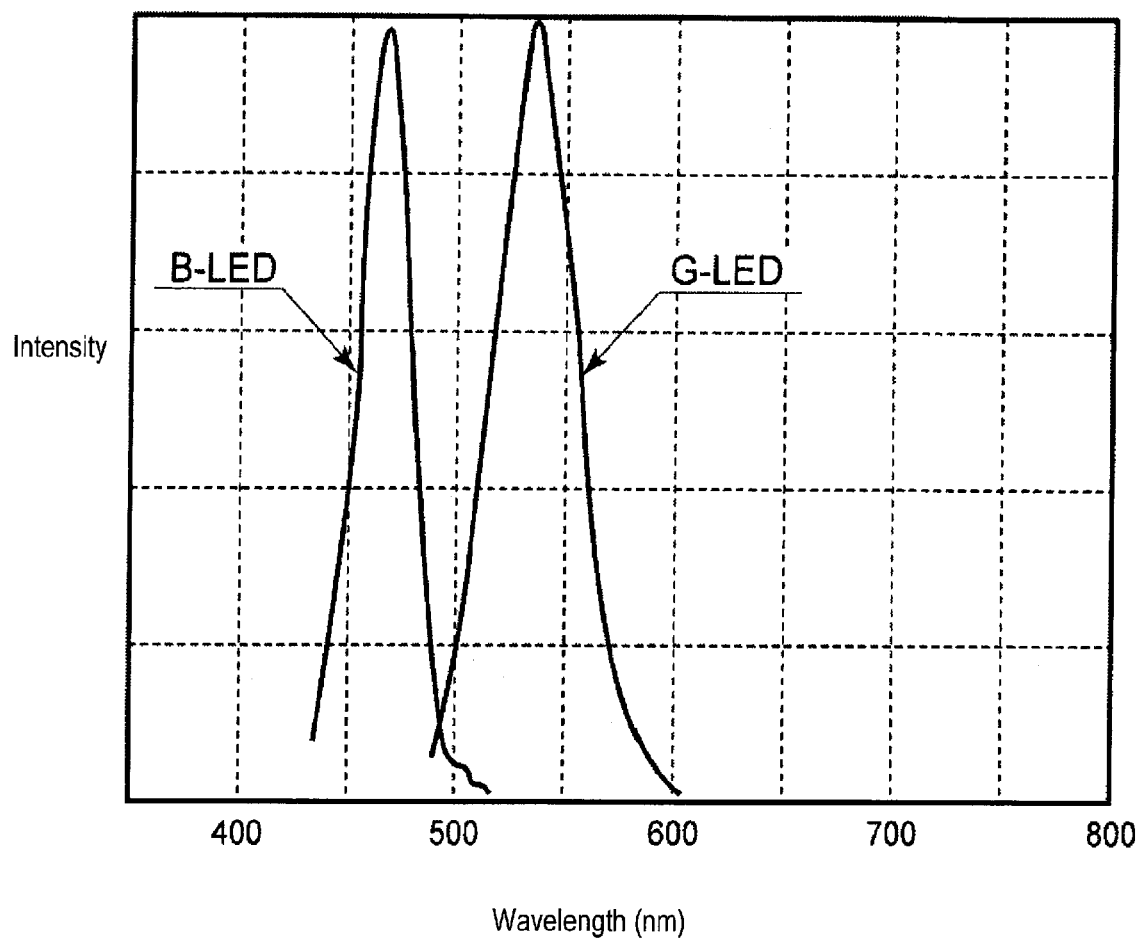
FIG. 18 is emission spectrums of a blue LED device and a green emission LED device of a specific color light illumination system.

FIG. 18 is a graph illustrating the spectrum distribution of light after a blue laser beam is wavelength-converted by the wavelength conversion member 245. The blue laser beam from the blue laser light source 233 is expressed by an emission line having a center wavelength of 445 nm. Light emitted from the wavelength conversion member 245 excited by the laser beam increases the emission intensity in a wavelength band of approximately 450 nm to 700 nm White light is formed by light within the wavelength band and the blue laser beam.

FIG. 18 is emission spectrums of the blue LED device 271 and the green emission LED device 273 of the specific color light illumination system 263. The emission spectrum obtained by the blue LED device 271 is light having a narrow wavelength band of about 450 to 480 nm at half maximum thereof, and the emission spectrum obtained by the green emission LED device 273 is light having a narrow wavelength band of about 520 to 560 nm at half maximum thereof.

Next, an example of the use of the endoscope apparatus 201 when the light source device 220 having the above-described configuration is built into the endoscope 210 will be described. As shown in FIG. 17, in the endoscope apparatus 201, the endoscope insertion portion 213 is inserted into a body cavity, white illumination light is illuminated through the illumination optical member 219 from the tip of the endoscope insertion portion 213, and the illumination light by specific color light is emitted from each of the LED devices 271 and 273. The white light and the specific color light are switched so that only one of them is emitted. In addition, reflected light after the emitted light is irradiated to the body to be inspected is imaged through the imaging lens 217 in the imaging device 215. An imaging signal obtained by imaging is output to the monitor 240 after being subjected to appropriate image processing by the imaging signal processing section 227. Or the imaging signal is stored in a recording medium.

In case of imaging using this imaging device 215, at the time of normal endoscopic diagnosis in which observation is performed by irradiating white illumination light within the body cavity, the control section 229 turns on an output of a laser beam from the blue laser light source 233 by the white light driving section 267 shown in FIG. 17 and turns off each output of the blue LED device 271 and the green emission LED device 273 by the specific color light driving section 269. In this case, white illumination light generated by the laser beam from the blue laser light source 233 and the light emitted by excitation of the wavelength conversion member 245 is irradiated to the body to be inspected. Moreover, when performing spectral diagnostics by the endoscope apparatus 201, the control section 229 turns on each output of the blue LED device 271 and the green emission LED device 273 by the specific color light driving section 269 and turns off an output of the blue laser light source 233 by the white light driving section 267. In this case, blue light and green light having narrow wavelength bands by the blue LED device 271 and the green emission LED device 273 are irradiated to the body to be inspected. Then, reflected light from the body to be inspected to which the green light and the blue light are illuminated simultaneously is imaged by the imaging device 215, and the imaging signal processing section 227 generates a pseudo color image for spectral diagnostics. For example, the pseudo color image is generated by converting a green detection signal (reflected light component of narrowband green light) obtained by the imaging device 215 into a red color tone and converting a blue detection signal into blue and green color tones. According to the pseudo color image, a surface microstructure (for example, a microstructure of a capillary vessel or a mucous membrane) of a surface layer of a body to be inspected can be clearly observed.

Figures 19A, 19B:
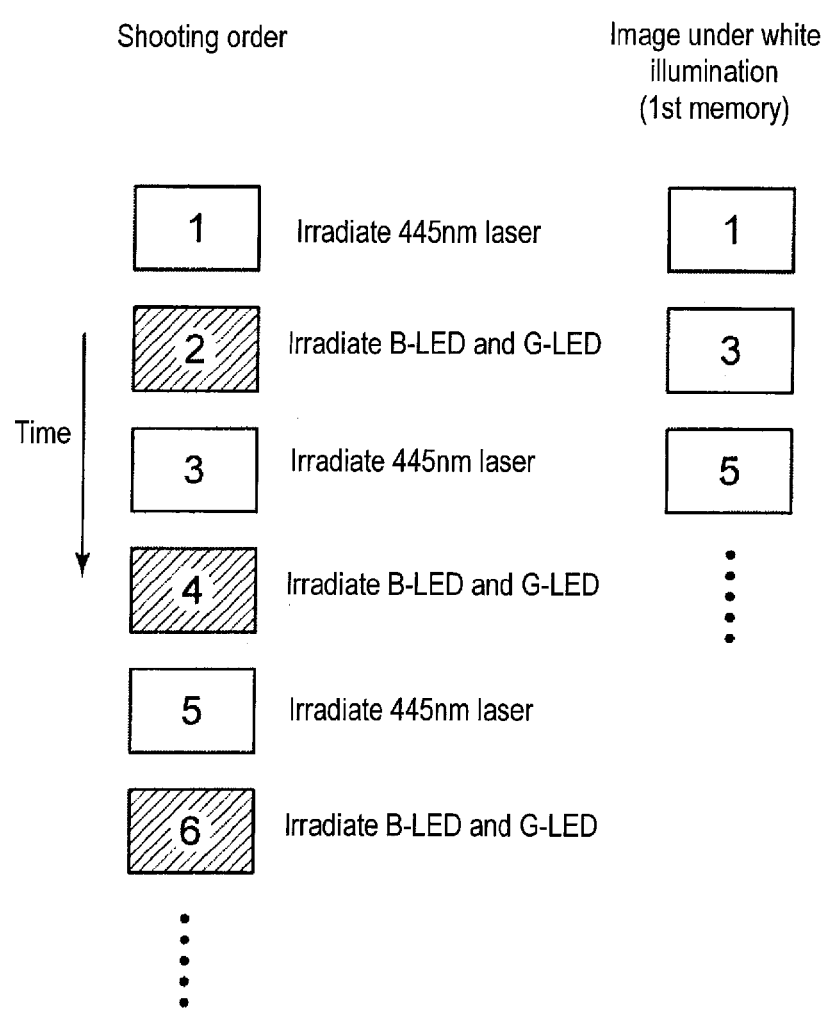
FIG. 19A is an explanatory view conceptually illustrating plural frame images which are obtained in a time-series manner by imaging by an imaging optical system.
FIG. 19B is an explanatory view conceptually illustrating a state where the frame images of FIG. 19A are rearranged and displayed.

Here, a specific control example of spectral diagnostics will be described. FIG. 19A is a view illustrating plural frame images obtained in a time-series manner by imaging with the imaging optical system, and FIG. 19B is an explanatory view conceptually illustrating a state where these frame images are rearranged and displayed. Here, an observed image under illumination light of white light and an observed image under illumination light in a specific visible wavelength band (green, blue) are separately displayed on the monitor 140. As shown in FIG. 19A, the control section 229 controls the light source device 20 to emit the blue laser beam having the center wavelength of 445 nm in a first frame, thereby irradiating the white light to the body to be inspected. The imaging device 215 images the body to be inspected illuminated by the white light and stores the imaging signal in the first memory 251 (see FIG. 16).

Then, the control section 229 controls emitted light from the light source device 220 to irradiate blue light and green light with narrow wavelength bands, which are obtained by the blue LED device 271 and the green emission LED device 273, to the body to be inspected in the second frame. The imaging device 215 images the body to be inspected illuminated by the green light and the blue light and stores the imaging signal in a second memory 253.

Hereinafter, in the same manner as described above, processing of irradiation (illumination) of light, imaging, and storing of an imaging signal is repeatedly performed similarly to the first frame in a third frame (odd frame) and similarly to the second frame in a fourth frame (even frame). That is, the illumination of the white light and the illumination including light in the specific visible wavelength band are alternately switched every imaging frame of the imaging device 215. Then, as shown in FIG. 19B, the illumination images under the white light are accumulated in the first memory 251, and the images for narrowband diagnosis under the green light and the blue light are accumulated in the second memory 253. As image information based on these two types of imaging signals, the imaging signals stored in the first and second memories are displayed in different display regions 255 and 257 on the monitor 240, like in FIG. 13. Although the sizes of the display regions are set equal in the example shown in FIG. 13, the sizes may be set arbitrarily. For example, one of the display regions may be displayed larger than the other display region, or the other image may be displayed small within one display region.

Thus, by alternately imaging an image under the illumination of the white light and an image under the illumination including the light in the specific visible wavelength band, both the images can be acquired approximately at the same time. Accordingly, two types of image information can be simultaneously displayed in real time. In addition, since the observation position and the property of the observed portion can be understood simultaneously by displaying the imaged images side by side, the diagnostic precision based on the spectral diagnostics can be further improved.

Moreover, when performing imaging by irradiating light in a specific visible wavelength band to perform spectral diagnostics, the combination of various light components is also available in addition to the combination of illumination light of the blue light from the blue LED device and the green light from the green emission LED device. A pseudo color image may also be generated by using a blue laser beam from the blue laser light source 233 for white illumination, for example, as narrowband specific color light instead of the blue light from the blue LED device 271. The pseudo color image obtained as described above may become an image useful for spectral diagnostics since a wavelength band of emitted light is narrower than that of the LED device.

Figure 20:
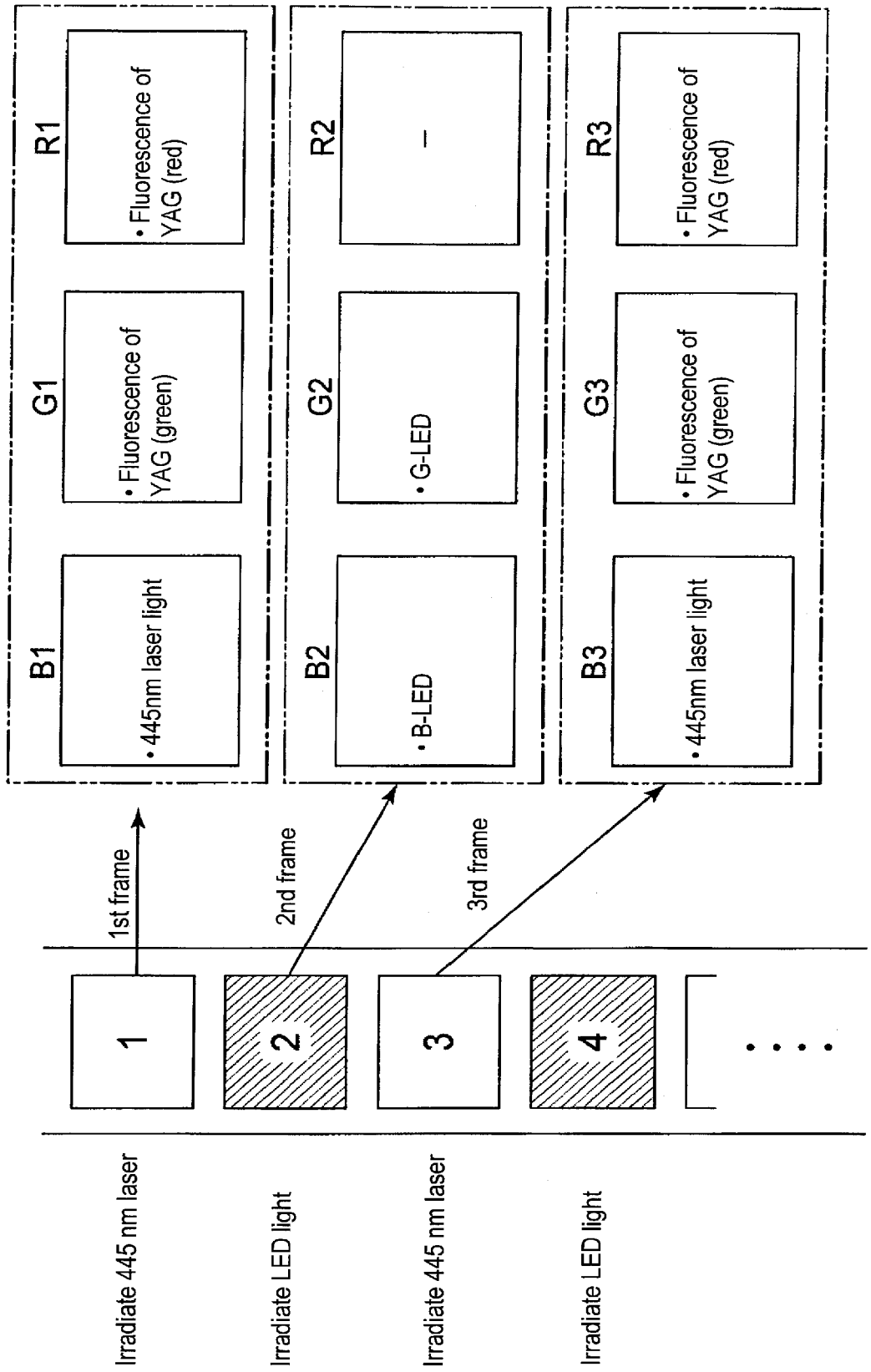
FIG. 20 is an explanatory view illustrating main light components, which are included in a screen of a specific detection color, for each frame image which is imaged in a similar manner to FIG. 19A.

Main light components, which are included in a screen of a specific detection color, for each frame image that is imaged in a similar manner to FIGS. 19A and 19B are shown in FIG. 20. Here, an example where a YAG phosphor is used as a phosphor of the wavelength conversion member 245 will be described. In a first frame that is an imaging signal obtained by imaging based on irradiation of a blue laser beam having the center wavelength of 445 nm, a blue detection light screen B1 includes observation light based on illumination light of the blue laser beam having the center wavelength of 445 nm from the blue laser light source 233, a green detection light screen G1 includes observation light based on illumination light of green fluorescent light by the YAG phosphor of the wavelength conversion member 245, and a red detection light screen R1 includes observation light based on illumination light of red fluorescent light by the YAG phosphor of the wavelength conversion member 245.

Then, in a second frame that is an imaging signal obtained by imaging based on emission of the blue LED device 271 and the green emission LED device 273, a blue detection light screen B2 includes observation light based on illumination light from the blue LED device 271, and a green detection light screen G2 includes observation light based on illumination light from the green emission LED device 273.

Here, when an observed image obtained by white light is considered, the white light used for illumination becomes a different color tone from that is actually seen if a wavelength component in a specific narrow range becomes strong. Accordingly, it is ideally desirable to perform illumination with light having a spectrum in which a visible wavelength band is relatively flat. However, as for white illumination in this configuration, the blue laser beam as an emission line is used for white illumination. Accordingly, if this is replaced with emitted light from the blue LED device 271 having a larger wavelength width than a laser beam, the spectrum of illumination light can be made flatter. That is, at the time of white illumination, it can improve the color rendering properties to use blue light having a relatively large wavelength bandwidth from the LED device in the second frame rather than illumination light in which a laser beam as an emission line component is mixed. Thus, an observation light image based on the white light, which has better color rendering properties, can be obtained by combining G1 and R1 of the first frame with B2 of the second frame without using the first frame as the observation light image based on white light.

Moreover, as an observation light image obtained by narrowband illumination light, observation light by the blue laser beam obtained on B1 and observation light by narrowband light obtained by emission of the green emission LED device 273 obtained on G2 may be combined, and this may be used as an image for emphasizing process. In this case, since the wavelength width of blue light is small, a tissue surface layer to be observed can be limited to a shallower region at the surface side.

In addition, it is also possible to adopt the configuration where white illumination light and light in a specific narrow visible wavelength band can be freely switched by an easy manual operation using a switch 212 provided in the main body operation portion 211 of the endoscope 210. In this case, since illumination light can be switched at arbitrary timing manually, the user-friendliness can be improved.

As described above, according to the endoscope apparatus 201, the diameter of a light guide needs to be at least about 1 mm or more in order to guide required light to the tip of the endoscope insertion portion 213 with the light guide. However, in the configuration of using a single-line optical fiber, the external diameter including a protective material of an outer coat can be set as small as about 0.3 mm. In addition, since the LED device performs illumination by directly converting energy into a required wavelength band, light with high efficiency and high illuminance is obtained. Accordingly, as compared with the case where light in a narrow wavelength band is extracted by filtering from a xenon lamp generally used in the endoscope, the same brightness can be realized with about 1/20 power consumption. Moreover, since exhaust heat can also be reduced, a cooling fan and the like can be made small and the sound can be reduced. Moreover, since phosphor excitation light is used as illumination light, superimposition of a noise caused by speckle (interference) and flickering on a dynamic image, which easily occurs when a laser beam is used as direct illumination light, do not occur.

Moreover, according to the configuration of the endoscope apparatus 201, since the heat capacity is reduced due to making the diameter of the endoscope insertion portion 213 small, and heat emission from the LED devices 271 and 273 is concerned. However, since the white illumination light which requires a relatively large amount of light is supplied by using a laser beam and the specific illumination light required for spectral diagnostics is supplied by using the LED devices 271 and 273, the amount of heat emission can be suppressed compared with a case where an LED device is always lighted in high output.

Figure 21:
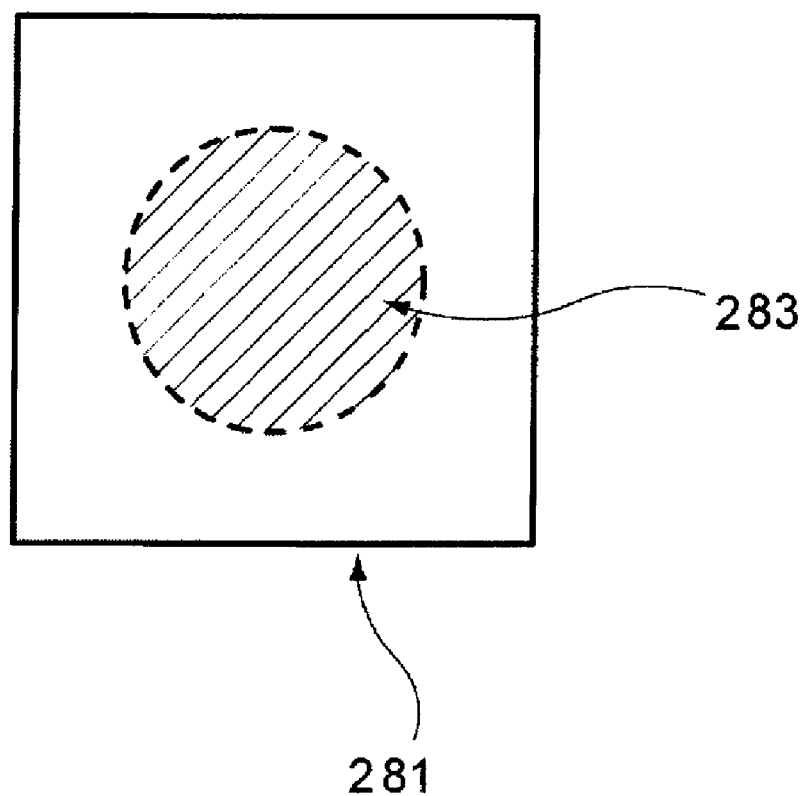
FIG. 21 is an explanatory view illustrating a relationship between an observation region and a specific color light irradiation region.

In addition, emitted light from the LED devices 271 and 273 is condensed by lenses formed of the transparent resins 279A and 279B and is then emitted toward a desired irradiation position. Therefore, as can be seen from the relationship between an observation region and a specific color light illumination region of FIG. 21, a part of an observation region 281 can be set as a specific color light illumination region 283 without illuminating the entire observation region 281 of the imaging device 215 with the LED devices 271 and 273. By setting the specific color light illumination region 283 as a narrow region so that selective irradiation can be performed, the amount of emitted light from the LED devices 271 and 273 becomes small. Accordingly, the amount of heat emission can be suppressed.

Next, a modification of the endoscope apparatus 201 with the above configuration will be described.

<First Modification>

Figure 22:
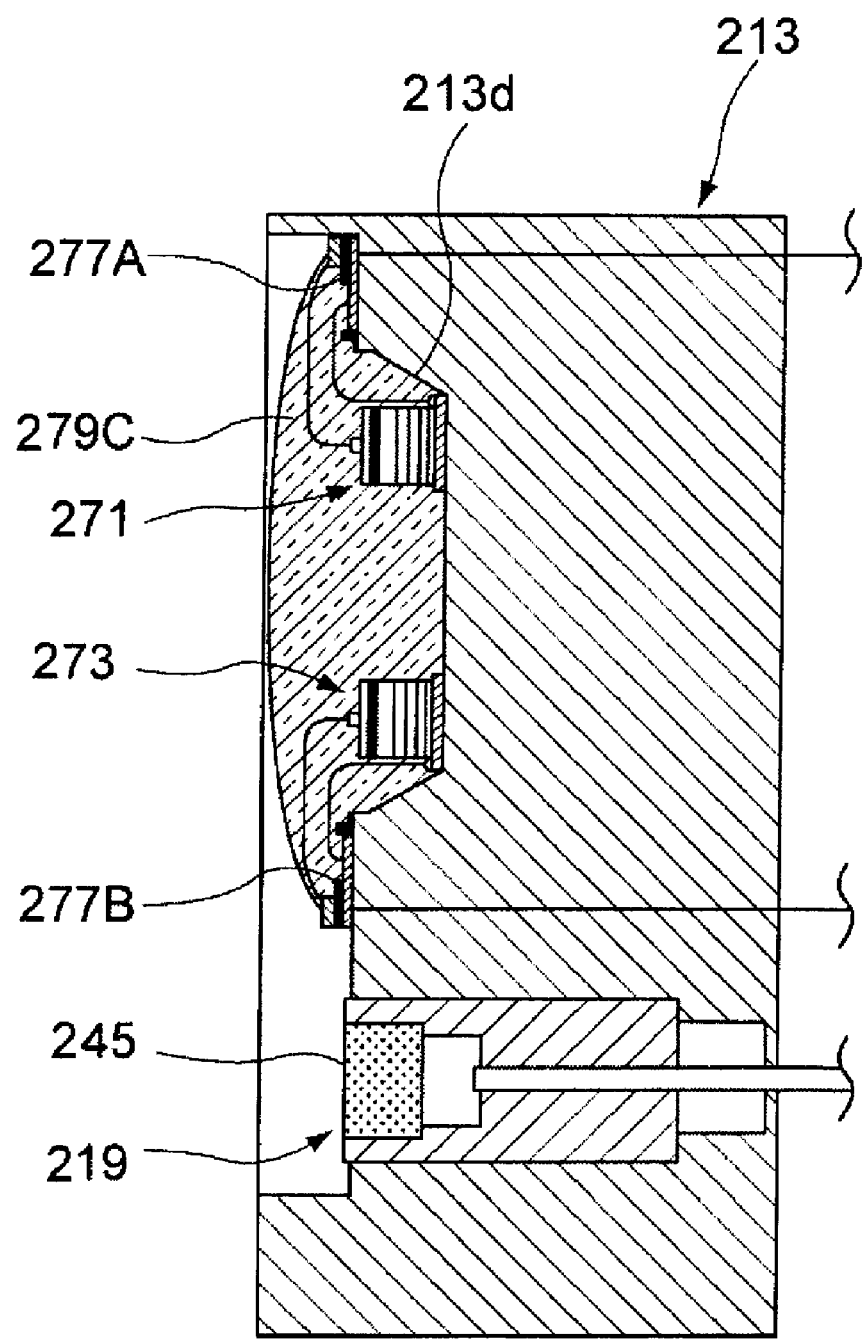
FIG. 22 is another section view illustrating the configuration of the endoscope insertion portion.

FIG. 22 is a view illustrating another sectional configuration of an endoscope insertion portion. In addition to the case where the receiving seats of the LED devices 271 and 273 formed in the endoscope insertion portion 213 of the endoscope apparatus 201 are respectively provided in the LED devices 271 and 273, the plural LED devices 271 and 273 may also be disposed in one receiving seat 213d. In this case, since the plural of LED devices 271 and 273 can be collectively molded by a transparent resin 279C, it is possible to simplify a manufacturing process. In addition, since the LED devices 271 and 273 share one condensing lens, irradiation unevenness of emitted light can be suppressed.

<Second Modification>

Figure 23:
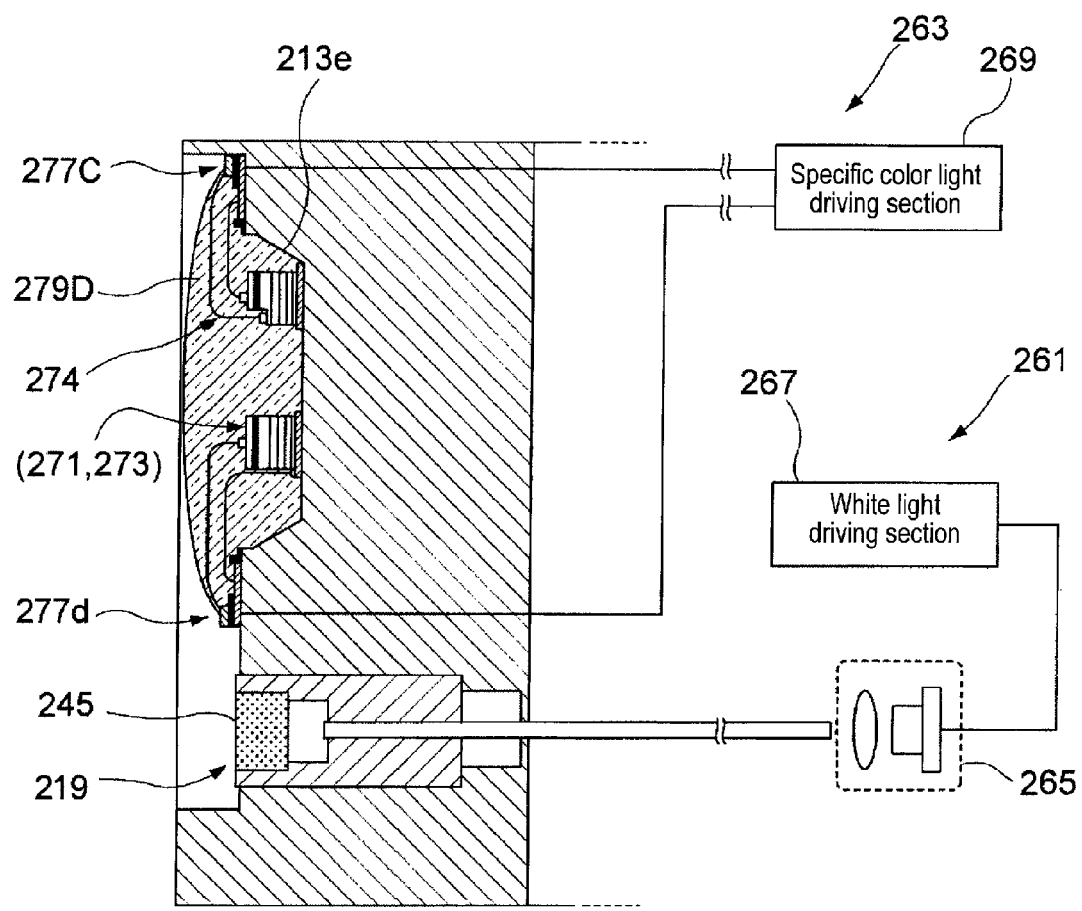
FIG. 23 is a view illustrating the configuration of another optical system of the light source device.

FIG. 23 is a view illustrating the configuration of another optical system of a light source device. LED devices in this case are the blue LED devices 271 and 273 (either one are provided in parallel to a direction perpendicular to the plane of the drawing) and an infrared (780 nm) emission LED device 276. The LED devices 271, 273, and 274 are disposed in the same receiving seat 213e and are molded with a transparent resin 279D. The blue LED device 271, the green emission LED device 273, and the infrared emission LED device 274 are all connected to the specific color light driving section 269 and the emission state is controlled.

Figure 24:
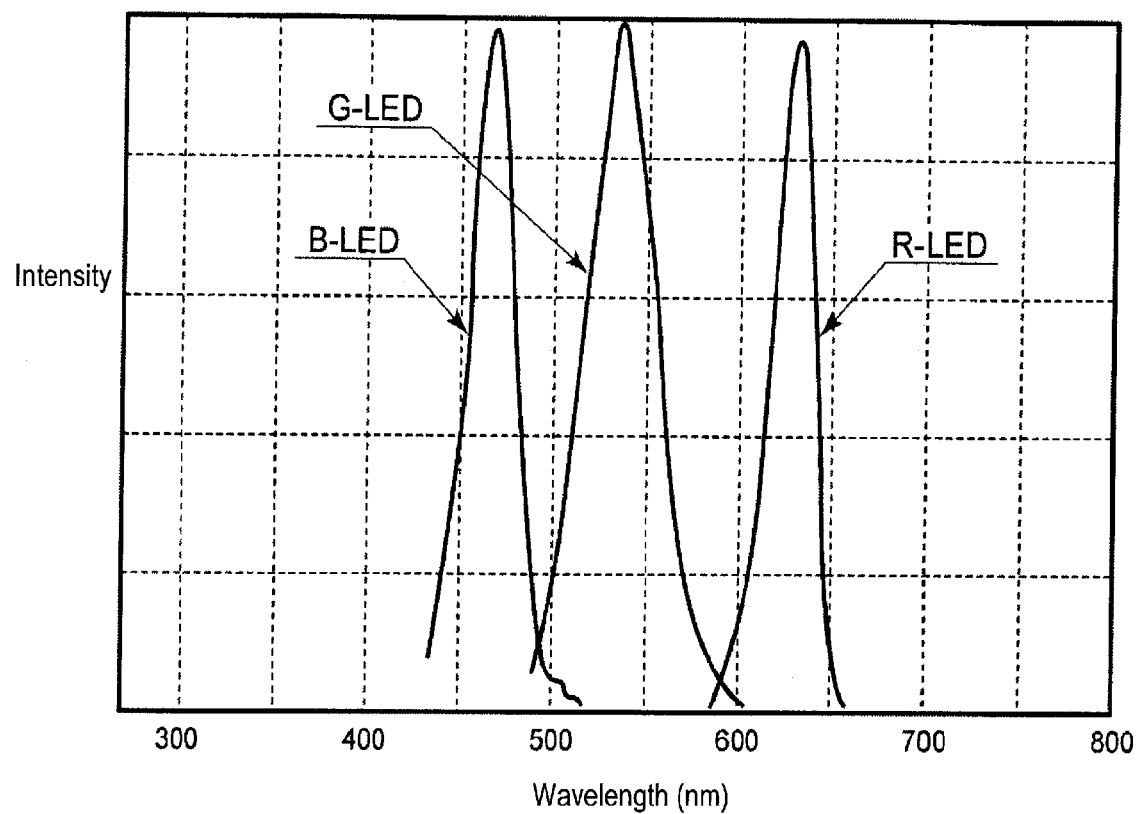
FIG. 24 is emission spectrums of a blue LED device, a green emission LED device, and an infrared emission LED device.

FIG. 24 is emission spectrums of the blue LED device 271, the green emission LED device 273, and the infrared emission LED device 274 in the case. According to this configuration, not only blue light to green light used for spectral diagnostics but also infrared light can be emitted. Accordingly, for example, a medical examination based on infrared light observation becomes possible. The infrared light observation is a technique of highlighting a blood vessel or hyperplasia of a deep portion of a mucous membrane, which is difficult to be seen to human eyes, by performing intravenous injection of ICG (indocyanine green) in which infrared light is easily absorbed and then irradiating infrared light. Moreover, blood flow information may also be displayed.

In each endoscope apparatus described above, for light with a narrow wavelength band used for spectral diagnostics or the like, that is, for emitted light of the blue LED device 271 and the green emission LED device 273, the wavelength band is preferably set to 40 nm or less in half bandwidth.

[Fifth Embodiment]

Figure 25:
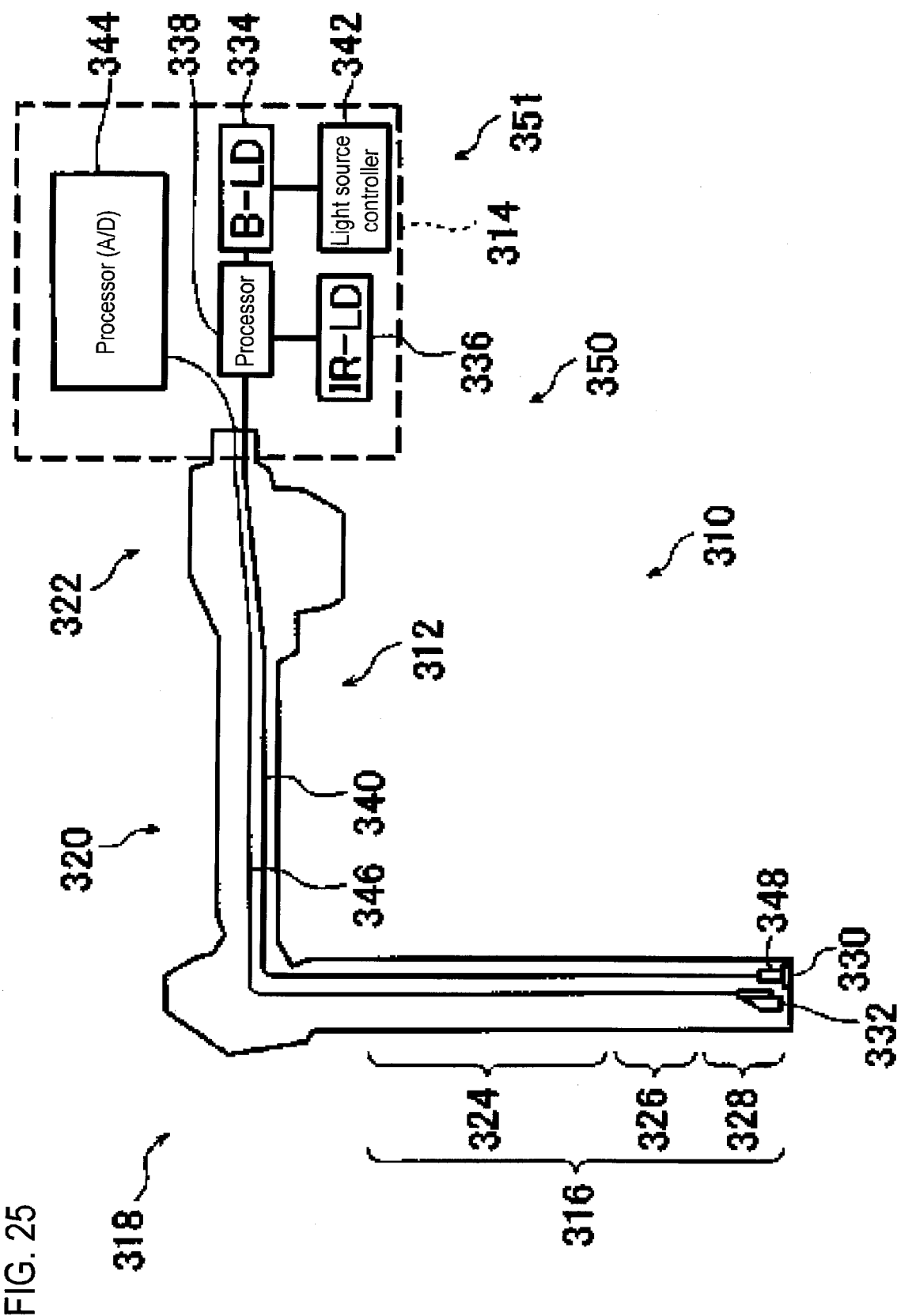
FIG. 25 is a schematic sectional view illustrating the endoscope apparatus according to a fifth embodiment of the invention that uses a light source device.
Figure 26:
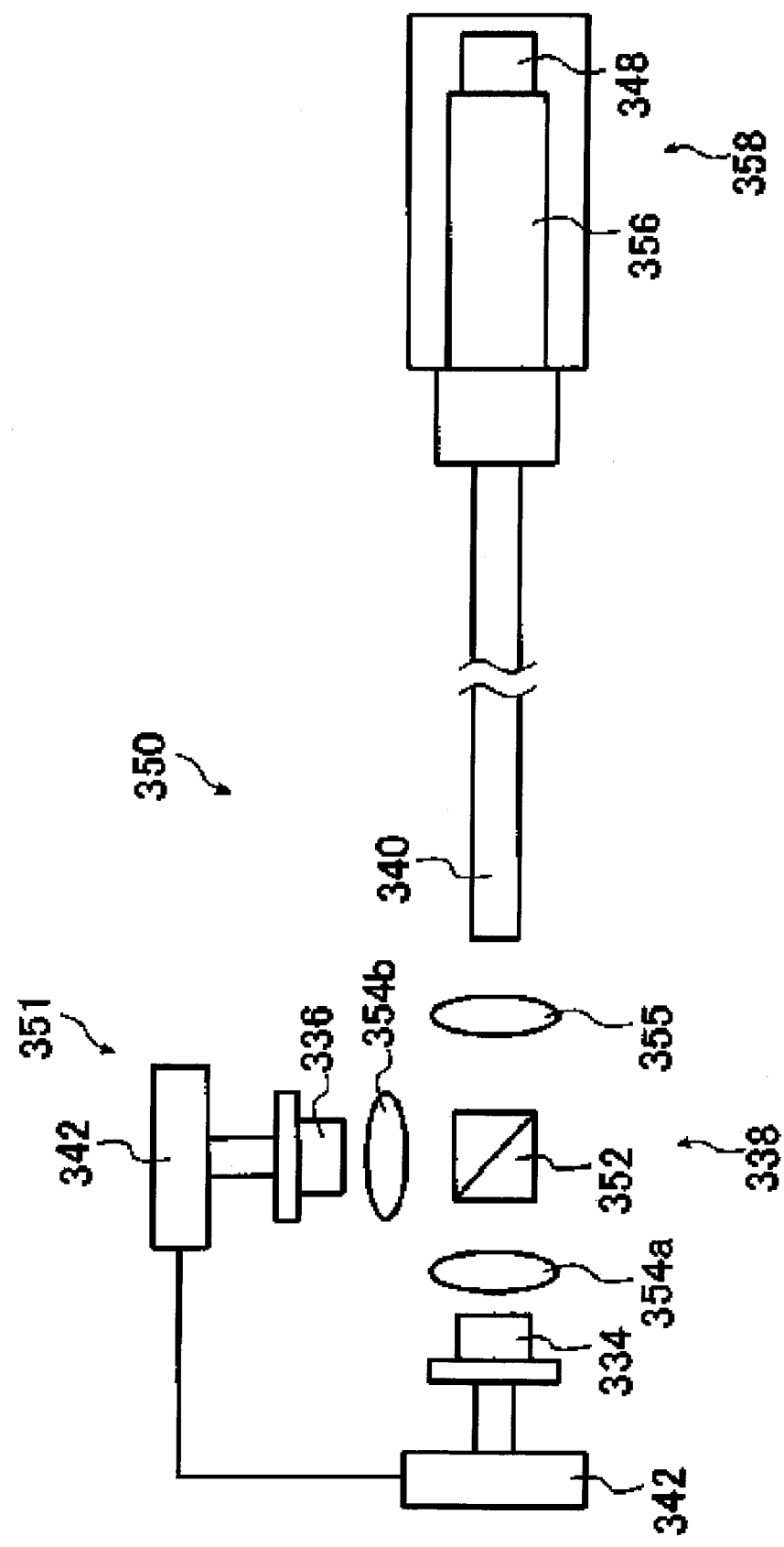
FIG. 26 is a schematic view illustrating details of the light source device for use in the endoscope apparatus shown in FIG. 25.

FIG. 25 is a schematic sectional view illustrating an endoscope apparatus that uses a light source device according to a fifth embodiment. FIG. 26 is a schematic view illustrating details of the light source device according to the fifth embodiment used in the endoscope apparatus shown in FIG. 25. An endoscope apparatus 310 shown in FIG. 25 has an endoscope 312 and a control device 314. FIG. 25 shows the schematic sectional view of the endoscope 312, and also shows the arrangement of an optical system in the endoscope 312 and an optical path. The endoscope 312 is a so-called electronic endoscope which has a small television camera (CCD) built on the tip and transmits acquired image information as an electric signal to the control device 314.

The endoscope 312 is configured to include: an insertion portion 316 inserted into the body; an operation portion 318 for performing an angle operation of the tip of the insertion portion 316 and operations such as suction, gas delivery, and water delivery from the tip of the insertion portion 316; a connector portion 322 for connecting the endoscope 312 to the control device 314; and a main body operation portion 320 that connects the operation portion 318 with the connector portion 322. In addition, the scale of the endoscope 312 in FIG. 25 is adjusted so as to facilitate understanding and is different from the actual scale. For example, in practice, the insertion portion 316 is very thin as compared with other portions and has a length sufficient to reach a part to be observed. Moreover, although not shown, a forceps channel for inserting an instrument for tissue extraction, channels for gas delivery and water delivery, and the like are provided in the endoscope 312 in addition to the image optical system.

The insertion portion 316 is configured to include a flexible soft portion 324, an angle portion 326, and a tip portion 328. An irradiation port 330 through which light is irradiated to the part to be observed, an imaging device (CCD) 332 for acquiring image information of the observed part, and an objective lens (not shown) are provided in the tip portion 328. The angle portion 326 is provided between the soft portion 324 and the tip portion 328 and is bent by a wire operation from the operation portion 318, an actuation operation of an actuator, and the like. The angle portion 326 can be bent in an arbitrary angle set according to a part for which the endoscope 312 is used, for example, 0° to 210° upward, 0° to 90° downward, 0° to 100° leftward, and 0° to 100° rightward. By bending the angle portion 326, the irradiation port 330 and the imaging device 332 of the tip portion 328 can be made to face a target position to be observed. The minimum bending radius of the angle portion 326 is set to R7.5 mm, for example.

The control device 314 has: a blue laser diode (hereinafter, referred to as an LD) (B-LD) 334 and an infrared LD 336 (IR-LD), which are two semiconductor laser light sources (semiconductor light emitting devices) and serve as light sources of excitation light; an optical path adjusting section 338 for making blue light from the blue LD 334 and infrared light from the infrared LD 336 be incident onto one optical fiber 340 (which will be described later); a light source controller 342 that controls the blue LD 334 and the infrared LD 336 to emit light in a time-series manner; and a processor 344. The processor 344 converts an electric signal (imaging signal) transmitted from the endoscope 312 into a digital image signal (video signal), performs image processing on the digital image signal, and supplies the digital image signal to an image output device (not shown), such as a television or a monitor.

One optical fiber 340 and one scope cable 346 are inserted inside the endoscope 312, and the imaging device 332 is attached to the tip of the scope cable 346. A base end of the optical fiber 340 is connected to the optical path adjusting section 338 since the connector portion 322 at the hand side (base end side) of the endoscope 312 is connected to the control device 314. The optical fiber 340 serves to guide the blue light from the blue LD 334 and the infrared light from the infrared LD 336 toward the tip of the endoscope 312 through the optical path adjusting section 338. The optical fiber 340 is inserted in the endoscope 312. One end (base end) of the optical fiber 340 is connected to the optical path adjusting section 338 of the control device 314, and the other end (tip) extends from the connector portion 322 of the endoscope 312 to the tip portion 328 of the insertion portion 316 through the main body operation portion 320.

Near the irradiation port 330 of the tip portion 328 of the insertion portion 316 of the endoscope 312, a phosphor portion 348 (an example of a wavelength conversion member) which is covered with one or more phosphors or includes one or more phosphors is disposed with being attached to the tip of the optical fiber 340. In the tip portion 328 of the endoscope 312, the tip of the optical fiber 340 extends to the position of the phosphor portion 348. Accordingly, the blue light from the blue LD 334 is incident on the phosphor portion 348 and is then emitted from the irradiation port 330 as white light (or pseudo white light) that becomes illumination light. Also, the infrared light from the infrared LD 336 is incident on the phosphor portion 348, is transmitted through the phosphor portion 348 as it is, preferably, without being absorbed by the phosphor portion 348 and without being subject to the wavelength conversion, and is emitted from the irradiation port 330. Moreover, the scope cable 346 is a cable for transmission of an imaging signal. Since the connector portion 322 of the endoscope 312 is connected to the control device 314, one end (base end) thereof is connected to the processor 344, and the other end (tip) thereof is connected to the imaging device 332. Image information acquired by the imaging device 332 is transmitted to the processor 344 through the scope cable 346 and is subjected to image processing. Then, the image information is converted into certain display image information and is displayed on an image output device (not shown), such as a television or a monitor.

In this embodiment, the blue excitation light which is emitted from the blue LD 334 and is then incident on the optical fiber 340 through the optical path adjusting section 338 is transmitted to the phosphor portion 348 through the optical fiber 340 so as to excite the phosphor portion 348. The phosphor portion 348 converts a part of the blue excitation light into fluorescent light having a different wavelength from the blue excitation light and emits the fluorescent light while making the remaining excitation light transmit therethrough. The fluorescent light and the excitation light emitted from the phosphor portion 348 are mixed to obtain white illumination light, for example. This white illumination light is emitted from the irradiation port 330 and is irradiated to the part to be observed. On the other hand, the infrared light which is emitted from the infrared LD 336 and is then incident on the optical fiber 340 through the optical path adjusting section 338 is transmitted to the phosphor portion 348 through the optical fiber 340, passes through the phosphor portion 348, is emitted from the irradiation port 330, and is irradiated to the part to be observed.

That is, the blue excitation light and the infrared light emitted from the blue LD 334 and the infrared LD 336, respectively, are incident on the optical fiber 340 along the optical path through the optical path adjusting section 338, are guided by the optical fiber 340, and are introduced into the phosphor portion 348. The blue excitation light introduced into the phosphor portion 348 excites the phosphor of the phosphor portion 348 to be converted into white (or pseudo white) light and is then emitted as white (or pseudo white) light from the irradiation port 330. The infrared light introduced into the phosphor portion 348 is transmitted through the phosphor portion 348 as it is if possible, preferably, without being absorbed by the phosphor portion 348 and without being subject to the wavelength conversion, and is emitted as infrared light from the irradiation port 330. Here, the blue LD 334, the infrared LD 336, the optical path adjusting section 338, the optical fiber 340, the light source controller 342, and the phosphor portion 348 constitute the light source device 350 of this embodiment.

Here, FIG. 26 shows details of the light source device 350 of this embodiment used in the endoscope apparatus 310 shown in FIG. 25. As shown in FIG. 26, the light source device 350 includes: the blue LD 334 which emits the blue excitation light; the infrared LD 336 which emits the infrared light in a direction perpendicular to the emission direction of the blue excitation light; a dichroic mirror 352 which is disposed at a position where the blue excitation light from the blue LD 334 and the infrared light from the infrared LD 336 cross each other and which allows the blue excitation light to transmit therethrough and causes the infrared light to be reflected toward a direction perpendicular thereto so that an optical path of the infrared light is made to match an optical path of the blue excitation light; collimator lenses 354a, 354b disposed between the dichroic mirror 352 and the blue LD 334, the infrared LD 336, respectively; the optical fiber 340 an incidence end of which is disposed on an extending line of one matched optical path of the infrared light and the blue excitation light; a condensing lens 355 disposed between the dichroic mirror 352 and the optical fiber 340; a holding end portion 356 which holds a tip portion of the optical fiber 340; and the phosphor portion 348 attached to the tip of the optical fiber 340 held by the holding end portion 356. Here, the blue LD 334, the infrared LD 336, the optical path adjusting section 338, and the light source controller 342 constitute the light source section 351.

Here, the dichroic mirror 352, the collimator lenses 354a and 354b, and the condensing lens 355 constitute the optical path adjusting section 338. Also, the holding end portion 356, which holds the tip of the optical fiber 340, and the phosphor portion 348 constitute an illumination optical member 358. In addition, the blue LD 334 is an example of a first light emitting device, and the blue excitation light is an example of excitation light having a first wavelength. In addition, the infrared LD 336 is an example of a second light emitting device, and the infrared light is an example of light having a second wavelength different from the first wavelength of the blue excitation light. In addition, the illumination optical member 358 is an example of a third light emitting device, and the white light or the pseudo white light is an example of first fluorescent light which is obtained by wavelength conversion in the phosphor portion 348 excited by blue excitation light, which is emitted from the phosphor portion 348m and which has a different emission wavelength from the first wavelength.

As the blue LD 334, for example, a semiconductor blue laser light source having a wavelength of 445 nm may be used. As a phosphor of the phosphor portion 348, for example, a YAG (YAG:Ce) (fluorescence wavelength of 530 to 580 nm) based yellow phosphor or α-SiALON and CaAlSiN$_3$ which emits light in a red region may be used. When a phosphor of the phosphor portion 348 is excited by blue light from the semiconductor laser light source as excitation light, fluorescent light ranging from yellow to red or fluorescent light ranging from red to green converted by the phosphor of the phosphor portion 348 and blue excitation light transmitted through the phosphor portion 348 are emitted from the phosphor portion 348. By mixing of the two types of light, white emission can be obtained from the irradiation port 330. On the other hand, for example, a semiconductor laser light source having a wavelength of 785 nm may be used as the infrared LD 336. Infrared light from such a semiconductor laser light source seldom excites the phosphor of the phosphor portion 348. Accordingly, the amount of fluorescent light converted by the phosphor of the phosphor portion 348 is small, and the most part of the infrared light transmits through the phosphor portion 348. That is, in the case of using YAG (YAG:Ce$^2$) as a phosphor in this embodiment, light is almost not absorbed when a wavelength exceeds 520 nm, such that the phosphor does not emit light. Moreover, the phosphor does not emit light at all if the wavelength of the light source is in the long wavelength side (exceeding 550 nm) in the emission spectrum.

In this embodiment, a purple-blue to blue semiconductor laser light source having a wavelength of 400 to 550 nm, preferably 400 to 500 nm may be used as the blue LD 334. Moreover, in this embodiment, a red to infrared semiconductor laser light source having a wavelength of 630 nm or more, preferably 630 to 800 nm, more preferably 650 to 800 nm may be used as the infrared LD 336. Moreover, in this embodiment, a blue light excitation green-yellow phosphor (Ca, Sr, Ba)$_2$SiO$_4$:Eu$^{2+}$ (fluorescence wavelength of 500 to 580 nm), SrGa$_2$S$_4$:Eu$^{2+}$, α-SiALON:Eu$^{2+}$, Ca$_3$Sc$_2$Si$_3$O$_{12}$:Ce$^{3+}$, a blue light excitation red phosphor (Ca, Sr, Ba)$_2$Si$_5$N$_8$:Eu$^{2+}$, CaAlSiN$_3$:Eu$^{2+}$, and the like may be used as a phosphor of the phosphor portion 348.

Figure 35A:
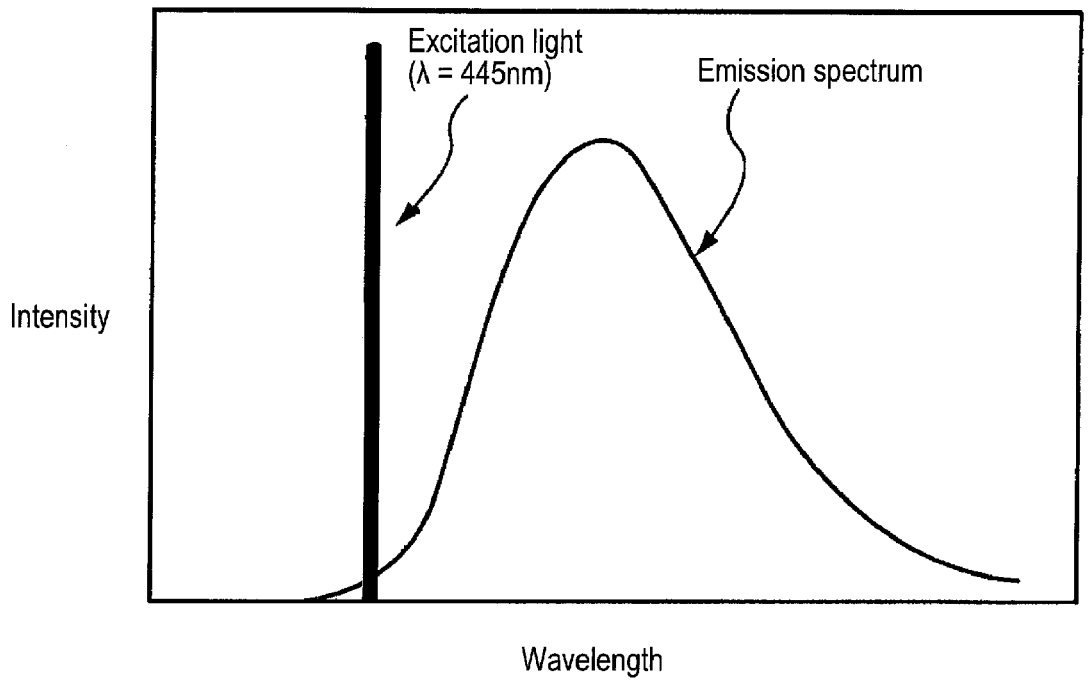
FIG. 35A schematically shows an emission spectrum of fluoroaluminum silicate glass doped with Yb and Er when it is excited by light having 425 nm in wavelength.
Figure 35B:
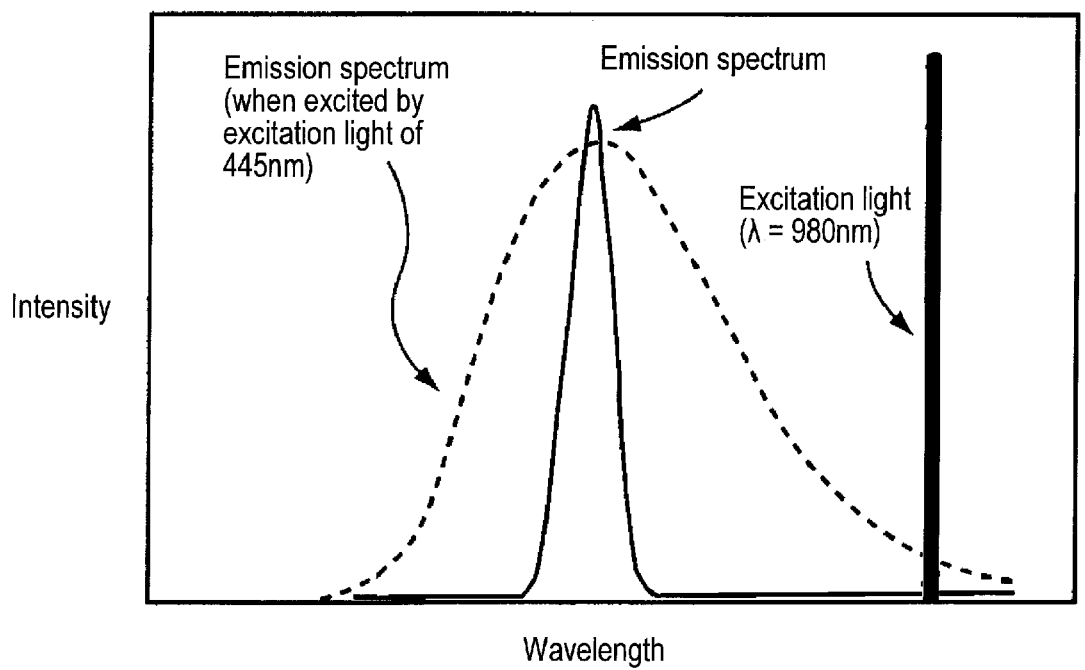
FIG. 35B schematically shows an emission spectrum of fluoroaluminum silicate glass doped with Yb and Er when it is excited by light having 850 nm in wavelength.

In this embodiment, an energy of fluorescent light (an example of second fluorescent light) which is emitted from the phosphor portion 348 due to excitation by infrared light having a certain energy is 1/10 or less, preferably 1/100 or less, more preferably 1/10,000 or less of an energy of fluorescent light (an example of first fluorescent light) which is emitted from the phosphor portion 348 due to excitation by blue excitation light having the certain energy. FIG. 35A schematically shows an emission spectrum of fluoroaluminum silicate glass doped with Yb and Er when it is excited by light having 445 nm in wavelength, and FIG. 35B schematically shows an emission spectrum (center wavelength of 550 nm) of fluoroaluminum silicate glass doped with Yb and Er when it is excited by light having 980 nm in wavelength. In the example shown in FIGS. 35A and 35B, it is assumed that the excitation light of 445 nm and the excitation light of 980 nm have the same energy. Since 445 nm (an example of blue excitation light) is in the excitation spectrum of fluoroaluminum silicate glass doped with Yb and Er, fluoroaluminum silicate glass doped with Yb and Er emits fluorescence light having a broad wavelength band as shown in FIG. 35A. On the other hand, when fluoroaluminum silicate glass doped with Yb and Er is excited by the excitation light of 980 nm (an example of infrared light), it also emits fluorescence light having a narrow wavelength band as shown in FIG. 35B. Although the peak of the fluorescence light caused by the excitation light of 980 nm shown in FIG. 35B is higher than that of the fluorescence light caused by the excitation light of 445 nm shown in FIG. 35A, the band of the fluorescence light caused by the excitation light of 980 nm is narrower than that of the fluorescence light caused by the excitation light of 445 nm Therefore, in this example, the area defined by the emission spectrum shown in FIG. 35B and the abscissa axis of FIG. 35B is equal to less than 1/10 of the area defined by the emission spectrum shown in FIG. 35A and the abscissa axis of FIG. 35A. That is, the energy of the fluorescence light of fluoroaluminum silicate glass doped with Yb and Er when it is excited by the light of 980 nm is equal to or less than 1/10 of the energy of the fluorescence light of fluoroaluminum silicate glass doped with Yb and Er when it is excited by the light of 445 nm.

Further preferably, the second fluorescent light is substantially neglected as compared with the first fluorescent light. That is, the infrared light introduced into the phosphor portion 348 passes through the phosphor portion 348 to be emitted as it is without being absorbed by the phosphor of the phosphor portion 348 and without being subject to the wavelength conversion. In addition, the phosphor of the phosphor portion 348 of the illumination optical member 358 is excited by blue excitation light. Then, the phosphor portion 348 causes the blue excitation light to be wavelength-converted so as to emit fluorescent light, which is emitted as white light or pseudo white light. In this case, light obtained by mixing of the wavelength-converted fluorescent light and the blue excitation light may be white light or pseudo white light, or the wavelength-converted fluorescent light itself may be the white light or pseudo white light.

Here, in consideration of a refractive index difference between the phosphor portion 348 and a fixing resin that forms a part of the phosphor, the phosphor portion 348 is preferably made of a material which is small in absorption and is large in scattering in an infrared region, so that the effect that the phosphor portion 348 causes light in a red or infrared region to scatter may be additionally achieved. In this way, a concave lens for increasing a divergence angle of infrared light, which is required at the tip of an optical fiber 428 for guiding infrared light like the light source 440 of the related art shown in FIG. 33, can be made unnecessary. That is, by appropriately selecting phosphor glass, aggregate, a binder, and the like which constitute the phosphor portion 348, a function of expanding the divergence angle of light as a scatterer for red light or infrared light can be given to the phosphor. This can prevent a phenomenon as an obstacle in imaging, such as a speckle generated by potential interference, when using a semiconductor laser light source. In addition, one of the preferable features of this embodiment is that the phosphor of the phosphor portion 348 can be used as a scatterer when infrared light is caused to pass therethrough.

Furthermore, in this embodiment, the blue LD 334 is used as the first light emitting device, the infrared LD 336 is used as the second light emitting device, and the phosphor portion 348 emitting fluorescent light, which will be white light, in response to blue excitation light from the blue LD 334 is used as the third light emitting device. However, the invention is not limited thereto. For example, two semiconductor laser light sources having different wavelengths may be used as the first and second light emitting devices, and the third light emitting source including the phosphor portion made of a phosphor excited by excitation light from one of the semiconductor laser light sources may be used, so that fluorescent light having a different wavelength from the excitation light can be emitted from the third light emitting source. Any semiconductor laser light source and any phosphor may be used so long as fluorescent light emitted from the phosphor excited by light from the other semiconductor laser light source is 1/10 or less of fluorescent light from the third light emitting source. The light conversion efficiency may be improved by using as the first light emitting device, for example, a semiconductor laser light source which is satisfactory in excitation efficiency of a phosphor and emits purple-blue light having a wavelength of 405 nm. Thus, since the amount of heat emission of the phosphor portion 348 can be suppressed, stable light emission can be realized. In addition, illumination light of a color corresponding to the object of observation using the endoscope 312 may be obtained by selecting the wavelength of excitation light of a semiconductor laser light source and the physical properties of the phosphor of the phosphor portion 348.

As described above, in case of using YAG (YAG:$Ce^{2+}$) as a phosphor, light is seldom absorbed if a wavelength of the light exceeds 520 nm, such that the phosphor does not emit fluorescence. Moreover, the phosphor does not emit fluorescence at all if the wavelength of the excitation light is on the long wavelength side of the emission spectrum (exceeding 550 nm). Moreover, assuming that a green SHG laser is guided through the optical fiber 340, the case where the phosphor 348 exists at the tip and the case where not phosphor 348 is provided will be compared. In the latter case, the speckle interference is hardly seen. This is because a speckle is not generated by refraction, reflection, diffusion, and the like due to a refractive index difference between the phosphor and a resin or a glass that is used when fixing the phosphor. Since the transmittance of the green laser at this time exceeds 50 to 60%, it can be sufficiently used. Undoubtedly, in a longer wavelength than the emission spectrum, there is no absorption by the phosphor. Up to an infrared wavelength region (~1500 nm), the fixing resin, for example, epoxy resin or silicon resin and glass causes no problem.

Moreover, in this embodiment, a part of input light components (excitation light) from a light source is wavelength-converted by the phosphor of the phosphor portion 348. However, output light of a desired color suitable for observation may be obtained by selecting a phosphor so that all of the input light components are wavelength-converted. That is, in the above example, a phosphor is excited by blue light, a part of the blue light component is converted into light of yellow-green and red, and the remaining blue light (transmitted light) is mixed therewith to generate white color as described above. However, in order to further increase the color rendering properties, it is desirable to use two or more types of phosphors, and to excite phosphors of three colors of RGB, for example, by purple light to ultraviolet light (400 nm or less, for example, 380 nm or 365 nm). Moreover, by increasing the number of types of phosphors by adding an orange color to RGB, for example, output light with higher color rendering properties can be obtained.

Figure 27:
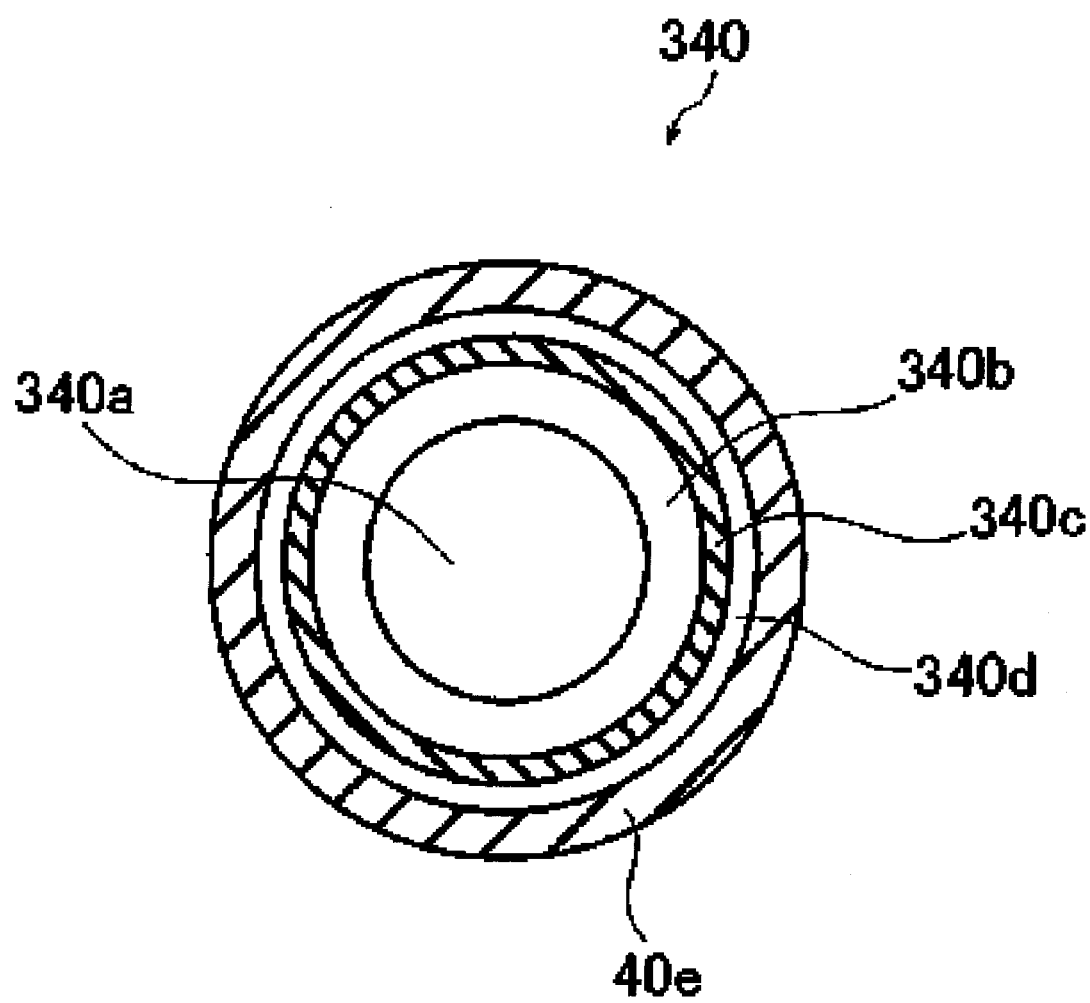
FIG. 27 is a schematic sectional view illustrating an optical fiber used in the light source device shown in FIG. 26.

The optical fiber 340 may be a material which can guide both the blue excitation light and the infrared light efficiently, and may be an optical fiber having a single core and having the same configuration. FIG. 27 shows a sectional configuration of the optical fiber 340. The optical fiber 340 has a core 340a, a clad 340b, a hard clad 340c, a polyimide reinforcement member 340d, and a Teflon (registered trademark) coating 340e sequentially from the central portion. For example, assuming that the diameter of the core 340a is 200 μm, that the thickness of the clad 340b is 35 μm, that the thickness of the hard clad 340c is about 5 μm, that the thickness of the polyimide reinforcement member 340d is 5 to 10 μm, and that the thickness of the Teflon (registered trademark) coating 340e is about 100 μm, the diameter of the optical fiber 340 becomes about 0.3 to 0.5 mm This corresponds to half or less of the diameter of a light guide of the related art. If an optical fiber having a single core is used as the optical fiber 340, the strength can be substantially increased because there is no friction between optical fibers unlike the light guide of the related art using a bundle of optical fibers. In addition, drop in light output with time due to damage of the optical fiber that is caused by repeated use can be prevented. Furthermore, it becomes possible to make the insertion portion 328 of the endoscope 312 significantly thin or to make the bending radius small.

Figure 33:
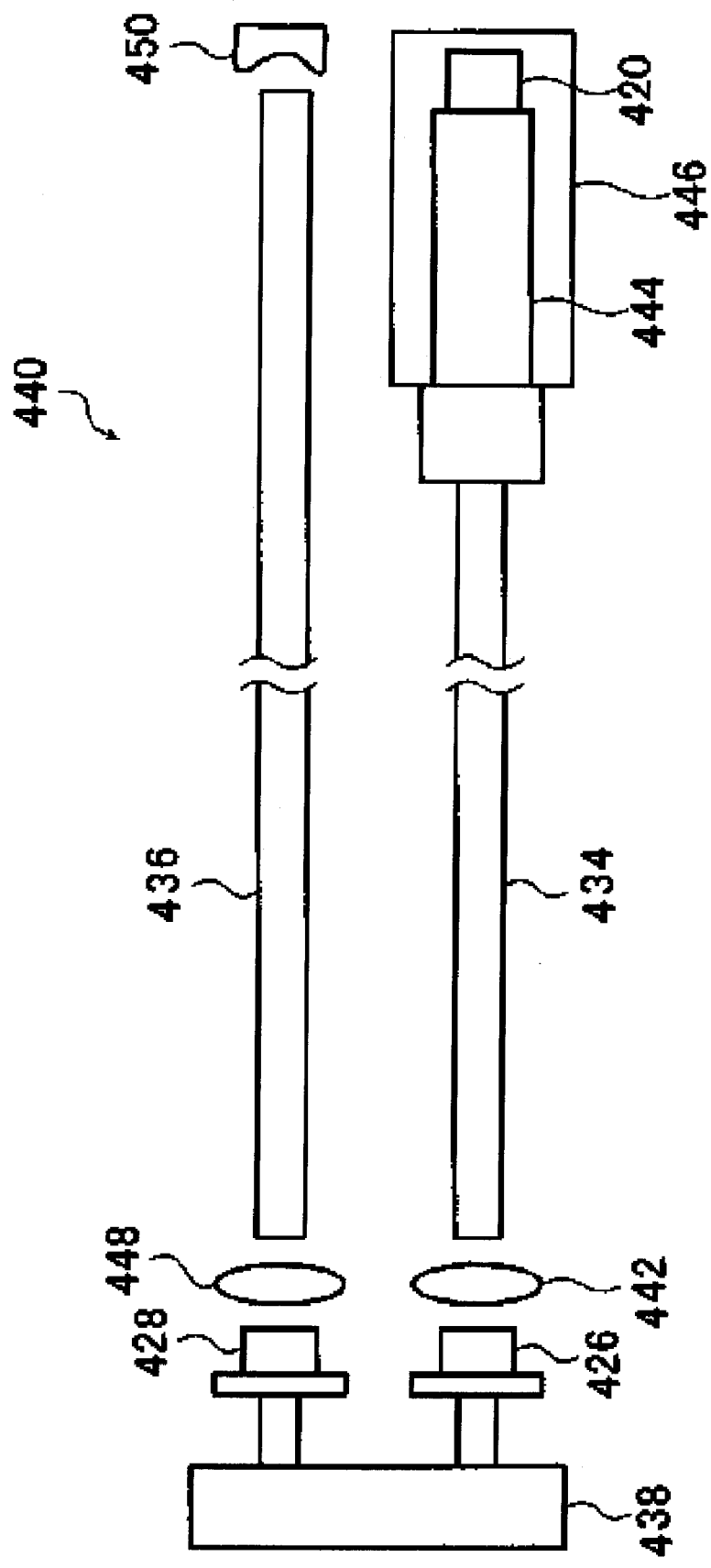
FIG. 33 is a schematic sectional view illustrating details of a light source device of the related art used in the endoscope apparatus shown in FIG. 32.

Meanwhile, since the optical fiber 426 which is used in the light source device 440 of the related art shown in FIG. 33 and which guides blue excitation light to the phosphor portion 420 disposed at the tip is dedicated to blue excitation light, the blue excitation light can be guided through the optical fiber 426 efficiently, for example, with the efficiency of 90% or more. However, infrared light cannot be transmitted through the optical fiber 426. On the other hand, since the optical fiber 340 shown in FIG. 27 is required to guide both the blue excitation light and the infrared light, for example, a magnesium oxide is mixed in the core 340a as an additive for allowing the infrared light to transmit therethrough. Since the magnesium oxide is mixed, the optical fiber 340 can guide the blue excitation light only with the efficiency of 85 to 86%. Accordingly, although the efficiency is decreased a little, the infrared light can be guided similarly.

In addition, any optical fiber which can guide both blue excitation light and infrared light may be used as the optical fiber 340 of this embodiment. In addition, any additive that gives to the optical fiber 340 a function of allowing both blue excitation light and infrared light to transmit through the optical fiber 340 may be used as the additive that is mixed in the core 340a of the optical fiber 340 in order to allow infrared light to transmit therethrough.

Then, the dichroic mirror 352 is included in the optical path adjusting section 338 and serves as a transflective mirror which causes blue excitation light emitted from the blue LD 334 to transmit therethrough, reflects infrared light emitted from the infrared LD 336 in the perpendicular direction, and matches an optical path of the infrared light with an optical path of the blue excitation light. In the above example, the dichroic mirror 352 is disposed at the position on an optical path of the blue excitation light emitted from the blue LD 334, where the blue excitation light from the blue LD 334 and the infrared light from the infrared LD 336 cross each other. In addition, the dichroic mirror 352 is not limited to one used in the above example, but may be a mirror which reflects the blue excitation light emitted from the blue LD 334, causes the infrared light emitted from the infrared LD 336 to transmit therethrough, and matches the optical path of the infrared light with the optical path of the blue excitation light. The collimator lenses 354a and 354b are included in the optical path adjusting section 338 and serve to make blue excitation light from the blue LD 334 and infrared light from the infrared LD 336 condensed on the incidence surface of the dichroic mirror 352. Accordingly, the collimator lenses 354a and 354b are formed of convex lenses. In addition, the condensing lens 355 is also included in the optical path adjusting section 338 and serves to make infrared light and blue excitation light emitted from the dichroic mirror 352 condensed on the incidence surface of the optical fiber 340. Accordingly, the condensing lens 355 is formed of a convex lens.

The holding end portion 356 is included in the illumination optical member 358 and serves to support the tip portion of the optical fiber 340 so as to attach the phosphor portion 48 to the tip portion. The illumination optical member 358 includes the tip portion of the optical fiber 340, the phosphor portion 48, and the holding end portion 356. The illumination optical member 358 serves to cause white light to be emitted from the phosphor portion 48 and also cause infrared light to be emitted. In addition, the light source controller 342 serves to control the blue LD 334 and the infrared LD 336 to emit light in a time-serial manner. In the light source device 350 of this embodiment, when the blue LD 334 is turned on, the light reaches the phosphor portion 48 at the tip of the optical fiber 340 through the dichroic mirror 352, the collimator lenses 354a and 354b for condensing the light on the incidence surface of the optical fiber 340, and the condensing lens 355. At this time, white light is obtained by (i) the blue excitation light and (i) light of yellow to red from the phosphor in the phosphor portion 48. If necessary, the infrared LD 336 is turned on to emit infrared light.

[Sixth Embodiment]

Figure 28:
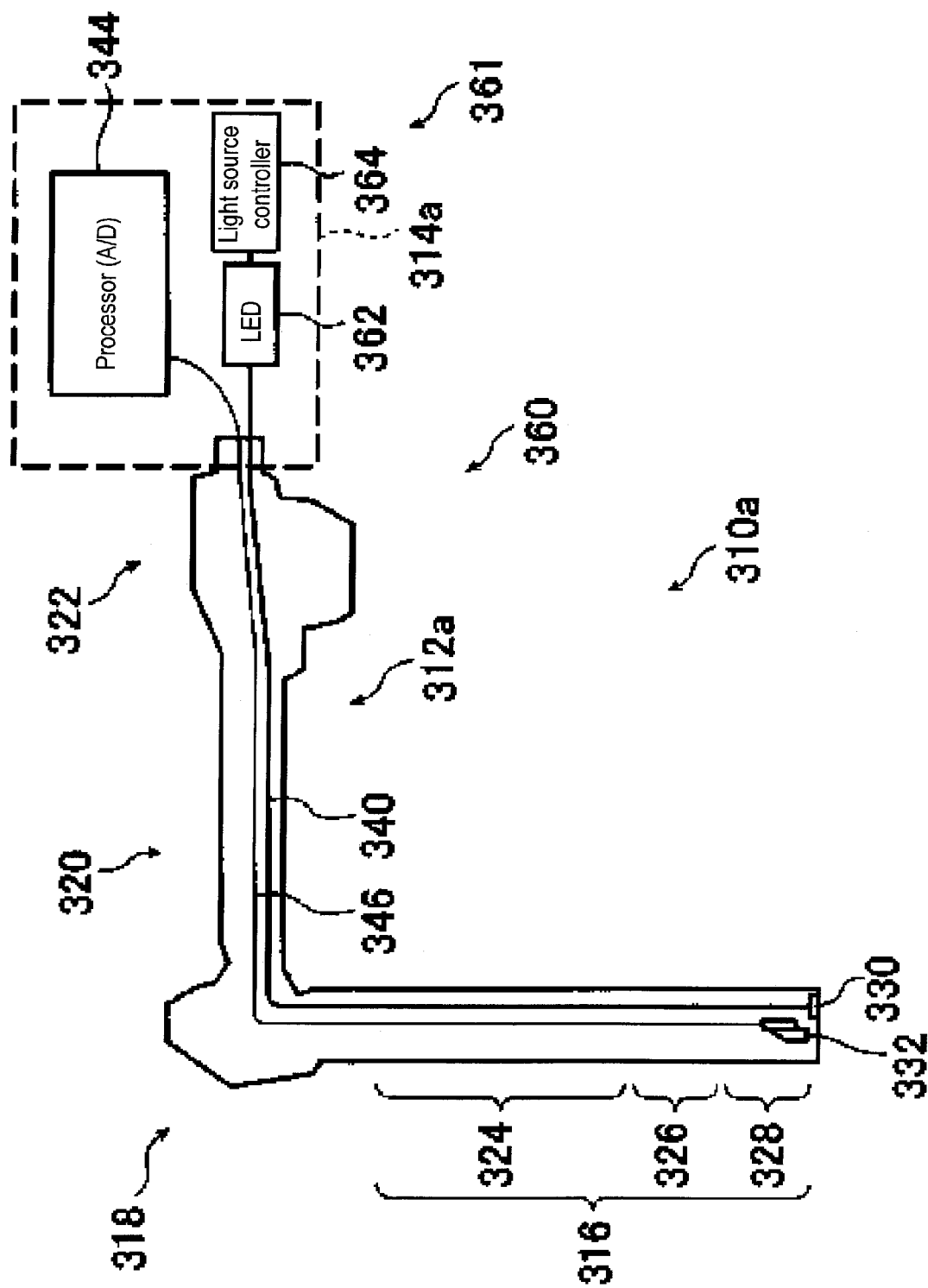
FIG. 28 is a schematic sectional view illustrating the endoscope apparatus according to a sixth embodiment of the invention that uses the light source device.
Figure 29:
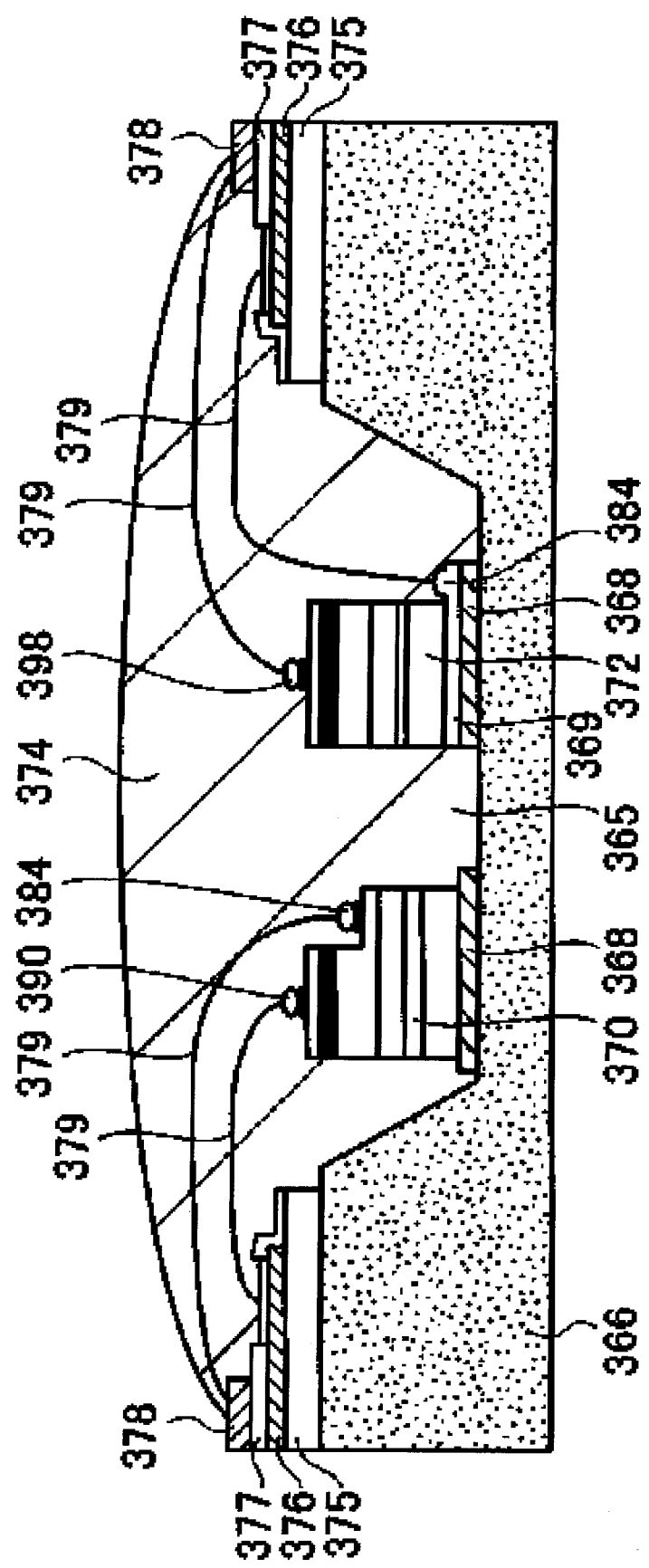
FIG. 29 is a schematic sectional view illustrating details of the light source device for use in the endoscope apparatus shown in FIG. 28.
Figure 30:
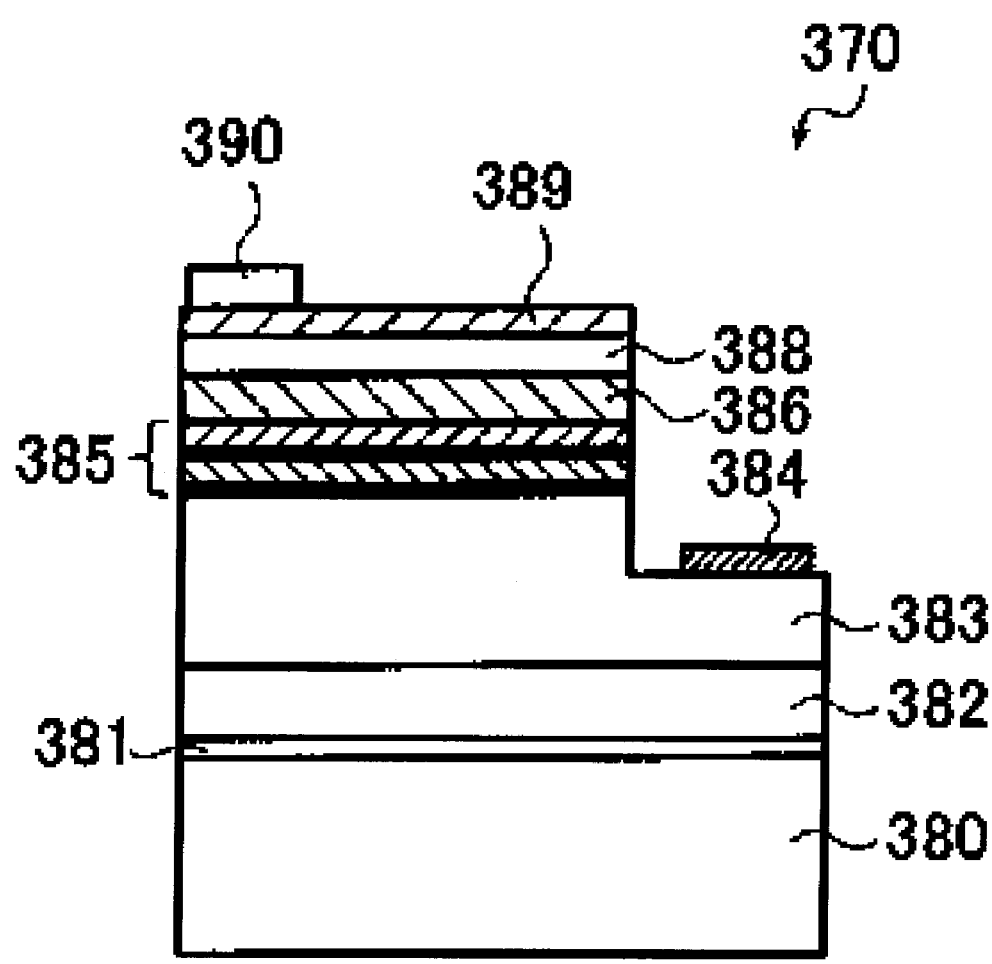
FIG. 30 is a schematic sectional view illustrating a blue LED device used in the light source device shown in FIG. 29.
Figure 31:
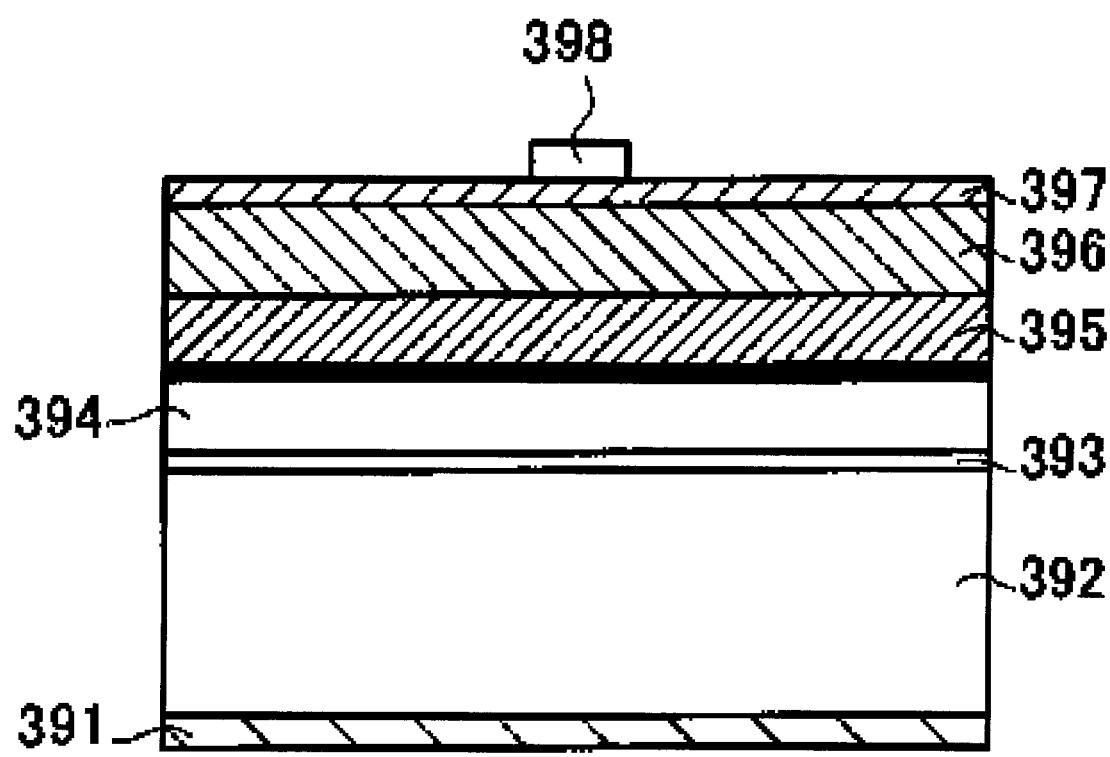
FIG. 31 is a schematic sectional view illustrating an infrared emission LED device used in the light source device shown in FIG. 29.
Figure 32:
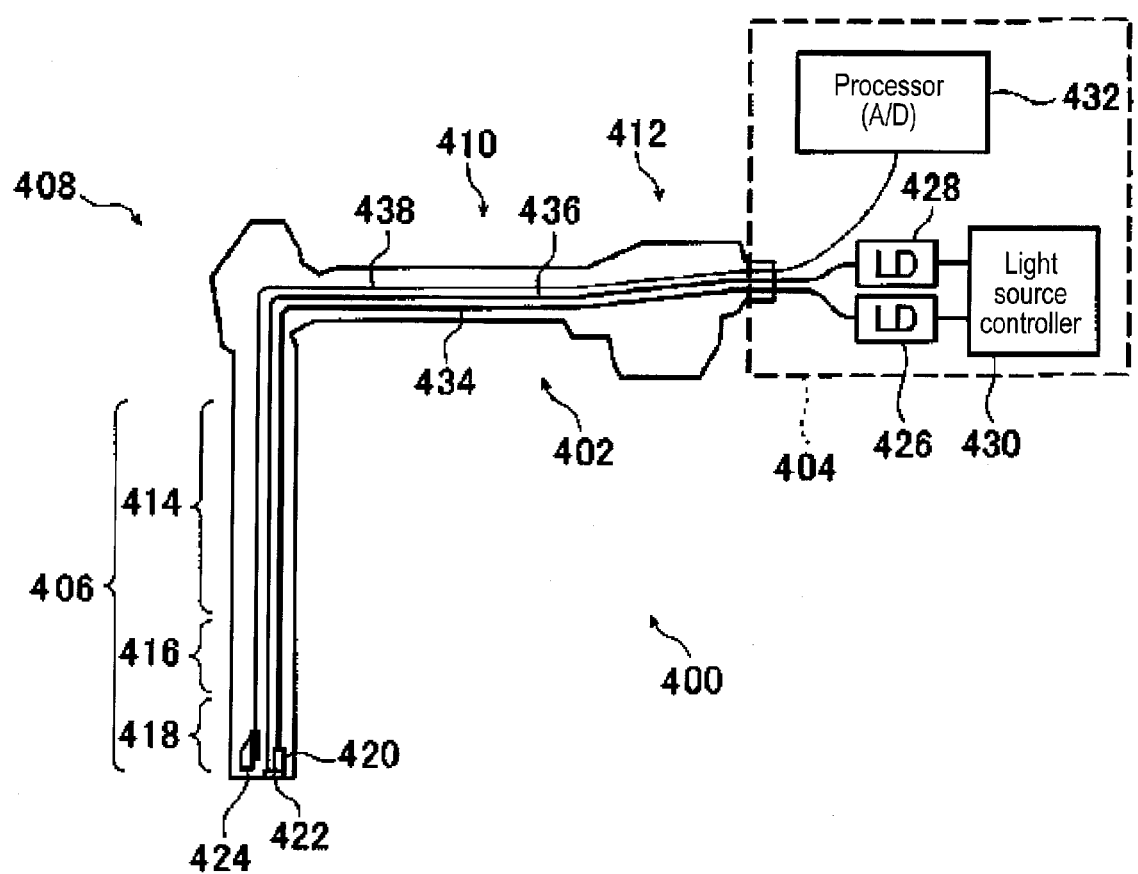
FIG. 32 is a schematic sectional view illustrating an endoscope apparatus of a related art.

Next, a sixth embodiment of the invention will be described. FIG. 28 is a schematic sectional view illustrating an endoscope apparatus that uses a light source device according to the sixth embodiment. FIG. 29 is a schematic view illustrating details of the light source device according to the sixth embodiment used in the endoscope apparatus shown in FIG. 28. FIGS. 30 and 31 are schematic sectional views illustrating a blue LED device and an infrared emission LED device used in the light source device shown in FIG. 29. An endoscope apparatus 310a shown in FIG. 28 has the same configuration as the endoscope apparatus 310 shown in FIG. 25 except that the configuration of a light source section of a control device is different and that a phosphor portion is not provided in a tip portion of an endoscope. Accordingly, the same components are denoted by the same reference numerals, and detailed explanation thereon will be omitted, and different points will be mainly described.

The endoscope apparatus 310a shown in FIG. 28 has an endoscope 312a and a control device 314a. In a tip portion 328 of an insertion portion 316 of the endoscope 312a, a phosphor portion is not provided at the tip of an optical fiber 340, but the tip portion of the optical fiber 340 is directly connected to an irradiation port 330 at the tip of the tip portion 328 of the endoscope 312a. The control device 314a includes: a light source section 361 having a light source unit 362 that emits white light and infrared light and a light source controller 364 that performs control so that the white light and the infrared light are emitted in a time-series manner from the light source unit 362; and a processor 344. In addition, the light source section 361 including the light source unit 362 and the light source controller 364 and the optical fiber 340 form a light source device 360 of this embodiment.

As specifically shown in FIG. 29, the light source unit 362 includes: a common substrate 366 formed with a recess 365; a blue LED device 370 and an infrared emission LED device 372 fixed to the recess 365 by an adhesive 368; a resin sealing portion 374 which seals the blue LED device 370 and the infrared emission LED device 372, which are provided in the recess 365, in a sealing region with a phosphor-containing resin in which a phosphor is mixed. Here, on a bottom surface side of the infrared emission LED device 372, a gold layer 369 is formed. The gold layer 369 is fixed to the recess 365 of the common substrate 366 by the adhesive 368. On upper surfaces of both sides of the recess 365 of the common substrate 366, a copper layer 376 serving as a lower electrode is formed with an insulation layer 375 interposed between the copper layer 376 and the common substrate 366. Then, a resist layer 377 serving as an insulation layer is formed on the copper layer 376 so as to be opened to the copper layer 376, and a copper layer 378 is formed on the resist layer 377. An n-side electrode 384 serving as a lower electrode of the blue LED device 370 is bonded to the copper layer 376 by a gold wire 379, and a P-side electrode 390 serving as upper electrode is bonded to the copper layer 378 by the gold wire 379. In addition, a P-side electrode 391 serving as a lower electrode of the infrared emission LED device 372 is bonded to the copper layer 376 by the gold wire 379, and a P-side electrode 398 serving as upper electrode is bonded to the copper layer 378 by the gold wire 379.

Figure 34:
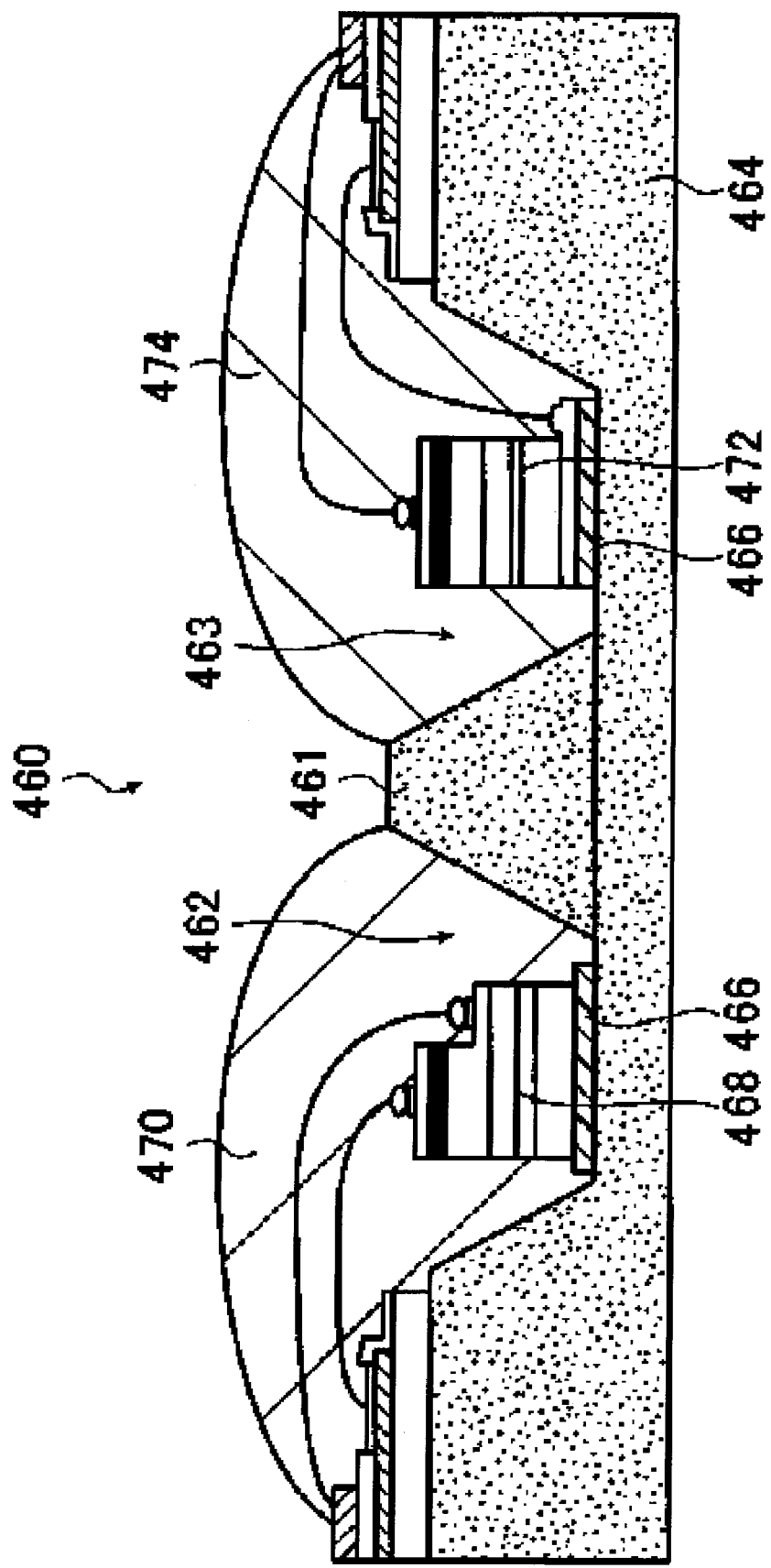
FIG. 34 is a schematic sectional view illustrating another example of a light source device of the related art in detail.

The mounting area can be reduced by similarly mounting a plural of LED chips, in the shown example, the blue LED device 370 and the infrared emission LED device 372 in the same place (recess 365) of the common substrate 366 and sealing them with the same resin including a phosphor. In a known device (light source device 460) shown in FIG. 34, the mounting area is increased because a blue LED device 468 which uses a phosphor-containing resin and an infrared emission LED device 472 which does not excite a phosphor are separately mounted and sealed. However, by mounting the blue LED device 370 and the infrared emission LED device 372 at the same place, the mounting area can be reduced compared with that in the known device. In addition, the light source controller 364 controls the blue LED device 370 and the infrared emission LED device 372 to emit light in a time-series manner similar to the light source controller 342 of the first embodiment.

The blue LED device 370 is an LED light source (semiconductor light emitting device) serving as an excitation light source and emits blue excitation light. In addition, the blue LED device 370 is an example of the first light emitting device, and the blue excitation light is an example of excitation light emitted in a first wavelength. As the blue LED device 370, for example, a blue LED light source with a wavelength of 440 to 460 nm may be used. As a phosphor mixed in a resin of the resin sealing portion 374, for example, a YAG (YAG:Ce) (fluorescence wavelength of 530 to 580 nm) based yellow phosphor may be used. When a phosphor of such a resin sealing portion 374 is excited by using blue light from such a blue LED light source as excitation light, fluorescent light of yellow color or ranging from yellow to red colors converted by the phosphor of the resin sealing portion 374 and blue excitation light transmitted through the resin sealing portion 374 are emitted from the resin sealing portion 374. By mixing of the two types of light, white emission can be obtained from the irradiation port 330. Accordingly, the blue LED device 370 and the resin sealing portion 374 in which a phosphor is mixed form a blue light excitation white LED.

On the other hand, the infrared emission LED device 372 is an LED light source (semiconductor light emitting device) serving as an excitation light source and emits infrared light. In addition, the infrared emission LED device 372 is an example of the second light emitting device, and the infrared light is an example of light emitted in a second wavelength different from the first wavelength of the blue excitation light. As the infrared emission LED device 372, for example, an infrared emission LED device light source with a wavelength of 780 nm may be used. Infrared light emitted from the infrared emission LED device light source seldom excites the phosphor in the resin sealing portion 374. Accordingly, the amount of fluorescent light converted by the phosphor in the resin sealing portion 374 is small and most of the infrared light is transmitted through the resin sealing portion 374.

In addition, the resin sealing portion 374 in which a phosphor excited by blue excitation light from the blue LED device 370 is mixed corresponds to the third light emitting device, and white light or pseudo white light corresponds to the first fluorescent light which is emitted from the resin sealing portion 374 with a different emission wavelength from the first wavelength after wavelength conversion in the resin sealing portion 374 excited by blue excitation light. That is, the blue LED device 370 and the resin sealing portion 374 formed of a phosphor-containing resin form a white (or pseudo white) LED, and white light (or pseudo white light) is emitted from the resin sealing portion 374. Moreover, the infrared emission LED device 372 emits infrared light and makes the infrared light transmitted through the resin sealing portion 374 so that the infrared light is emitted to the outside.

Similar to the above-described blue LD 334, a known purple-blue to blue LED light source with a wavelength of 400 to 550 nm, preferably 400 to 500 nm may be used as the blue LED device 370. Moreover, similar to the above-described infrared LD 336, a known red to infrared emission LED device light source with a wavelength of 630 nm or more, preferably 630 to 800 nm, more preferably 650 to 800 nm may be used as the infrared emission LED device 72.

Moreover, similar to the phosphor in the phosphor portion 48, a blue light excitation green-yellow phosphor $(Ca, Sr, Ba)_2SiO_4:Eu^{2+}$ (fluorescence wavelength of 500 to 580 nm), $SrGa_2S_4:Eu^{2+}$, $\alpha$-SiALON:$Eu^{2+}$, $Ca_3Sc_2Si_3O_{12}:Ce^{3+}$, a blue light excitation red phosphor $(Ca, Sr, Ba)_2Si_5N_8:Eu^{2+}$, $CaAlSiN_3:Eu^{2+}$, and the like may be used as a phosphor mixed in the resin sealing portion 374.

An energy of fluorescent light (an example of second fluorescent light) which is emitted from the resin sealing portion 374 formed of a phosphor-containing resin after excitation by infrared light having a certain energy is $1/10$ or less, preferably $1/100$ or less, more preferably $1/10,000$ or less of an energy of fluorescent light (an example of first fluorescent light) which is emitted from the resin sealing portion 374 after excitation by blue excitation light having the certain energy. Most preferably, the second fluorescent light is substantially neglected compared with the first fluorescent light. That is, most preferably, the infrared light transmitted through the resin sealing portion 374 passes through the resin sealing portion 374 to be emitted as it is without being absorbed by the phosphor of the resin sealing portion 374 and without wavelength conversion. In addition, the phosphor of the resin sealing portion 374 is excited by blue excitation light. Then, the resin sealing portion 374 makes the blue excitation light wavelength-converted to emit fluorescent light, which is emitted as white light or pseudo white light. In this case, light obtained by mixing of wavelength-converted fluorescent light and blue excitation light may be white light or pseudo white light, or the wavelength-converted fluorescent light itself may be the white light or pseudo white light.

Here, in consideration of a refractive index difference between the resin sealing portion 374 and a resin for fixing and solidification that forms a phosphor-containing resin, the resin sealing portion 374 is preferably formed of a material having a particle diameter, which is small in absorption and is large in scattering in an infrared region with respect to the phosphor itself and a filler, so that the effect that the resin sealing portion 374 makes light in a red or infrared region scatter may be added. In this way, the infrared emission LED device 472 which emits infrared light does not need to be separated from the blue LED device 468 which emits blue excitation light and be sealed with a resin not containing a phosphor unlike the light source device 460 shown in FIG. 34. That is, by appropriately selecting phosphor glass, aggregate, a binder, and the like which form the phosphor-containing resin of the resin sealing portion 374, a function of extending the divergence angle of light as a scatterer for red light or infrared light can be given to the phosphor. This can prevent a phenomenon as an obstacle in imaging, such as a speckle generated by potential interference, when using an LED light source. In addition, one of the features is that the phosphor of the resin sealing portion 374 can be used as a scatterer when making infrared light pass therethrough.

Furthermore, although the blue LED device 370 is used as the first light emitting device, the infrared emission LED device 372 is used as the second light emitting device, and the resin sealing portion 374 sealed with a phosphor-containing resin which emits fluorescent light becoming white light by blue excitation light from the blue LED device 370 is used as the third light emitting device in the shown example, the invention is not limited thereto. For example, two LED light sources with different wavelengths may be used as the first and second light emitting devices and a third light emitting source including a resin sealing section sealed with a phosphor-containing resin excited by excitation light from one of the LED light sources may be used, so that fluorescent light with a different wavelength from the excitation light can be emitted from the third light emitting source. Any LED light source and phosphor-containing resin may be used if fluorescent light emitted from the resin sealing section sealed with the phosphor-containing resin excited by light from the other LED light source is 1/10 or less of fluorescent light from the third light emitting source. Moreover, as the blue LED device 370, the infrared emission LED device 372, and the phosphor mixed in the resin sealing portion 374, those having the same functions and effects as the blue LD 334, the infrared LD 336, and the phosphor within the phosphor portion 48 in the first embodiment described above may be used.

Next, the configurations of the blue LED device 370 and the infrared emission LED device 372 will be described with reference to FIGS. 30 and 31. As shown in FIG. 30, the blue LED device 370 has a layer structure including: a sapphire substrate 380; an aluminum nitride (hereinafter, referred to as AlN) buffer layer 381 formed on the sapphire substrate 380; a non-doped gallium nitride (hereinafter, referred to as GaN) layer 382 formed on the AlN buffer layer 381; an Si-doped n-type GaN layer 383 formed on the non-doped GaN layer 382; an n-side electrode 384 which is formed on a part of the Si-doped n-type GaN layer 383 and serves as a lower electrode; a single quantum well layer (GaN/InGaN light emitting layer/GaN carrier confinement layer) 385 which is formed on the rest upper part of the Si-doped n-type GaN layer 383 and is formed by laminating a GaN quantum well barrier layer, in which suitable amount of Si and Mg are doped, and an indium gallium nitride (hereinafter, referred to as InGaN) layer which is a light emitting layer; an Mg-doped p-type AlGaN carrier block layer 386 formed on the single quantum well layer 385; a p-GaN layer 388 which is formed on the Mg-doped p-type AlGaN carrier block layer 386 and in which Mg is doped with high concentration; a p-side ITO electrode layer 389 formed on the p-GaN layer 388; and a p-side electrode 390 which is formed on the p-side ITO electrode layer 389 and serves as an upper electrode.

Such a blue (or green) LED 370 can be manufactured by the following manufacturing method. First, a sapphire substrate is prepared, and pretreatment on the prepared sapphire substrate is performed. Then, using metal organic chemical vapor deposition (MOCVD), an MN buffer layer, an Si-doped n-type GaN layer, a GaN quantum well barrier layer in which suitable amount of Si and Mg are doped, and an InGaN layer which is a light emitting layer are laminated, thereby forming a single quantum well layer. Then, an Mg-doped p-type AlGaN carrier block layer and a p-GaN layer in which Mg is doped with high concentration are grown. As a result, an LED wafer can be manufactured. Then, activation treatment of a p-type carrier is executed and photolithography, a deposition process of an ITO layer for electrode formation and a metal electrode for wire bonding, and an etching process are repeated. As a result, a normal LED wafer is manufactured. Then, scratching using a diamond scriber is performed between chips for separation of the chips and cleaving is performed by using breaking equipment, thereby completing element separation. In this way, the blue (or green) LED 370 can be manufactured.

As shown in FIG. 31, the infrared emission LED device 372 has a layer structure including: a p-side electrode 391 serving as a lower electrode; a p-type GaP substrate 392 formed on the p-side electrode 391; a Zn-doped p-type AlGaAs carrier block and electrode contact layer (p-AlxGal-xAs layer) 394 bonded onto the p-type GaP substrate 392 with an adhesive layer 393 interposed therebetween; an AlGaAs light emitting layer (p-AlyGal-yAs light emitting layer) 395 (x>y aluminum composition) which is formed on the Zn-doped p-type AlGaAs carrier block and electrode contact layer 394 and in which a suitable amount of Mg is doped; an Si-doped n-type AlGaAs layer (n-AlxGal-xAs layer) 396; a p-side ITO electrode layer 397 formed on the Si-doped n-type AlGaAs layer 396; and a p-side electrode 398 which is formed on the p-side ITO electrode layer 397 and serves as an upper electrode.

Such an infrared emission LED device 372 can be manufactured as follows. First, a GaAs substrate is prepared. Then, using the metal organic chemical vapor deposition (MOCVD), an Si-doped n-GaAs buffer layer, an Si-doped n-type AlGaAs layer (n-AlxGal-xAs layer), and an AlGaAs light emitting layer (p-AlyGal-yAs light emitting layer) in which a suitable amount of Mg is doped are laminated and formed on the prepared GaAs substrate. Then, a Zn-doped p-type AlGaAs carrier block and electrode contact layer (p-AlxGal-xAs layer) is grown up. Then, a p-side AlGaAs layer (p-AlxGal-xAs layer) and a p-type GaP substrate are bonded to each other, and the GaAs substrate used for growth of the p-AlxGal-xAs layer is removed. Then, similar to the case of the blue (or green) LED 370, a photolithography process, an ITO layer forming process, a metal electrode deposition process, and an etching process are repeated. As a result, a normal LED wafer is manufactured. Then, scratching using a diamond scriber is performed between chips for separation of the chips and cleaving is performed by using breaking equipment, thereby completing element separation. In this way, the infrared emission LED device 372 can be manufactured.

While the light source device and the endoscope using the light source device have been described in detail, the invention is not limited to the above embodiments but various improvements and changes may be made without departing from the scope and spirit of the invention. For example, the light source device of the invention may also be applied to the following endoscopes and applications other than endoscopes.

1. Endoscope, observation of blood vessel, measurement of blood flow, infrared fluorescence 2. Neurosurgery, orthopedics, otolaryngology, surgical navigation (for example, surgical navigation such as a product of Medtronic Sofamor Danek, Inc.)

3. Observation of blood vessel using infrared rays during operation (for example, blood vessel observation system using infrared rays during operation such as SPY system of NOVADQ)

4. Light source of system for observation of blood vessel of finger and blood flow rate 5. Pharmacokinetic observation system of animal (infrared fluorescence)

6. Measurement of masseteric oxygen state of dentistry and orthodontic dentistry, and determination of false-tooth plastics The foregoing description of the exemplary embodiments of the invention has been provided for the purposes of illustration and description. It is not intended to be exhaustive or to limit the invention to the precise forms disclosed. Obviously, many modifications and variations will be apparent to practitioners skilled in the art. For example, one skilled in the art would appreciate to combine any of the above embodiments with each other as a modification. The exemplary embodiments were chosen and described in order to explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An illumination device comprising
a light source including
 a first light source that emits light having a first wavelength,
 a second light source that emits light having a second wavelength different from the first wavelength, and
 a third light emitting device that has or is coated with one or more phosphors which are excited by the light emitted from the first light source to emit first fluorescent light having an emission wavelength different from the first wavelength
an energy of fluorescence light of the third light emitting device when the one or more phosphors of the third light emitting device are excited by the light having the second wavelength and having a certain energy is equal to or less than $1/10$ of that of fluorescence light of the third light emitting device when the one or more phosphors of the third light emitting device are excited by the light having the first wavelength and having the certain energy.

2. The light source device according to claim 1, wherein the energy of the fluorescence light of the third light emitting device when the one or more phosphors of the third light emitting device are excited by the light having the second wavelength and having the certain energy is equal to or less than $1/100$ of that of the fluorescence light of the third light emitting device when the one or more phosphors of the third light emitting device are excited by the light having the first wavelength and having the certain energy.

3. The light source device according to claim 2, wherein the energy of the fluorescence light of the third light emitting device when the one or more phosphors of the third light emitting device are excited by the light having the second wavelength and having the certain energy is equal to or less than $1/10{,}000$ of that of the fluorescence light of the third light emitting device when the one or more phosphors of the third light emitting device are excited by the light having the first wavelength and having the certain energy.

4. The light source device according to claim 1, wherein the fluorescence light of the third light emitting device when the one or more phosphors of the third light emitting device are excited by the light having the second wavelength and having the certain energy is substantially negligible as compared with the fluorescence light of the third light emitting device when the one or more phosphors of the third light emitting device are excited by the light having the first wavelength and having the certain energy.

5. The light source device according to claim 1, further comprising:
a first optical fiber that guides first excitation light emitted from the first light source, wherein
the one or more phosphors of the third light emitting device are disposed at an emission end of the first optical fiber, the fluorescent light emitted from the one or more phosphors excited by the first excitation light guided by the first optical fiber is mixed in the one or more phosphors of the third light emitting device and is then emitted from the third light emitting device, and
emission light of the second light source is emitted from the third light emitting device through the one or more phosphors of the third light emitting device.

6. The light source device according to claim 5, further comprising:
a second optical fiber that guides the emission light of the second light source, wherein
the one or more phosphors of the third light emitting device is disposed to be positioned at an emission end of the second optical fiber, and
the emission light of the second light source is guided by the second optical fiber and be then emitted from the third light emitting device through the one or more phosphors of the third light emitting device.

7. The light source device according to claim 6, wherein
the first and second optical fibers are the same one optical fiber,
the one optical fiber guides the first excitation light emitted from the first light source and the emission light of the second light source,
the one or more phosphors of the third light emitting device is disposed at the emission end of the one optical fiber,
the fluorescent light emitted from the one or more phosphors excited by the first excitation light guided by the one optical fiber is mixed in the one or more phosphors of the third light emitting device and is then emitted from the third light emitting device, and
the emission light of the second light source may be guided by the one optical fiber and is then emitted from the third light emitting device through the one or more phosphors of the third light emitting device.

8. The light source device according to claim 6, wherein the second optical fiber includes a germanium oxide in a core thereof.

9. The light source device according to claim 7, wherein the one optical fiber includes a germanium oxide in a core thereof.

10. The light source device according to claim 1, wherein the first and second light sources are mounted on a substrate and disposed between the one or more phosphors of the third light emitting device and the substrate.

11. The light source device according to claim 1, wherein the second wavelength of the emission light of the second light source includes a wavelength in an infrared region.

12. An endoscope apparatus comprising:
an insertion portion;
an operation portion coupled to the insertion portion; and
the illumination device according to claim 1 coupled to the operation portion.

* * * * *